United States Patent
Seyedsayamdost et al.

(10) Patent No.: US 11,549,950 B2
(45) Date of Patent: Jan. 10, 2023

(54) CRYPTIC METABOLITES AND METHOD FOR ACTIVATING SILENT BIOSYNTHETIC GENE CLUSTERS IN DIVERSE MICROORGANISMS

(71) Applicant: The Trustees of Princeton University, Princeton, NJ (US)

(72) Inventors: Mohammad R. Seyedsayamdost, Princeton, NJ (US); Fei Xu, Princeton, NJ (US); Yihan Wu, Princeton, NJ (US); Leah Bushin, Princeton, NJ (US); Katherine Davis, Princeton, NJ (US)

(73) Assignee: THE TRUSTEES OF PRINCETON UNIVERSITY

( * ) Notice: Subject to any disclaimer, the term of this patent is extended or adjusted under 35 U.S.C. 154(b) by 304 days.

(21) Appl. No.: 16/634,388

(22) PCT Filed: Jul. 30, 2018

(86) PCT No.: PCT/US2018/044328
§ 371 (c)(1),
(2) Date: Jan. 27, 2020

(87) PCT Pub. No.: WO2019/027877
PCT Pub. Date: Feb. 7, 2019

(65) Prior Publication Data
US 2021/0041452 A1    Feb. 11, 2021

Related U.S. Application Data

(60) Provisional application No. 62/539,263, filed on Jul. 31, 2017.

(51) Int. Cl.
| | |
|---|---|
| *G01N 33/68* | (2006.01) |
| *C07K 9/00* | (2006.01) |
| *C12N 1/20* | (2006.01) |
| *C12N 1/38* | (2006.01) |
| *C12P 19/56* | (2006.01) |
| *C12P 21/00* | (2006.01) |
| *C12Q 1/18* | (2006.01) |

(52) U.S. Cl.
CPC ......... *G01N 33/6848* (2013.01); *C07K 9/008* (2013.01); *C12N 1/20* (2013.01); *C12N 1/38* (2013.01); *C12P 19/56* (2013.01); *C12P 21/005* (2013.01); *C12Q 1/18* (2013.01)

(58) Field of Classification Search
CPC .. C07K 9/008; C12N 1/20; C12N 1/38; C12P 19/56; C12P 21/005; C12Q 1/18; A61K 35/741; A61K 38/00
See application file for complete search history.

(56) References Cited

U.S. PATENT DOCUMENTS

| | | | |
|---|---|---|---|
| 2010/0285446 A1 | 11/2010 | Vertes et al. | |
| 2016/0272682 A1* | 9/2016 | Boger | A61K 38/14 |
| 2016/0324162 A1 | 11/2016 | Majeed et al. | |
| 2017/0022532 A1 | 1/2017 | Seyedsayamdost | |

OTHER PUBLICATIONS

Search Report for corresponding European Application No. 1884142, dated Nov. 17, 2021.
Everest et al., "Evaluation of the antibiotic biosynthetic potential of the genus *Amycolatopsis* and description of *Amycolatopsis circi* sp. nov.• *Amycolatopsis equina* sp. nov. and *Amycolatopsis hippodromi* sp. nov", Journal of Applied Microbiology, vol. 111, pp. 300-311, Jan. 1, 2011.
Zarins-Tutt et al., "Prospecting for new bacterial metabolites: a glossary of approaches for inducing. activating and upregulating the biosynthesis of bacterial cryptic or silent natural products", Natural Product Reports, vol. 33, No. 1, pp. 54-72, Jan. 1, 2016.
International Search Report and Written Opinion for PCT/US2018/044328, dated Nov. 7, 2018.
Al-Musallam, Aa et al., "*Amycolatopsis keratiniphila* sp. nov., a novel keratinolytic soil actinomycete from Kuwait", International Journal of Systematic and Evolutionary Microbiology, May 2003, vol. 53, No. 3; pp. 871-874.

* cited by examiner

*Primary Examiner* — Iqbal H Chowdhury
(74) *Attorney, Agent, or Firm* — Meagher Emanuel Laks Goldberg & Liao, LLP

(57) ABSTRACT

Disclosed herein is a rapid genetics-free method for eliciting and detecting cryptic metabolites using an imaging mass spectrometry-based approach. An organism of choice is challenged with elicitors from a small molecule library. The molecules elicited are then imaged by mass spec, which allows for rapid identification of cryptic metabolites. These are then isolated and characterized. Employing the disclosed approach activated production of cryptic glycopeptides from an actinomycete bacterium. The molecules that result, the keratinimicins and keratinicyclins, are metabolites with important structural features. At least two of these, keratinimicins B and C, are highly bioactive against several pathogenic strains. This approach will allow for rapid activation and identification of cryptic metabolites from diverse microorganisms in the future.

5 Claims, 50 Drawing Sheets
Specification includes a Sequence Listing.

Orfamide A: n = 9, R = CH₃
Orfamide B: n = 9, R = H

| Orfamide | Formula | [M+H]⁺calc | [M+H]⁺obs | Δppm |
|---|---|---|---|---|
| A | $C_{64}H_{114}N_{10}O_{17}$ | 1295.84417 | 1295.84380 | 0.3 |
| B | $C_{63}H_{112}N_{10}O_{17}$ | 1281.82852 | 1281.83038 | 1.5 |
| Canucin | Formula | [M+H]⁺calc | [M+H]⁺obs | Δppm |
| A | $C_{79}H_{102}N_{16}O_{19}$ | 1579.75854 | 1579.75592 | 1.7 |
| B | $C_{79}H_{102}N_{16}O_{18}$ | 1563.76363 | 1563.76242 | 0.8 |
| Keratinimicin | | [M+H]⁺calc | [M+H]⁺obs | Δppm |
| A | $C_{84}H_{92}Cl_2N_8O_{33}$ | 1811.52221 | 1811.52091 | 0.7 |
| B | $C_{78}H_{83}Cl_2N_9O_{26}$ | 1632.49045 | 1632.49397 | 2.2 |
| C | $C_{84}H_{90}Cl_2N_8O_{32}$ | 1793.51164 | 1793.50422 | 4.1 |
| D | $C_{84}H_{89}Cl_2N_7O_{34}$ | 1810.49057 | 1810.48720 | 1.9 |
| Keratinicyclin | | [M+H]⁺calc | [M+H]⁺obs | Δppm |
| A | $C_{77}H_{84}ClN_7O_{32}$ | 1654.49277 | 1654.49089 | 1.1 |
| B | $C_{77}H_{85}ClN_8O_{30}$ | 1637.51385 | 1637.51130 | 1.6 |
| C | $C_{71}H_{75}ClN_8O_{25}$ | 1475.46101 | 1475.45782 | 2.2 |

FIG. 3

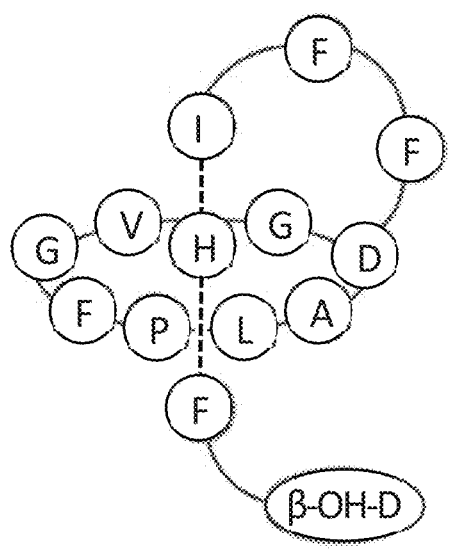
FIG. 4D
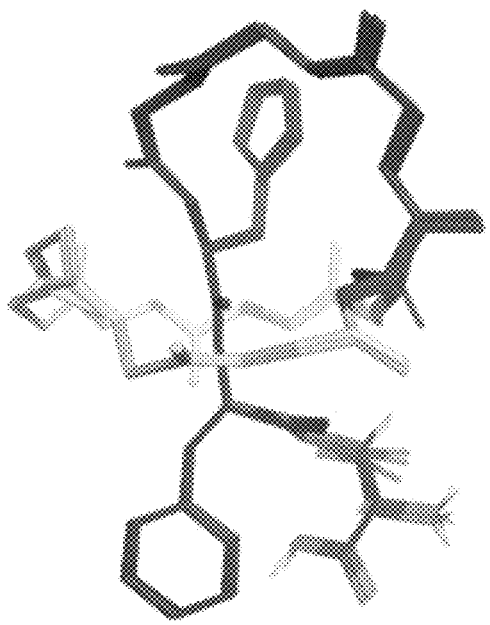 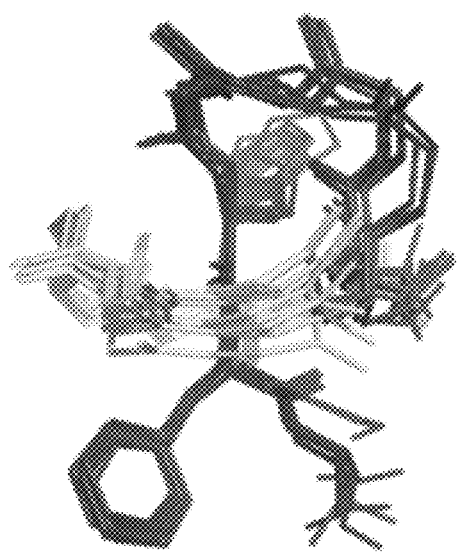
FIG. 4E          FIG. 4F

| Residue | | δH$^a$ | δC$^b$ | Residue | | δH$^a$ | δC$^b$ |
|---|---|---|---|---|---|---|---|
| Gly 1 | 1 | - | 169.9 | Phe 9 | 1 | - | ND |
| | 2 | 4.35, 3.66 | 42.5 | | 2 | 3.42 | 58.1 |
| | NH | 8.31 | - | | 3 | 3.54, 3.11 | 34.7 |
| Val 2 | 1 | - | 171.4 | | 4 | - | 139.7 |
| | 2 | 4.09 | 56.7 | | 5, 9 | 7.44 | 129.5 |
| | 3 | 2.07 | 33.3 | | 6, 8 | 7.29 | 128.0 |
| | 4 | 0.88 | 18.3 | | 7 | 7.20 | 126.0 |
| | 5 | 0.90 | 16.0 | | NH | 8.67 | - |
| | NH | 7.96 | - | Phe 10 | 1 | - | ND |
| Gly 3 | 1 | - | ND | | 2 | 3.84 | 61.2 |
| | 2 | 4.60, 3.756 | 42.3 | | 3 | 3.70, 3.04 | 35.4 |
| | NH | 9.02 | - | | 4 | - | 138.9 |
| Phe 4 | 1 | - | 171.6 | | 5, 9 | 7.18 | 126.4 |
| | 2 | 4.84 | 55.3 | | 6, 8 | 7.25 | 128.2 |
| | 3 | 3.39, 2.88 | 35.2 | | 7 | 7.33 | 126.5 |
| | 4 | | 137.3 | | NH | 7.80 | - |
| | 5, 9 | 7.37 | 128.5 | Ile 11 | 1 | - | 171.5 |
| | 6, 8 | 7.33 | 128.3 | | 2 | 4.31 | 58.7 |
| | 7 | 7.25 | 126.6 | | 3 | 1.85 | 37.1 |
| | NH | 8.75 | - | | 3' | 0.93 | 15.0 |
| Pro 5 | 1 | - | ND | | 4 | 1.13, 0.70 | 23.1 |
| | 2 | 3.46 | 63.2 | | 5 | 0.80 | 11.2 |
| | 3 | 2.54, 1.91 | 29.7 | | NH | 8.59 | - |
| | 4 | 2.03, 1.92 | 24.9 | His 12 | 1 | - | 172.1 |
| | 5 | 3.88, 3.50 | 47.6 | | 2 | 5.40 | 50.8 |
| Leu 6 | 1 | - | 173.0 | | 3 | 2.92, 2.75 | 27.6 |
| | 2 | 4.10 | 57.7 | | 4 | - | ND |
| | 3 | 1.70, 1.82 | 39.2 | | 5 | 7.24 | 119.1 |
| | 4 | 1.24 | 25.4 | | 6 | 8.67 | 133.3 |
| | 5 | 0.44 | 22.5 | | NH | 8.47 | - |
| | 6 | 0.90 | 20.24 | Phe 13 | 1 | - | ND |
| | NH | 8.02 | - | | 2 | 4.74 | 60.7 |
| Ala 7 | 1 | - | 172.1 | | 3 | 4.26, 3.56 | 38.6 |
| | 2 | 4.51 | 50.0 | | 4 | - | 137.0 |
| | 3 | 1.34 | 17.2 | | 5, 9 | 7.45 | 130.0 |
| | NH | 8.33 | - | | 6, 8 | 7.25 | 130.1 |
| Asp 8 | 1 | - | 172.8 | | 7 | 7.17 | 126.4 |
| | 2 | 4.56 | 48.0 | | NH | 8.26 | - |
| | 3 | 2.32 | 36.7 | βOHAsp 14 | 1 | - | ND |
| | 4 | - | ND | | 2 | 4.73 | 58.1 |
| | NH | 7.35 | | | 3 | 4.35 | 71.3 |
| | | | | | 4 | - | ND |
| | | | | | NH | 8.00 | |

FIG. 5A

| Parameter | R | S |
|---|---|---|
| # of distance constraints used for final structure calculation | 189 | 183 |
| average target function (*f*) | 0.23 ± 0.00 | 0.17 ± 8.47E-05 |
| average backbone RMSD to mean | 0.03 Å ± 0.01 | 0.01 Å ± 0.00 |
| average heavy atom RMSD to mean | 0.39 Å ± 0.04 | 0.46 Å ± 0.05 |
| # of violated distance constraints | 3 | 3 |
| # of violated van der Waals constraints | 0 | 0 |

| Residue | | δH[a] | δC[b] | Residue | | δH[a] | δC[b] |
|---|---|---|---|---|---|---|---|
| Gly | 1 | - | 169.9 | Phe | 1 | - | ND |
| | 2 | 4.36, 3.66 | 42.5 | | 2 | 3.42 | 58.1 |
| | NH | 8.44 | - | | 3 | 3.54, 3.11 | 34.8 |
| Val | 1 | - | 174.1 | | 4 | - | 139.8 |
| | 2 | 4.09 | 56.7 | | 5, 9 | 7.44 | 129.5 |
| | 3 | 2.07 | 33.3 | | 6, 8 | 7.29 | 128.1 |
| | 4 | 0.93 | 16.1 | | 7 | 7.20 | 126.0 |
| | 5 | 0.90 | 18.3 | | NH | 8.66 | - |
| | NH | 8.02 | - | Phe | 1 | - | ND |
| Gly | 1 | - | 171.5 | | 2 | 3.82 | 61.3 |
| | 2 | 4.57, 3.72 | 42.3 | | 3 | 3.70, 3.03 | 35.4 |
| | NH | 9.00 | - | | 4 | - | 138.1 |
| Phe | 1 | - | ND | | 5, 9 | 7.18 | 126.9 |
| | 2 | 4.84 | 55.3 | | 6, 8 | 7.25 | 128.1 |
| | 3 | 3.37, 2.85 | 35.2 | | 7 | 7.30 | 128.12 |
| | 4 | - | 137.3 | | NH | 7.82 | - |
| | 5, 9 | 7.35 | 128.4 | Ile | 1 | - | ND |
| | 6, 8 | 7.31 | 128.3 | | 2 | 4.31 | 58.7 |
| | 7 | 7.23 | 126.6 | | 3 | 1.86 | 37.0 |
| | NH | 8.68 | - | | 3' | 0.93 | 15.8 |
| Pro | 1 | - | 171.5 | | 4 | 1.11, 0.69 | 23.0 |
| | 2 | 3.50 | 63.2 | | 5 | 0.79 | 11.2 |
| | 3 | 2.54, 1.91 | 29.7 | | NH | 8.61 | - |
| | 4 | 2.02 | 24.9 | His | 1 | - | 175.3 |
| | 5 | 3.88, 3.50 | 47.6 | | 2 | 5.37 | 50.9 |
| Leu | 1 | - | 172.1 | | 3 | 2.92, 2.76 | 27.6 |
| | 2 | 4.13 | 57.7 | | 4 | - | ND |
| | 3 | 1.75, 1.87 | 39.6 | | 5 | 7.15 | 119.8 |
| | 4 | 1.28 | 25.4 | | 6 | 8.53 | 133.3 |
| | 5 | 0.50 | 22.6 | | NH | 8.49 | - |
| | 6 | 0.91 | 20.2 | Phe | 1 | - | 173.9 |
| | NH | 8.08 | - | | 2 | 4.76 | 60.5 |
| Ala | 1 | - | 172.0 | | 3 | 4.27, 3.50 | 38.2 |
| | 2 | 4.55 | 50.0 | | 4 | - | 136.9 |
| | 3 | 1.33 | 17.1 | | 5, 9 | 7.31 | 129.9 |
| | NH | 8.38 | - | | 6, 8 | 7.23 | 130.0 |
| Asp | 1 | - | ND | | 7 | 7.17 | 126.4 |
| | 2 | 4.58 | 48.1 | | NH | 8.28 | - |
| | 3 | 2.31 | 36.7 | Asp | 1 | - | ND |
| | 4 | - | ND | | 2 | 4.29 | 50.9 |
| | NH | 7.34 | - | | 3 | 2.94, 2.69 | 36.2 |
| | | | | | 4 | - | ND |
| | | | | | NH | 8.04 | - |

FIG. 7A

| Gene | Length (AA) | Homology-Based Predicted Function |
|---|---|---|
| canA | 40 | leader/core peptide, putative Class II |
| canB | 625 | asparagine synthase |
| canC | 85 | PqqD family protein |
| canD | 137 | transglutaminase-like superfamily protein |
| canE | 283 | TauD/TfdA family dioxygenase |

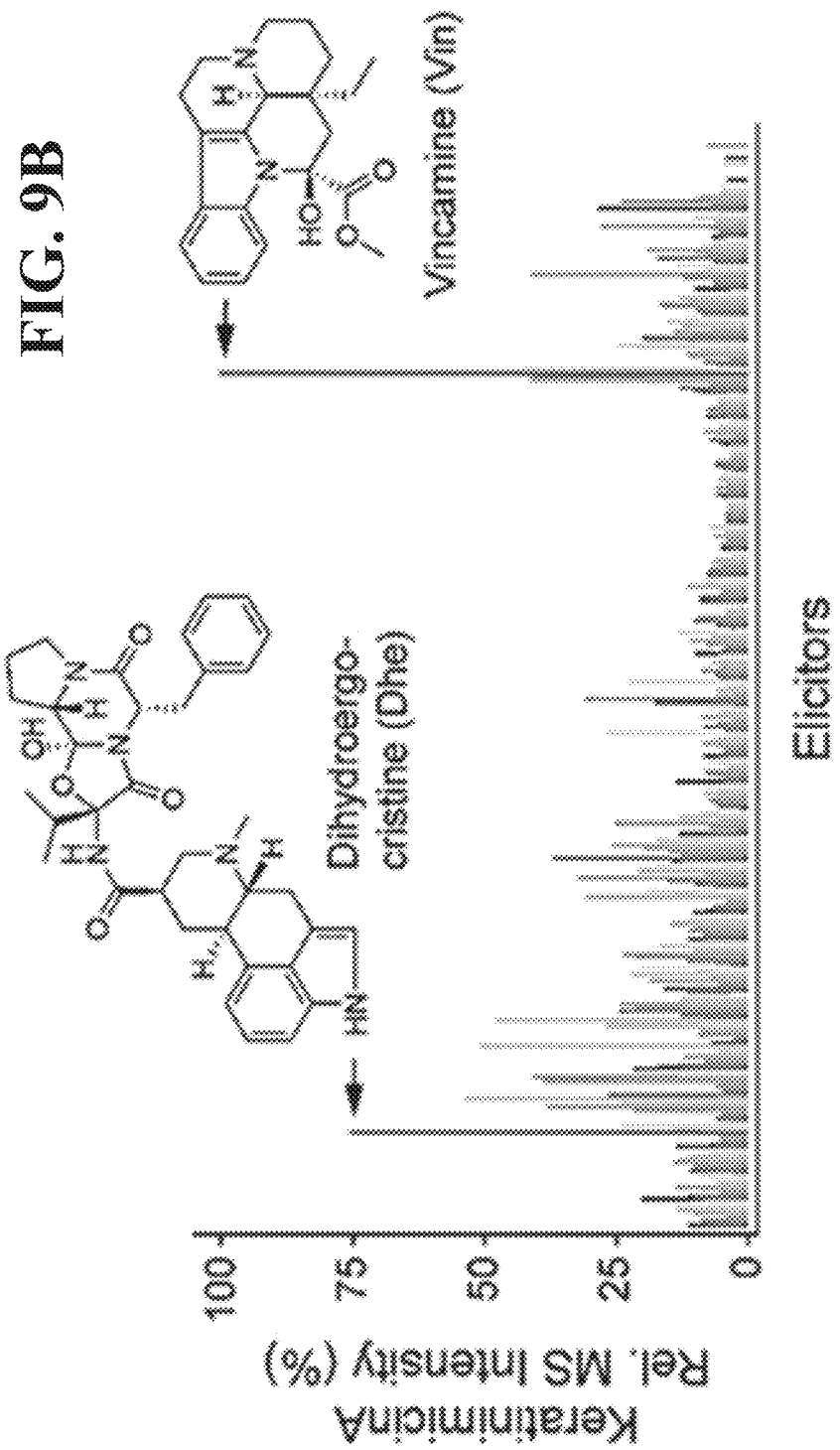

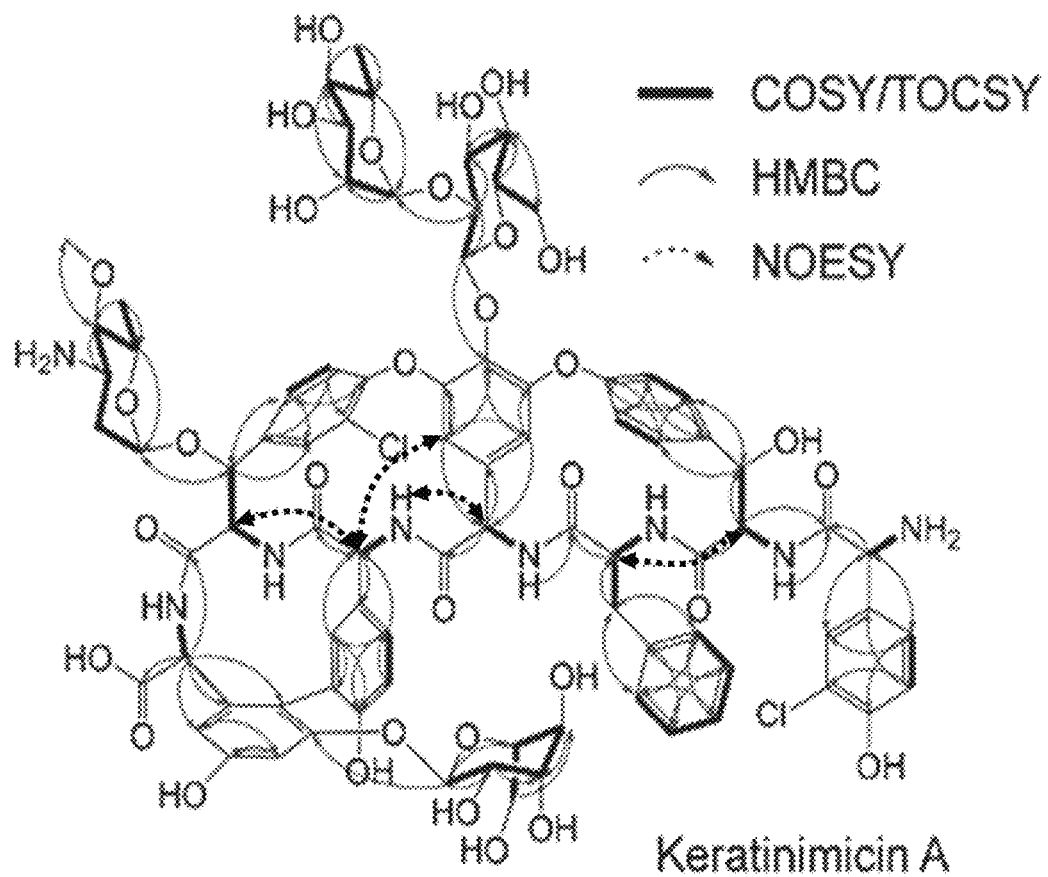
Keratinimicin A
FIG. 9D
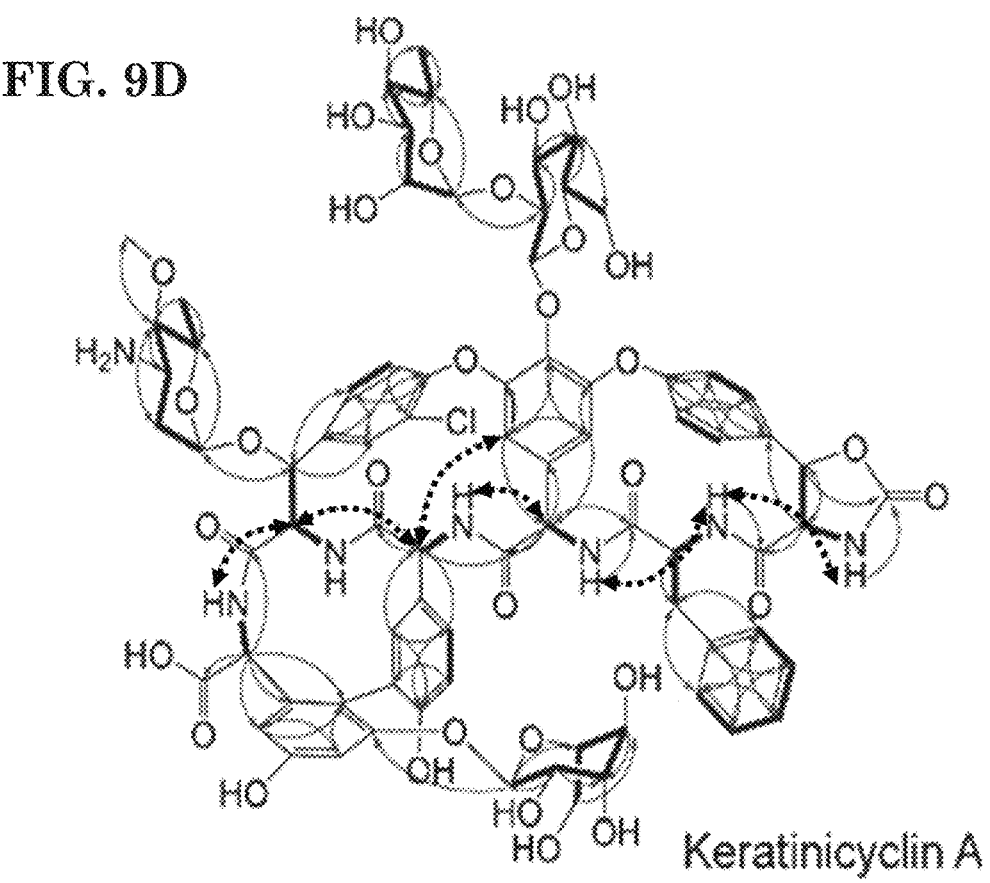
Keratinicyclin A

| Gene | Length (AA) | Homology-Based Predicted Function |
|---|---|---|
| vanH | 291 | D-lactate dehydrogenase |
| vanA | 348 | D-alanine--(R)-lactate ligase |
| vanX | 202 | D-Ala-D-Ala dipeptidase VanX |
| ajrR | 340 | StrR-like transcriptional regulator |
| pdh | 303 | prephenate dehydrogenase |
| tri | 644 | ABC transporter |
| kerA | 2082 | NRPS (A-T-C-A-T-E) |
| kerB | 1055 | NRPS (C-A-T) |
| kerC | 4059 | NRPS (C-A-T-E-C-A-T-E-C-A-T) |
| kerD | 1864 | NRPS (C-A-T-X-TE) |
| mbtH | 69 | mbtH protein |
| oxyA | 401 | cytochrome P450 |
| ker1 | 61 | hypothetical protein |
| oxyB | 398 | cytochrome P450 |
| oxyC | 406 | cytochrome P450 |
| khal | 491 | Halogenase |
| gtfA | 363 | Glycosyltransferase |
| gtfB | 408 | Glycosyltransferase |
| kerM | 309 | O-methyltransferase |
| gtfC | 408 | Glycosyltransferase |
| ker2 | 270 | PIG-L family deacetylase |
| gtfD | 623 | Mannosyltransferase |
| hpgT | 434 | Aminotransferase |
| kph | 276 | α/β fold hydrolase |
| kerE | 577 | AMP-dependent synthetase and ligase |
| oxyD | 396 | cytochrome P450 |
| hmaS | 350 | 4-hydroxyphenylpyruvate dioxygenase |
| hmo | 358 | phenylglycolate oxidase |
| ker3 | 448 | cation/H(+) antiporter |
| kraA | 476 | NDP-hexose 2,3-dehydratase |
| kraB | 325 | NAD-dependent epimerase/dehydratase |
| kraC | 369 | Aminotransferase |
| kraD | 205 | dTDP-4-keto-6-deoxy-D-glucose epimerase |
| dpgA | 366 | type III polyketide synthase |
| dpgB | 209 | enoyl-CoA hydratase |
| dpgC | 404 | enoyl-CoA hydratase |
| dpgD | 263 | enoyl-CoA hydratase |
| dahp | 358 | 3-deoxy-7-phosphoheptulonate synthase |
| ker4 | 188 | hypothetical protein |

FIG. 9H

| | C/H | δH[a] | Multiplicity (Hz) | δC[b] | | C/H | δH[a] | Multiplicity (Hz) | δC[b] |
|---|---|---|---|---|---|---|---|---|---|
| A | NH | 8.54 | UM | - | F | NH | 7.42 | UM | - |
| | COOH | - | - | 173.2 | | COOH | - | - | 169.5 |
| | α | 4.42 | d (6.1) | 57.6 | | α | 4.45 | q (9.8) | 56.4 |
| | 1 | - | - | 137.7 | | β | 2.69, 2.55 | d (7.0, 9.7) | 39.4 |
| | 2 | 6.57 | s | 109.1 | | 1 | - | - | 137.0 |
| | 3 | - | - | 157.7 | | 2 | 6.87 | d (7.5) | 129.5 |
| | 4 | 6.69 | s | 102.0 | | 3 | 6.91 | t (7.4) | 128.5 |
| | 5 | - | - | 155.2 | | 4 | 7.03 | t (7.3) | 126.8 |
| | 6 | - | - | 120.8 | G | NH | ND | - | - |
| B | NH | - | - | - | | COOH | - | - | 174.3 |
| | COOH | - | - | 173.2 | | α | 4.41 | d (3.9) | 59.0 |
| | α | 4.48 | d (3.9) | 54.2 | | 1 | - | - | ND |
| | 1 | - | - | ND | | 2 | 7.44 | s | 129.3 |
| | 2 | 7.18 | s | 136.2 | | 3 | - | - | 119.2 |
| | 3 | - | - | 120.8 | | 4 | - | - | 152.9 |
| | 4 | - | - | 155.8 | | 5 | 6.94 | d (8.0) | 116.7 |
| | 5 | 6.80 | UM | 116.2 | | 6 | 7.21 | UM | 127.8 |
| | 6 | 6.80 | UM | 126.2 | Ag | 1 | 5.18 | UM | 98.1 |
| C | NH | 6.92 | - | - | | 2 | 3.19 | t (4.1) | 70.4 |
| | COOH | - | - | 167.0 | | 3 | 3.22 | t (8.9) | 70.7 |
| | α | 4.23 | d (11.4) | 61.5 | | 4 | 3.39 | t (9.2) | 66.9 |
| | β | 5.11 | UM | 74.8 | | 5 | 3.49 | UM | 74.2 |
| | 1 | - | - | 138.8 | | 6 | 3.49, 3.45 | UM | 61.2 |
| | 2 | 7.89 | s | 129.3 | Cg | 1 | 4.67 | UM | 94.2 |
| | 3 | - | - | 127.5 | | 2 | 2.09, 1.48 | UM | 37.2 |
| | 4 | - | - | 150.0 | | 3 | 3.23 | m | 47.2 |
| | 5 | 7.32 | d (8.3) | 124.2 | | 3-NH₂ | ND | - | - |
| | 6 | 7.36 | d (8.3) | 127.8 | | 4 | 2.57 | t (9.6) | 86.5 |
| D | NH | 8.19 | UM | - | | 4-OMe | 3.33 | s | 58. |
| | COOH | - | - | 170.3 | | 5 | 3.64 | m | 67.3 |
| | α | 5.62 | d (8.5) | 54.6 | | 6 | 1.17 | d (5.7) | 18.7 |
| | 1 | - | - | 133.7 | Dg | 1 | 5.67 | d (7.4) | 99.8 |
| | 2 | 5.17 | s | 104.9 | | 2 | 3.62 | t (8.2) | 77.1 |
| | 3 | - | - | 151.4 | | 3 | 3.46 | t (8.6) | 78.2 |
| | 4 | - | - | 132.4 | | 4 | 3.22 | t (8.9) | 70.8 |
| | 5 | - | - | 153.1 | | 5 | 3.29 | m (4.6,10.2) | 78.1 |
| | 6 | 5.65 | s | 108.4 | | 6 | 3.72 | d (10.2) | 61.4 |
| E | NH | ND | - | - | Dg' | 1' | 5.18 | UM | 100.6 |
| | COOH | - | - | 168.5 | | 2' | 3.71 | t (3.2) | 71.1 |
| | α | 4.52 | t (3.8) | 59.7 | | 3' | 3.5 | t (10.2) | 71.1 |
| | β | 5.2 | d (4.1) | 71.5 | | 4' | 3.2 | t (10.2) | 72.2 |
| | 1 | - | - | 137.6 | | 5' | 4.12 | m (6.2) | 68.8 |
| | 2 | 7.78 | d (8.3) | 128.2 | | 6' | 1.08 | d (6.0) | 18.5 |
| | 3 | 7.22 | d (6.3) | 122.9 | | | | | |
| | 4 | - | - | 155.2 | | | | | |
| | 5 | 7.13 | d (8.4) | 124.1 | | | | | |
| | 6 | 7.05 | d (8.4) | 128.6 | | | | | |

[a]800 MHz, [b]determined by edited HSQC and HMBC, UM: unresolved multiplicity, ND: not detected.

FIG. 11A

| | C/H | δH[a] | Multiplicity (Hz) | δC[b] | | C/H | δH[a] | Multiplicity (Hz) | δC[b] |
|---|---|---|---|---|---|---|---|---|---|
| A | NH | 8.47 | UM | - | F | NH | 7.3 | - | - |
| | COOH | - | - | 173.3 | | COOH | - | - | 169.5 |
| | α | 4.42 | d (6.1) | 57.6 | | α | 4.5 | q (9.2) | 55.5 |
| | 1 | - | - | 137.7 | | β | 2.61, 2.57 | d (6.9, 7.0) | 40.0 |
| | 2 | 6.53 | s | 109.0 | | 1 | - | - | 136.3 |
| | 3 | - | - | 157.6 | | 2 | 6.79 | d (7.7) | 129.1 |
| | 4 | 6.66 | s | 102.7 | | 3 | 6.86 | t (7.3) | 128.3 |
| | 5 | - | - | 155.1 | | 4 | 6.99 | t (7.2) | 126.4 |
| | 6 | - | - | 121.2 | | COOH | - | - | 172.0 |
| B | NH | 8.5 | UM | - | G | CO | - | - | 183.2 |
| | COOH | - | - | 174.5 | | 1 | - | - | 124.5 |
| | α | 4.45 | UM | 54.1 | | 2 | 7.98 | s | 131.9 |
| | 1 | - | - | ND | | 3 | - | - | 115.6 |
| | 2 | 7.22 | s | 136.2 | | 4 | - | - | 152.9 |
| | 3 | - | - | 121.5 | | 5 | 6.34 | d (6.6) | 119.6 |
| | 4 | - | - | 155.8 | | 6 | 7.69 | d (8.5) | 132.9 |
| | 5 | 6.82 | d (8.2) | 115.9 | Ag | 1 | 5.15 | UM | 98.0 |
| | 6 | 6.8 | UM | 125.8 | | 2 | 3.11 | UM | 70.0 |
| C | NH | 7.19 | UM | - | | 3 | 3.16 | t (8.2) | 70.6 |
| | COOH | - | - | 167.2 | | 4 | 3.36 | t (9.4) | 66.9 |
| | α | 4.23 | t (7.5) | 61.23 | | 5 | 3.49 | t (7.7) | 74.1 |
| | β | 5.07 | UM | 74.8 | | 6 | 3.45, 3.49 | UM | 61.2 |
| | 1 | - | - | 138.7 | Cg | 1 | 4.72 | UM | 93.4 |
| | 2 | 7.86 | s | 129.1 | | 2 | 2.16, 1.63 | UM | 35.0 |
| | 3 | - | - | 127.7 | | 3 | 3.5 | t (8.8) | 46.9 |
| | 4 | - | - | 149.9 | | 3-NH₂ | ND | - | - |
| | 5 | 7.3 | d (7.8) | 123.9 | | 4 | 2.78 | UM | 83.5 |
| | 6 | 7.32 | d (10.5) | 127.3 | | 4-OMe | 3.33 | s | 58.1 |
| D | NH | 7.79 | d (7.6) | - | | 5 | 3.67 | UM | 67.0 |
| | COOH | - | - | 170.5 | | 6 | 1.18 | d (5.7) | 18.3 |
| | α | 5.61 | d (9.4) | 54.1 | Dg | 1 | 5.63 | d (7.5) | 99.6 |
| | 1 | - | - | 133.5 | | 2 | 3.59 | t (8.2) | 77.3 |
| | 2 | 5.1 | s | 104.3 | | 3 | 3.48 | t (7.7) | 77.5 |
| | 3 | - | - | 151.6 | | 4 | 3.21 | t (8.7) | 70.4 |
| | 4 | - | - | 132.2 | | 5 | 3.31 | UM | 77.8 |
| | 5 | - | - | 153.2 | | 6 | 3.72, 3.45 | d (10.5) | 61.3 |
| | 6 | 5.58 | s | 108.1 | Dg' | 1' | 5.39 | UM | 95.5 |
| E | NH | 7.62 | d (7.9) | - | | 2' | 2.14, 1.67 | UM | 34.3 |
| | COOH | - | - | 167.8 | | 3' | 3.16 | m (8.2) | 49.5 |
| | α | 4.77 | t (3.8) | 59.3 | | 3'-NH₂ | ND | - | - |
| | β | 5.24 | d (2.6) | 71.2 | | 4' | 3.06 | UM | 73.1 |
| | 1 | - | - | 137.3 | | 5' | 4.23 | UM | 68.4 |
| | 2 | 7.62 | d (7.9) | 128.1 | | 6' | 1.08 | d (6.0) | 18.5 |
| | 3 | 7.2 | d (7.8) | 122.7 | | | | | |
| | 4 | - | - | 155.2 | | | | | |
| | 5 | 7.13 | d (7.9) | 123.9 | | | | | |
| | 6 | 7.07 | d (8.1) | 128.4 | | | | | |

[a]800 MHz, [b]determined by edited HSQC and HMBC, UM: unresolved multiplicity, ND: not detected.

FIG. 13A

| | C/H | $\delta H^a$ | Multiplicity (Hz) | $\delta C^b$ | | C/H | $\delta H^a$ | Multiplicity (Hz) | $\delta C^b$ |
|---|---|---|---|---|---|---|---|---|---|
| A | NH | 8.47 | UM | - | F | NH | 7.3 | - | - |
| | COOH | - | - | 173.3 | | COOH | - | - | 169.5 |
| | α | 4.42 | d (6.1) | 57.6 | | α | 4.5 | q (9.2) | 55.5 |
| | 1 | - | - | 137.7 | | β | 2.61, 2.57 | d (6.9, 7.0) | 40.0 |
| | 2 | 6.53 | s | 109.0 | | 1 | - | - | 136.3 |
| | 3 | - | - | 157.6 | | 2 | 6.79 | d (7.7) | 129.1 |
| | 4 | 6.66 | s | 102.7 | | 3 | 6.86 | t (7.3) | 128.3 |
| | 5 | - | - | 155.1 | | 4 | 6.99 | t (7.2) | 126.4 |
| | 6 | - | - | 121.2 | | COOH | - | - | 172.0 |
| B | NH | 8.5 | UM | - | | CO | - | - | 183.2 |
| | COOH | - | - | 174.5 | | 1 | - | - | 124.5 |
| | α | 4.45 | UM | 54.1 | G | 2 | 7.98 | s | 131.9 |
| | 1 | - | - | ND | | 3 | - | - | 115.6 |
| | 2 | 7.22 | s | 136.2 | | 4 | - | - | 152.9 |
| | 3 | - | - | 121.5 | | 5 | 6.34 | d (6.6) | 119.6 |
| | 4 | - | - | 155.8 | | 6 | 7.69 | d (8.5) | 132.9 |
| | 5 | 6.82 | d (8.2) | 115.9 | | 1 | 5.15 | UM | 98.0 |
| | 6 | 6.8 | UM | 125.8 | | 2 | 3.11 | UM | 70.0 |
| C | NH | 7.19 | UM | - | Ag | 3 | 3.16 | t (8.2) | 70.6 |
| | COOH | - | - | 167.2 | | 4 | 3.36 | t (9.4) | 66.9 |
| | α | 4.23 | t (7.5) | 61.23 | | 5 | 3.49 | t (7.7) | 74.1 |
| | β | 5.07 | UM | 74.8 | | 6 | 3.45, 3.49 | UM | 61.2 |
| | 1 | - | - | 138.7 | | 1 | 4.72 | UM | 93.4 |
| | 2 | 7.86 | s | 129.1 | | 2 | 2.16, 1.63 | UM | 35.0 |
| | 3 | - | - | 127.7 | | 3 | 3.5 | t (8.8) | 46.9 |
| | 4 | - | - | 149.9 | Cg | 3-NH₂ | ND | - | - |
| | 5 | 7.3 | d (7.8) | 123.9 | | 4 | 2.78 | UM | 83.5 |
| | 6 | 7.32 | d (10.5) | 127.3 | | 4-OMe | 3.33 | s | 58.1 |
| D | NH | 7.79 | d (7.6) | - | | 5 | 3.67 | UM | 67.0 |
| | COOH | - | - | 170.5 | | 6 | 1.18 | d (5.7) | 18.3 |
| | α | 5.61 | d (9.4) | 54.1 | | 1 | 5.63 | d (7.5) | 99.6 |
| | 1 | - | - | 133.5 | | 2 | 3.59 | t (8.2) | 77.3 |
| | 2 | 5.1 | s | 104.3 | Dg | 3 | 3.48 | t (7.7) | 77.5 |
| | 3 | - | - | 151.6 | | 4 | 3.21 | t (8.7) | 70.4 |
| | 4 | - | - | 132.2 | | 5 | 3.31 | UM | 77.8 |
| | 5 | - | - | 153.2 | | 6 | 3.72, 3.45 | d (10.5) | 61.3 |
| | 6 | 5.58 | s | 108.1 | | 1' | 5.39 | UM | 95.5 |
| E | NH | 7.62 | d (7.9) | - | | 2' | 2.14, 1.67 | UM | 34.3 |
| | COOH | - | - | 167.8 | Dg' | 3' | 3.16 | m (8.2) | 49.5 |
| | α | 4.77 | t (3.8) | 59.3 | | 3'-NH₂ | ND | - | - |
| | β | 5.24 | d (2.6) | 71.2 | | 4' | 3.06 | UM | 73.1 |
| | 1 | - | - | 137.3 | | 5' | 4.23 | UM | 68.4 |
| | 2 | 7.62 | d (7.9) | 128.1 | | 6' | 1.08 | d (6.0) | 18.5 |
| | 3 | 7.2 | d (7.8) | 122.7 | | | | | |
| | 4 | - | - | 155.2 | | | | | |
| | 5 | 7.13 | d (7.9) | 123.9 | | | | | |
| | 6 | 7.07 | d (8.1) | 128.4 | | | | | |

$^a$800 MHz, $^b$determined by edited HSQC and HMBC, UM: unresolved multiplicity, ND: not detected.

FIG. 14A

| | C/H | δH[a] | Multiplicity (Hz) | δC[b] | | C/H | δH[a] | Multiplicity (Hz) | δC[b] |
|---|---|---|---|---|---|---|---|---|---|
| | NH | 8.32 | UM | - | | NH | ND | - | - |
| | COOH | - | - | ND | | COOH | - | - | ND |
| | α | 4.43 | d (5.1) | 57.3 | | α | 4.5 | q (8.2) | 55.8 |
| | 1 | - | - | - | F | β | 2.59 | d (6.3) | 40.3 |
| A | 2 | 6.48 | s | 108.6 | | 1 | - | - | ND |
| | 3 | - | - | - | | 2 | 6.78 | d (7.6) | 129.3 |
| | 4 | 6.69 | s | 103.2 | | 3 | 6.84 | t (7.5) | 128.5 |
| | 5 | - | - | ND | | 4 | 6.98 | t (7.4) | 126.6 |
| | 6 | - | - | ND | | COOH | - | - | ND |
| | NH | 8.55 | UM | - | | CO | - | - | ND |
| | COOH | - | - | ND | | 1 | - | - | ND |
| | α | 4.44 | UM | 54.3 | | 2 | 7.96 | s | 131.4 |
| | 1 | - | - | - | G | 3 | - | - | ND |
| B | 2 | 7.23 | s | 136.2 | | 4 | - | - | ND |
| | 3 | - | - | ND | | 5 | 6.3 | d (6.3) | 119.8 |
| | 4 | - | - | ND | | 6 | 7.67 | d (8.6) | 128.3 |
| | 5 | 6.83 | d (7.5) | 116.2 | | 1 | 5.16 | UM | 98.3 |
| | 6 | 6.81 | d (8.8) | 126.2 | | 2 | 3.12 | UM | 70.2 |
| | NH | ND | - | - | Ag | 3 | 3.2 | t (8.7) | 70.8 |
| | COOH | - | - | ND | | 4 | 3.37 | UM | 67.1 |
| | α | 4.25 | d (11.5) | 61.5 | | 5 | 3.48 | t (7.7) | 74.3 |
| | β | 5.07 | UM | 74.4 | | 6 | 3.47 | UM | 61.4 |
| C | 1 | - | - | ND | | 1 | 4.73 | UM | 93.7 |
| | 2 | 7.86 | s | 129.3 | | 2 | 2.16, 1.61 | UM | 35.3 |
| | 3 | - | - | ND | | 3 | 3.49 | UM | 47.3 |
| | 4 | - | - | ND | Cg | 3-NH₂ | ND | - | - |
| | 5 | 7.28 | d (8.3) | 124.1 | | 4 | 2.55 | UM | 86.7 |
| | 6 | 7.32 | d (8.4) | 127.5 | | 4-OMe | 3.34 | s | 58.5 |
| | NH | ND | - | - | | 5 | 3.65 | m | 67.3 |
| | COOH | - | - | ND | | 6 | 1.19 | d (5.6) | 18.5 |
| | α | 5.59 | d (9.0) | 54.3 | | 1 | 5.63 | d (7.4) | 99.8 |
| | 1 | - | - | ND | | 2 | 3.59 | t (8.3) | 77.6 |
| D | 2 | 5.09 | s | 104.4 | Dg | 3 | 3.45 | UM | 77.8 |
| | 3 | - | - | ND | | 4 | 3.15 | d (9.1) | 70.9 |
| | 4 | - | - | ND | | 5 | 3.31 | m | 78.1 |
| | 5 | - | - | ND | | 6 | 3.73, 3.44 | UM | 61.5 |
| | 6 | 5.55 | s | 108.3 | | 1' | 5.13 | UM | 100.8 |
| | NH | 7.83 | d (8.5) | - | | 2' | 3.72 | UM | 71.0 |
| | COOH | - | - | ND | Dg' | 3' | 3.48 | UM | 71.1 |
| | α | 4.77 | dd (8.4,4.6) | 59.6 | | 4' | 3.21 | t (9.4) | 72.4 |
| | β | 5.23 | d (3.3) | 71.4 | | 5' | 4.08 | m | 68.8 |
| | 1 | - | - | ND | | 6' | 1.08 | d (6.1) | 18.4 |
| E | 2 | 7.61 | d (8.5) | 128.3 | | | | | |
| | 3 | 7.21 | dd (7.8,1.6) | 123.0 | | | | | |
| | 4 | - | - | ND | | | | | |
| | 5 | 7.13 | dd (7.8,1.7) | 124.1 | | | | | |
| | 6 | 7.06 | d (8.3) | 128.7 | | | | | |

[a]800 MHz, [b]determined by edited HSQC and HMBC, UM: unresolved multiplicity, ND: not detected.

FIG. 15A

| | C/H | δH$^a$ | Multiplicity (Hz) | δC$^b$ | | C/H | δH$^a$ | Multiplicity (Hz) | δC$^b$ |
|---|---|---|---|---|---|---|---|---|---|
| | NH | 8.7 | d (4.4) | - | | NH | 8.16 | UM | - |
| | COOH | - | - | 173.2 | | COOH | - | - | 166.5 |
| | α | 4.49 | d (5.8) | 57.3 | | α | 4.74 | UM | 62.8 |
| | 1 | - | - | 137.3 | | β | 5.93 | d (8.4) | 77.1 |
| A | 2 | 6.52 | s | 108.9 | | 1 | - | - | 137.6 |
| | 3 | - | - | 158.0 | E | 2 | 7.12 | d (8.1) | 128.8 |
| | 4 | 6.71 | s | 102.7 | | 3 | 7.22 | d (8.0) | 122.0 |
| | 5 | - | - | 155.6 | | 4 | - | - | 158.7 |
| | 6 | - | - | 121.5 | | 5 | ? | d (8.8) | 123.5 |
| | NH | 8.65 | d (3.5) | - | | 6 | 7.29 | d (8.5) | 127.5 |
| | COOH | - | - | ND | | NHCO | - | - | 160.1 |
| | α | 4.59 | d (3.9) | 54.2 | | NH | 7.84 | d (9.2) | - |
| | 1 | - | - | 132.8 | | COOH | - | - | 169.5 |
| B | 2 | 7.23 | s | 136.4 | | α | 4.34 | q (7.8, 9.2) | 57.6 |
| | 3 | - | - | 119.2 | F | β | 2.75, 2.58 | d (10.7) | 39.9 |
| | 4 | - | - | 156.0 | | 1 | - | - | 137.0 |
| | 5 | 6.84 | d (8.1) | 116.2 | | 2 | 6.85 | d (7.4) | 129.9 |
| | 6 | 6.82 | UM | 126.3 | | 3 | 6.8 | t (7.4) | 128.5 |
| | NH | 7.2 | - | - | | 4 | 6.97 | t (7.2) | 127.1 |
| | COOH | - | - | 167.7 | | 1 | 5.2 | UM | 98.3 |
| | α | 4.29 | d (11.3) | 61.6 | | 2 | 3.18 | t (3.1) | 70.4 |
| | β | 5.11 | UM | 75.2 | | 3 | 3.24 | t (3.6, 9.7) | 71.0 |
| C | 1 | - | - | 138.8 | Ag | 4 | 3.39 | t (9.7) | 67.1 |
| | 2 | 7.89 | s | 129.5 | | 5 | 3.48 | UM | 74.4 |
| | 3 | - | - | 127.5 | | 6 | 3.49, 3.45 | d (7.5) | 61.2 |
| | 4 | - | - | 150.0 | | 1 | 4.76 | t (4.0) | 93.9 |
| | 5 | 7.26 | d (8.2) | 124.0 | | 2 | 2.17, 1.65 | UM | 35.2 |
| | 6 | 7.35 | d (8.0) | 128.1 | | 3 | 3.52 | m (8.3) | 47.3 |
| | NH | 8.13 | d (8.5) | - | Cg | 3-NH$_2$ | ND | - | - |
| | COOH | - | - | 170.2 | | 4 | 2.8 | t (9.9) | 83.7 |
| | α | 5.56 | d (8.6) | 54.1 | | 4-OMe | 3.35 | s | 58.6 |
| | 1 | - | - | 133.7 | | 5 | 3.68 | m (6.0) | 67.3 |
| D | 2 | 5.11 | s | 105.0 | | 6 | 1.2 | d (5.5) | 18.8 |
| | 3 | - | - | 151.4 | | 1 | 5.63 | d (7.5) | 99.5 |
| | 4 | - | - | 132.4 | | 2 | 3.59 | t (8.4) | 77.7 |
| | 5 | - | - | 153.1 | Dg | 3 | 3.41 | t (9.0) | 78.1 |
| | 6 | 5.51 | s | 112.6 | | 4 | 3.14 | t (9.0) | 71.1 |
| | | | | | | 5 | 3.22 | m (8.7) | 78.7 |
| | | | | | | 6 | 3.72, 3.37 | d (9.4, 6.2) | 62.0 |
| | | | | | | 1' | 5.13 | UM | 101.2 |
| | | | | | Dg' | 2' | 3.71 | t (3.3) | 71.0 |
| | | | | | | 3' | 3.49 | t (9.2) | 71.4 |
| | | | | | | 4' | 3.2 | t (9.4) | 72.5 |

$^a$800 MHz, $^b$determined by edited HSQC and HMBC, UM: unresolved multiplicity, ND: not detected.

FIG. 16A

| | C/H | δH[a] | Multiplicity (Hz) | δC[b] | | C/H | δH[a] | Multiplicity (Hz) | δC[b] |
|---|---|---|---|---|---|---|---|---|---|
| | NH | 8.67 | d (4.8) | - | | NH | 8.19 | UM | - |
| | COOH | - | - | 173.2 | | COOH | - | - | ND |
| | α | 4.49 | d (5.8) | 57.5 | | α | 4.75 | UM | 62.6 |
| | 1 | - | - | - | | β | 5.93 | d (8.4) | 76.8 |
| A | 2 | 6.29 | s | 106.5 | | 1 | - | - | ND |
| | 3 | - | - | ND | E | 2 | 7.14 | dd (1.4,7.4) | 128.6 |
| | 4 | 6.42 | s | 102.7 | | 3 | 7.22 | d (7.1) | 121.8 |
| | 5 | - | - | ND | | 4 | - | - | ND |
| | 6 | - | - | ND | | 5 | 7 | dd (1.6,9.1) | 123.3 |
| | NH | 8.64 | d (3.2) | | | 6 | 7.3 | dd (1.5,9.1) | 127.5 |
| | COOH | - | - | ND | | NHCO | - | - | ND |
| | α | 4.59 | d (3.4) | 54.0 | | NH | 7.85 | d (9.1) | - |
| | 1 | - | - | ND | | COOH | - | - | ND |
| B | 2 | 7.23 | s | 136.3 | | α | 4.35 | q (8.7) | 57.3 |
| | 3 | - | - | ND | F | β | 2.76, 2.6 | t (10.3),d (7.1) | 39.7 |
| | 4 | - | - | ND | | 1 | - | - | ND |
| | 5 | 6.84 | d (8.9) | 116.2 | | 2 | 6.86 | d (7.7) | 129.6 |
| | 6 | 6.82 | dd (2.8,9.0) | 126.2 | | 3 | 6.8 | t (7.3) | 128.5 |
| | NH | ND | - | - | | 4 | 6.98 | t (7.2) | 126.9 |
| | COOH | - | - | 167.4 | | 1 | 5.19 | UM | 98.4 |
| | α | 4.29 | d (10.6) | 61.6 | | 2 | 3.18 | t (3.0) | 70.2 |
| | β | 5.13 | UM | 75.0 | Ag | 3 | 3.25 | t (9.0) | 70.8 |
| C | 1 | - | - | ND | | 4 | 3.4 | t (9.3) | 67.0 |
| | 2 | 7.9 | s | 129.3 | | 5 | 3.5 | m | 74.2 |
| | 3 | - | - | ND | | 6 | 3.48,3.46 | UM | 61.1 |
| | 4 | - | - | ND | | 1 | 4.75 | UM | 93.6 |
| | 5 | 7.28 | d (8.2) | 124.1 | | 2 | 2.19, 1.66 | UM | 35.0 |
| | 6 | 7.35 | d (7.4) | 127.9 | | 3 | 3.53 | m | 47.1 |
| | NH | 8.13 | d (8.6) | - | Cg | 3-NH₂ | ND | - | - |
| | COOH | - | - | ND | | 4 | 2.83 | t (9.6) | 83.4 |
| | α | 5.57 | d (8.6) | 54.0 | | 4-OMe | 3.34 | s | 58.4 |
| | 1 | - | - | ND | | 5 | 3.69 | m | 67.3 |
| D | 2 | 5.13 | s | 104.8 | | 6 | 1.2 | d (5.3) | 18.6 |
| | 3 | - | - | ND | | 1 | 5.64 | d (7.4) | 99.3 |
| | 4 | - | - | ND | | 2 | 3.59 | t (8.4) | 77.4 |
| | 5 | - | - | ND | Dg' | 3 | 3.43 | t (9.4) | 77.8 |
| | 6 | 5.53 | s | 112.4 | | 4 | 3.16 | t (9.0) | 70.7 |
| | | | | | | 5 | 3.23 | m | 78.4 |
| | | | | | | 6 | 3.72, 3.39 | d (10.8) | 61.6 |
| | | | | | | 1' | 5.37 | UM | 95.8 |
| | | | | | | 2' | 2.14, 1.69 | UM | 34.6 |
| | | | | | Dg' | 3' | 3.2 | m | 49.8 |
| | | | | | | 3'-NH₂ | ND | - | - |
| | | | | | | 4' | 3.06 | t (8.4) | 73.2 |

[a]800 MHz, [b]determined by edited HSQC and HMBC. UM: unresolved multiplicity, ND: not detected.

FIG. 17A

| | C/H | δH$^a$ | Multiplicity (Hz) | δC$^b$ | | C/H | δH$^a$ | Multiplicity (Hz) | δC$^b$ |
|---|---|---|---|---|---|---|---|---|---|
| | NH | 8.52 | UM | - | | NH | 8.14 | UM | - |
| | COOH | - | - | 173.3 | | COOH | - | - | 166.2 |
| | α | 4.44 | d (5.8) | 57.7 | | α | 4.75 | d (9.0) | 62.6 |
| | 1 | - | - | 137.3 | | β | 5.93 | d (8.2) | 76.8 |
| A | 2 | 6.34 | s | 106.6 | | 1 | - | - | 132.4 |
| | 3 | - | - | 157.5 | E | 2 | 7.12 | dd (1.7,8.2) | 128.6 |
| | 4 | 6.39 | s | 102.7 | | 3 | 7.22 | dd (2.3,) | 121.8 |
| | 5 | - | - | ND | | 4 | - | - | 158.7 |
| | 6 | - | - | 118.6 | | 5 | 7.02 | d (3.1,9.0) | 123.4 |
| | NH | 8.75 | d (3.4) | | | 6 | 7.31 | dd (2.1,8.5) | 127.5 |
| | COOH | - | - | ND | | NHCO | - | - | 159.7 |
| | α | 4.58 | d (4.3) | 54.1 | | NH | 7.84 | d (9.8) | - |
| | 1 | - | - | 126.4 | | COOH | - | - | 169.5 |
| B | 2 | 7.27 | s | 136.6 | | α | 4.31 | q (7.8, 9.2) | 57.6 |
| | 3 | - | - | 122.4 | F | β | 2.76, 2.60 | d (10.6) | 39.9 |
| | 4 | - | - | 155.9 | | 1 | - | - | 137.0 |
| | 5 | 6.76 | d (8.6) | 116.5 | | 2 | 6.88 | d (7.5) | 129.6 |
| | 6 | 6.82 | dd (1.8,8.6) | 125.7 | | 3 | 6.94 | t (7.6) | 128.5 |
| | NH | 6.91 | - | - | | 4 | 7.02 | t (7.4) | 126.7 |
| | COOH | - | - | ND | | 1 | 4.69 | UM | 94.0 |
| | α | 4.32 | t (8.7) | 61.5 | | 2 | 2.12, 1.54 | UM | 36.7 |
| | β | 5.13 | UM | 74.8 | | 3 | 3.31 | dd (10.2) | 47.3 |
| | 1 | - | - | 138.8 | Cg | 3-NH2 | ND | - | - |
| C | 2 | 7.93 | s | 129.4 | | 4 | 2.65 | t (9.7) | 85.7 |
| | 3 | - | - | 127.5 | | 4-OMe | 3.34 | s | 58.3 |
| | 4 | - | - | 149.9 | | 5 | 3.65 | UM | 67.8 |
| | 5 | 7.26 | d (8.6) | 124.1 | | 6 | 1.18 | d (5.8) | 18.7 |
| | 6 | 7.38 | dd (1.7,8.0) | 127.9 | | 1 | 5.65 | d (7.6) | 99.2 |
| | NH | 8.24 | d (8.7) | - | | 2 | 3.59 | t (8.1) | 77.5 |
| | COOH | - | - | 170.0 | | 3 | 3.43 | UM | 78.0 |
| | α | 5.64 | d (8.9) | 54.2 | Dg | 4 | 3.15 | t (9.5) | 70.8 |
| | 1 | - | - | 134.5 | | 5 | 3.23 | m (6.0) | 78.5 |
| D | 2 | 5.17 | s | 104.8 | | 6 | 3.73, 3.38 | d (10.3) | 61.9 |
| | 3 | - | - | ND | | 1' | 5.35 | UM | 96.1 |
| | 4 | - | - | 133.1 | | 2' | 2.1, 1.6 | UM | 35.4 |
| | 5 | - | - | ND | Dg' | 3' | 3.11 | UM | 49.8 |
| | 6 | 5.52 | s | 112.4 | | 3'-NH2 | ND | - | - |
| | | | | | | 4' | 2.94 | t (10.1) | 74.5 |
| | | | | | | 5' | 4.17 | m (6.4,8.8) | 68.5 |

$^a$800 MHz, $^b$determined by edited HSQC and HMBC, UM: unresolved multiplicity, ND: not detected.

FIG. 18A

| Strain | Keratini-micin A | Keratini-micin C | Keratini-cyclin B | Keratini-cyclin C | Control drug[b] |
|---|---|---|---|---|---|
| Bacterium[c] | | | | | |
| S. aureus | 4.4 | 4.5 | >39 | —[d] | 2.1 (V), 1.5 (C) |
| S. aureus MRSA | 2.2 | 4.5 | >39 | — | 0.7 (V), 12.1 (C) |
| S. pneumoniae PSPP | 0.1 | 0.6 | 19.5 | — | 0.4 (V), 1.5 (C) |
| S. pyogenes | 0.3 | 1.1 | 19.5 | — | 0.2 (V), 0.8 (C) |
| S. agalactiae | 0.6 | 2.2 | 39 | — | 0.2 (V), 0.8 (C) |
| E. faecalis VSE | 2.2 | 4.5 | >39 | — | 2.8 (V), 6.0 (C) |
| E. faecalis VRE | >35 | >35 | >39 | — | >44 (V), >12.1 (C) |
| B. subtilis | 0.3 | 1.1 | 19.5 | — | 0.1 (V), 0.2 (C) |
| E. coli | >35 | >35 | >39 | — | >44 (V), 0.1 (C) |
| K. pneumoniae | >35 | >35 | >39 | — | >44 (V), 0.1 (C) |
| E. cloacae | >35 | >35 | >39 | — | >44 (V), 0.1 (C) |
| P. aeruginosa | >35 | >35 | >39 | — | >44 (V), 3.0 (C) |
| A. baumannii | >35 | >35 | >39 | — | >44 (V), 3.0 (C) |
| V. cholerae | >35 | >35 | >39 | — | >44 (V), 0.8 (C) |
| C. difficile | 0.3 | 0.3 | 9.8 | — | 1.5 (M) |
| B. fragilis | >35 | >35 | >39 | — | 11.7 (M) |
| Virus[c] | | | | | |
| Influenza A | — | — | 83 | >101 | 3.1 (O) |
| Influenza B | — | — | >83 | >101 | 8.8 (O) |
| HSV-1 | — | — | >83 | >101 | 32 (A) |
| HSV-2 | — | — | >83 | >101 | 31 (A) |
| Vaccinia | — | — | >83 | >101 | — |
| Rhinovirus | — | — | >83 | >101 | 180.3 (R) |
| Respiratory Syncytial Virus | — | — | 2.3 | 2.5 | 22.1 (R) |

[b]Control drugs are abbreviated as follows: V, vancomycin; C, ciprofloxacin, M, metronidazole; O, oseltamivir; A, acyclovir; R, ribavirin.
[c]MIC and IC$_{50}$ values were determined in antibacterial and antiviral assays, respectively.
[d]Not determined.

FIG. 19

SEQUENCE LISTING

<160> NUMBER OF SEQ ID NOS: 1

<210> SEQ ID NO 1
<211> LENGTH: 14
<212> TYPE: PRT
<213> ORGANISM: Streptomyces canus

<400> SEQUENCE: 1

Gly Val Gly Phe Pro Leu Ala Asp Phe Phe Ile His Phe Asp
1               5                   10

CRYPTIC METABOLITES AND METHOD FOR ACTIVATING SILENT BIOSYNTHETIC GENE CLUSTERS IN DIVERSE MICROORGANISMS

CROSS-REFERENCE TO RELATED APPLICATIONS

This application claims priority to U.S. Provisional Application No. 62/539,263, filed Jul. 31, 2017, which is herein incorporated by reference in its entirety.

STATEMENT REGARDING FEDERALLY SPONSORED RESEARCH OR DEVELOPMENT

This invention was made with government support under Grant # AI124786 awarded by the National Institutes of Health. The government has certain rights in this invention.

REFERENCE TO SEQUENCE LISTING SUBMITTED ELECTRONICALLY

The Sequence Listing filed electronically herewith is also hereby incorporated by reference in its entirety (File Name: PRIN-57276_ST25.txt; Date Created: Jul. 13, 2018; File Size: 524 bytes).

TECHNICAL FIELD

This relates generally to cryptic metabolites, and more particularly, to a group of cryptic metabolites, and a genetics-free method for activating silent biosynthetic gene clusters in diverse microorganisms.

BACKGROUND

Modern medicine is unimaginable without natural products. Predominantly isolated from microorganisms and plants, these molecules, also referred to as secondary metabolites, form the basis of >70% of antibiotics, >50% of anticancer agents, and overall, more than half of the drugs approved in the United States in the past 35 years. After nearly a century of mining for secondary metabolites, microorganisms appeared to have become an exhausted resource. However, the recent explosion in microbial genome sequences points to a massive, untapped trove of new metabolites. Specifically, members of several bacterial phyla typically harbor 25 or more biosynthetic gene clusters (BGCs)—sets of genes that direct the biosynthesis of a natural product—that are not actively, or only weakly, expressed under standard laboratory conditions. These so-called "silent" or "cryptic" BGCs outnumber the constitutively active ones by a factor of 5-10. As such, finding new methods that access their products could significantly enhance our repertoire of novel natural products and thereby accelerate and aid drug discovery.

The importance of inducing silent BGCs has been recognized by the research community and several approaches have been developed to identify and characterize their small molecule products, including expression of BGCs in a heterologous host, co-culture screening, ribosome engineering, insertion of constitutive or inducible promoters, reporter-guided mutant selection, and endogenous overexpression of regulatory proteins. While these approaches have collectively begun to illuminate the hidden secondary metabolomes of bacteria, they all necessitate challenging culturing, molecular biology and/or genetic procedures, which significantly slow down the pace and throughput of natural products discovery. A definitive method for accessing cryptic metabolites in varied microorganisms has yet to be developed.

Thus, an inexpensive, reliable system for accurately detecting number of occupants in a given location is desirable.

SUMMARY OF INVENTION

The present disclosure is also drawn to a method for rapidly eliciting cryptic metabolites. The method requires providing multiple wells (for example, 96 wells) adapted for growing microorganisms, where each well contains at least one compound. Advantageously, the each of the compounds is a subset of a small molecule library. After growing microorganisms in each well, the wells are imaged with mass spectrometry, and differences between the imaged well and an imaged control well are identified. The compound(s) that elicited that difference are also identified. Advantageously, the mass spectrometry is laser-ablation electrospray ionization mass spectrometry (LAESI-MS). Also advantageously, the method also includes isolating a molecule, which may sometimes involve providing a culture comprising a second quantity of the medium (larger than used in the wells above) and at least one microorganism from the first species. The isolation process may then involve adding the identified compound(s) to the larger culture, growing the microorganism, and removing cells via, e.g., centrifugation. This isolation process may also include purifying via, e.g., HPLC. The molecule may also be characterized, which may include utilizing, for example, HPLC-ESI-MS or NMR. There is generally no restriction on the microorganism, although advantageously the microorganism is a gram-negative bacterium, a gram-positive bacterium, or a fungus, such as *Amycolatopsis* sp. B24117. In some instances, the genome sequence of the microorganism may not be known.

The present disclosure is drawn to a set of cryptic metabolites, or pharmaceutically acceptable salts thereof.

The present disclosure is also drawn to a method of utilizing the cryptic metabolites, inhibiting grown by contacting a microorganism with one of the cryptic metabolites. Advantageously, the microorganism may be a gram-positive bacterium, such as *Staphylococcus aureus, Streptococcus agalactiae, Streptococcus pyogenes, Streptococcus pneumoniae, Clostridium difficile, Enterococcus faecalis,* or *Bacillus subtilis*.

BRIEF DESCRIPTION OF DRAWINGS

FIG. 3 is a table of HR-MS data for orfamide A-B, canucin A-B, keratinimicin A-D, and keratinicyclin A-C.

FIG. 4D is an illustration of the topology of canucin A, with H12 and F13 providing steric locks.

FIG. 4E is an illustration that overlays of the top-10 computed structures for canucin A using NMR NOESY constraints and the CYANA algorithm, exhibiting a lasso topology.

FIG. 4F is an illustration that overlays of the top-10 computed structures for canucin B using NMR NOESY constraints and the CYANA algorithm, exhibiting a lasso topology.

FIG. 5A is a table of NMR assignments for canucin A in $CD_3OH$.

FIG. 7A is a table of NMR assignments for canucin B in $CD_3OH$.

FIG. 9B is a 2D component of the 3D plot focusing on keratinimicin A (m/z 1811) synthesis, highlighting that Dihydroergocristine (Dhe) and vincamine (Vin) were the most effective elicitors.

FIG. 9D depicts relevant NMR correlations used to solve the structures of keratinimicin A and keratinicyclin A.

FIG. 9H is a table annotating the keratinimicin biosynthetic gene cluster (ker).

FIG. 11A is a table of NMR assignments for keratinimicin A in DMSO-d6.

FIG. 13A is a table of NMR assignments for keratinimicin B in DMSO-d6.

FIG. 14A is a table of NMR assignments for keratinimicin C in DMSO-d6.

FIG. 15A is a table of NMR assignments for keratinimicin D in DMSO-d6.

FIG. 16A is a table of NMR assignments for keratinicyclin A in DMSO-d6.

FIG. 17A is a table of NMR assignments for keratinicyclin B in DMSO-d6.

FIG. 18A is a table of NMR assignments for keratinicyclin C in DMSO-d6.

FIG. 19 is a table showing MIC and $IC_{50}$ values (in μM) for keratinimicins and keratinicyclins against select pathogenic bacteria and viruses.

DETAILED DESCRIPTION

Figure 1:
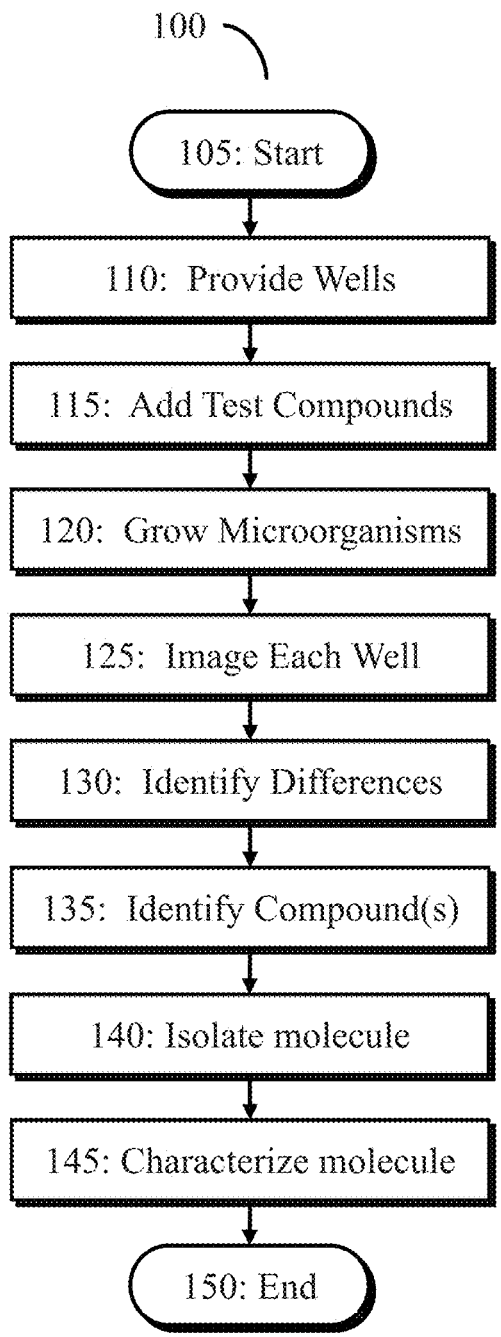
FIG. 1 is a flowchart describing an embodiment of the disclosed method.

Unless defined otherwise above, all technical and scientific terms used herein have the same meaning as commonly understood by one of ordinary skill in the art to which this invention belongs. Where a term is provided in the singular, the inventor also contemplates the plural of that term.

The singular forms "a", "an", and "the" include plural references unless the context clearly dictates otherwise.

The terms "comprise" and "comprising" is used in the inclusive, open sense, meaning that additional elements may be included.

Disclosed is an inexpensive and non-labor intensive method for rapidly eliciting cryptic metabolites.

Silent BGCs are a treasure trove for new secondary metabolites. Advances in DNA technology and extensive genome sequencing have compiled a massive genome database, which needs to be mined to harvest the fruits of decades of innovation. The ideal method to do so is one that does not necessitate challenging genetic or cloning procedures of the typically large BGCs. Moreover, the method should activate silent BGCs in a high-throughput fashion, preferably in an endogenous host, to avoid difficulties associated with heterologous expression. Lastly, a mono-culture approach is preferred to eliminate the possibility of irreproducible interactions that sometimes plague mixed- or co-culture screens. Disclosed is a method that satisfies all these criteria.

Its utility can be seen by, e.g., applying it to sequenced and unsequenced bacteria. For example, it can be applied to a rare actinomycete, members of which are difficult to manipulate genetically. The typical output of this approach is a picture of the global secondary metabolome of a given bacterium in response to ~500 conditions, which demonstrates activation of silent BGCs in a high-throughput fashion. Leveraging these advantages, disclosed is a lasso peptide with an unprecedented post-translational modification, new glycopeptide antibiotics with bioactivities similar to or better than those of vancomycin, and a novel glycopeptide chemotype, which combines features of the GPAs with those of the oxazolidinone antibiotics and exhibits better antiviral activity than the currently used drug ribivarin against RSV.

In contrast to primary metabolism, the complete secondary metabolome for any given prolific bacterium is not yet known. MALDI-TOF- and DESI-based IMS have been pioneered in assessing bacterial cultures or interspecies interaction, but the use of IMS in interrogating cryptic metabolomes in response to hundreds of conditions has not yet been reported. Thus, in addition to unearthing novel cryptic metabolites, disclosed is a high-throughput elicitor screening (HITES)-IMS method that may be used to delineate global secondary metabolomes, that is, the full synthetic capacity of selected bacterial species. The advantage of this approach is that the final product of a BGC, the secondary metabolite, provides the read-out, rather than transcriptional or translational assays. Additionally, by linking new cryptic metabolites to an elicitor, the mechanism of elicitation may be investigated, which in turn can identify regulatory circuits that kick-start secondary metabolism in response to sub-inhibitory concentrations of toxins. The disclosed approach is the most general so far for activation of silent BGCs, and it is poised to simultaneously shed light onto the products and regulation of cryptic metabolism in diverse bacteria.

Referring to FIG. 1, methods for rapid eliciting cryptic metabolites (100) generally begin by introducing a microorganism and growth medium into a series of wells (110). Generally speaking, an array of wells is preferred. In certain embodiments, 48-, 96-, 384-, or 1536-well cell culture plates are utilized. In certain embodiments, arrays of more than 1500 wells are utilized. More preferred embodiments utilize between 50 and 500 wells.

Each well must contain a microorganism, and, typically, a medium adapted for growing that microorganism.

Although any microorganism may be utilized, in preferred embodiments the microorganism is a species of bacteria or fungi. In preferred embodiments, the microorganism is a gram-negative bacterium, a gram-positive bacterium, or a fungus. Note that in certain embodiments, genome sequences of the microorganism are not known. In fact, no genetic procedures are necessary to utilize the disclosed method. Further, the method is not limited to microorganisms in which genetic procedures are established. Certain embodiments use microorganisms that cannot be genetically manipulated, which may include rare actinomycetes, new strains where genetic manipulations are not yet available, and bacterial mixtures or consortia.

There are no restrictions on which medium can be used; any desirable medium may be utilized in the wells.

Typically, at least one of the wells is used as a control, and the remainder of which are used as test wells. In each test well one or more additional compounds will be added. In some embodiments, each of the compounds added to a test well are part of a small molecule library. Referring back to FIG. 1, once the wells, with the medium and microorganisms are provided, test compounds are added (115). In these methods, typically one wells is considered a "control" well, and does not contain any test compounds. Other wells may contain one or more test compounds in addition to the microorganism and medium.

There is no restriction on what test compounds can be utilized. In some embodiments, the test compounds may include an antibiotic or other compound known to be inhibitory to growth of the microorganism. In preferred embodiments, each of the at least one compounds is a subset of a small molecule library. In certain embodiment, a portion of the wells utilize two or more test compounds.

The microorganisms are then grown in each well (120). The exact conditions for growth will be based on numerous factors, known to those of skill in the art.

In one example, $P.$ $protegens$ was streaked out onto an LB-agar plate from frozen culture stocks and grown at 30° C. overnight. Colonies were used to inoculate 5 mL of LB in a 14 mL sterile culture tube, which was cultured 12-13 h at 30° C./250 rpm. The overnight culture was then used to inoculate 550 mL LB in a sterile Erlenmeyer flask to an initial optical density at 600 nm ($OD_{600\ nm}$) of 0.01. The culture was distributed into six sterile, deep-well 96-well plates (0.9 mL per well) using a MultiFlo Microplate Dispenser (BioTek). Subsequently, elicitors were added from a commercially-available 502-member natural products library (Enzo Scientific, cat #BML-2865) using a CyBi-Well automated liquid transfer robot (CyBio). Each well received 2.5 µL of an elicitor (from a stock concentration of 10 mM). The plates were sealed with air-permeable membranes and grown at 25° C./200 rpm. After 44 h, the plates were spun down, supernatants loaded onto a 96-well Strata C8-resin (Phenomenex), and the material eluted with 600 µL of 50% and 600 µL 100% MeCN into fresh 96 well plates. The eluates were then dried in a speedvac and resuspended in 30 µL of 40% MeCN (in water).

In other examples, freshly-collected spores of $S.$ $canus$ or $A.$ $keratiniphila$ (~$10^7$) were transferred to 50 mL YEME medium (3% (w/v) yeast extract, 5% peptone, 3% malt extract, 1% glucose, 34% sucrose, and 5 mM $MgCl_2.6H2O$) in a 250 mL Erlenmeyer flask fitted with a stainless-steel spring and cultured at 30° C./250 rpm for 3 days. Mycelia were then collected by centrifugation (10 min, 3000 g, RT) and diluted into 300 mL of R4 medium to give a final concentration of 0.05% (w/v). R4 medium[1] consisted of 0.5% (w/v) glucose, 0.1% yeast extract, 0.5% $MgCl_2.6H2O$, 0.2% $CaCl_2.2H_2O$, 0.15% proline, 0.118% valine, 0.28% TES, 50 mg/L casamino acid, 100 mg/L $K_2SO_4$, and 1× trace element solution, which contains 40 mg/L $ZnCl_2$, 200 mg/L $FeCl_3.6H2O$, 10 mg/L $CuCl_2.2H2O$, 10 mg/L $MnCl_2.4H_2O$, 10 mg/L $Na_2B_4O_7.10H_2O$, and 10 mg/L $(NH_4)_6Mo_7O_{24}.4H_2O$). Subsequently 300 µL were dispensed into six deep-well 96-well plates using a MultiFlo Microplate Dispenser. The wells were supplemented with candidate elicitors from the same 502-member natural products library used above with the aid of a CyBi-Well automated liquid transfer robot. Each well received 0.85 µL of an elicitor (from a stock concentration of 10 mM). The plates were sealed with air-permeable membranes and grown at 30° C./250 rpm. After 5 days, the samples were desalted as described above for $P.$ $protegens$.

Once the microorganisms have grown in each well, the metabolome that results in response to each molecule from the library, is determined rapidly using at least one imaging mass spectrometry technique. In certain embodiments, the mass spectrometry technique is laser-ablation electrospray ionization mass spectrometry (LAESI-MS).

Each well is imaged (125), and differences are identified (130) between that image and the image from a control well.

The test compounds correlating to one or more of differences is then identified (135). In certain embodiments, each of these three steps occurs for the entire array of wells before moving to the next step. That is, all images are taken, then differences are determined for all wells, then any test compounds eliciting those differences are identified. In other embodiments, the images for a first well is taken, it is compared to the image from the control well, and if there is a difference, the compound associated with that well is identified. Then the image for a second well is taken, and the process repeats until all wells have been completed. Other approaches may also be advantageous, depending on the exact needs and configuration of the system.

Imaging of the wells is typically done per manufacturer instructions. To identify differences, typically software is used to analyze the collected images, searching for mass ions that were induced by elicitors and absent in untreated samples.

In one example, a laser ablation electrospray ionization (LAESI) DP1000 system (Protea Bioscience) coupled to a LTQ XL mass spectrometer (Thermo) was used for IMS analysis. The extension tube connecting the two instruments was kept at 130° C. with an external heater and the sample stage was kept at 10° C. during analysis. Sheath gas flow was set to 2.0 L/h. Eighty laser pulses were applied to each well to ablate samples using an 80% laser energy setting (~850 µJ) and a 10 Hz frequency. A solution of 2:1 MeCN/water with 0.1% acetic acid (v/v) was supplied as the electrospray solution by a syringe pump running at a flow rate of 1 µL/min. The emitter was connected to high voltage power operating at +4000V or +4500V in positive ion detection mode. All data were visualized in ProteaPlot software.

Once the differences are known, the test compound(s) can be identified, typically via comparing some identification information describing the well or compound added to the well with data in a database or lookup table, using a computer or dedicated processor. This can be done manually or automatically. Preferably, only the best few elicitors are identified, typically no more than the top 4-5 elicitors.

In one example, after data collection, the signals observed in each well were extracted using GMSU-LAESI software (Gubbs, Inc), which gave all m/z values and the corresponding intensities per well (i.e. per elicitor). The data were binned in 1 m/z units for 3D-plotting. Signals with an intensity lower than a set threshold were not included in the 3D plots. The data were plotted in MatLab using the bar3 function. The component 2D plots were extracted from the corresponding 3D data in MatLab and plotted in Excel. The 2D plots were normalized to the highest intensity peak. Each signal was correlated with an elicitor.

Figure 20:
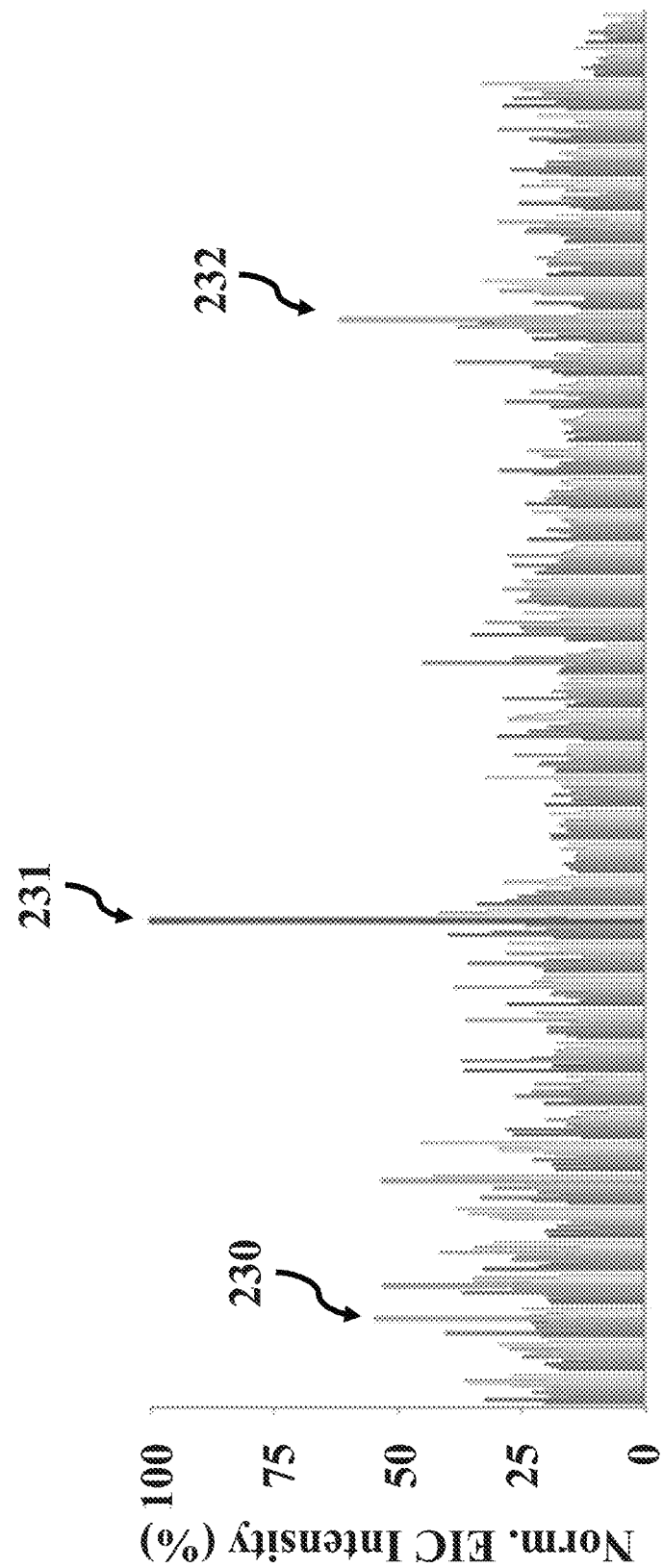
FIG. 20 is one embodiment of a 2D component of a 3D plot from a high-throughput elicitor screen using LAESI-MS detection.

In another example, to commence a screen, *Amycolaptopsis* sp. B-24117 spore stocks were used to inoculate 100 mL of R4 medium in a 500 mL Erlenmeyer flask (approx. $10^6$ spores). These were grown overnight and then dispensed into 5×95 CORNING® COSTAR® 96 well cell culture plates using a BioTek MULTIFLO™ microplate dispenser. 150 µL was dispensed into each well, which were then supplemented with each 1 µL from the Natural Products small molecule library (Enzo Scientific). The plates were grown again at 30° C. and 250 rpm for 4 days before being imaged using a Laser Ablation Electrospray Mass Spectrometer (LAESI-MS), which consisted of a Protea Biosciences LAESI® DP-1000 module coupled to a THERMO SCIENTIFIC™ LTQ mass spectrometer. Imaging of each plate was conducted as per manufacturer instructions using 1:1 MeCN/water at a flow rate of 1 µL/min to ablate the samples into the mass spectrometer. The spectrum was collected for 8 seconds per well. The data were then analyzed using ProteaPlot software, searching for mass ions that were induced by elicitors and absent in untreated samples. Referring to FIG. 20, this led to identification of a mass ion (reference 230, m/s 1810, keratinimicin A). The best elicitors were determined to be tryptanthrin (231) and dihydroergocristine (232) at a concentration of 30 µM each.

In some embodiments, the identification of the elicitors is sufficient. In other embodiments however, the elicited molecule may also be isolated (140).

To isolate the molecule (140), one method is to utilize a larger culture, comprising a quantity of a medium that is larger than the quantity used in the well, and the target microorganism. At least one of the identified elicitors is then added to the larger culture. The microorganism is then grown in the precise of the elicitor, and the cells and the molecules are then separated. Typically, the cells are removed via centrifugation, although other approaches may be acceptable, depending on the exact needs of the system. The output may further be purified using typically purification techniques, including but not limited to using HPLC. The molecule may also be characterized (145). In some embodiments, the characterization is done using HPLC-ESI-MS or NMR, although other methods may also be utilized.

Replacing Genetics with Imaging Mass Spectrometry. The HiTES approach consists of two components, the activation of silent or lowly-expressed BGCs by elicitor screening and a read-out for this process, which so far has relied on genetic reporter assays. The detection step limits the throughput of HiTES as creating the appropriate genetic constructs is often time-consuming, if not impossible, depending on the strain. To avoid this drawback, the workflow may consist of subjecting the wt microorganism to elicitor screening followed by imaging the resulting, e.g., 500-1000 metabolomes, as a function of each molecule in the library, using IMS.

For example, in one embodiment of a HiTES-IMS workflow, a bacterial culture is arrayed into 96-well plates and subjected to high-throughput elicitor screening. After a suitable incubation period, the cultures are assessed by LAESI-IMS in 96-well format. The observed global metabolome is depicted in a 3D plot that links each elicitor to metabolites, characterized by their m/z and MS intensity values. Large scale cultures with the elicitor facilitate isolation and characterization of new cryptic metabolites.

Computational approaches and appropriate visualization can then be used to pinpoint cryptic metabolites.

Figure 2A:
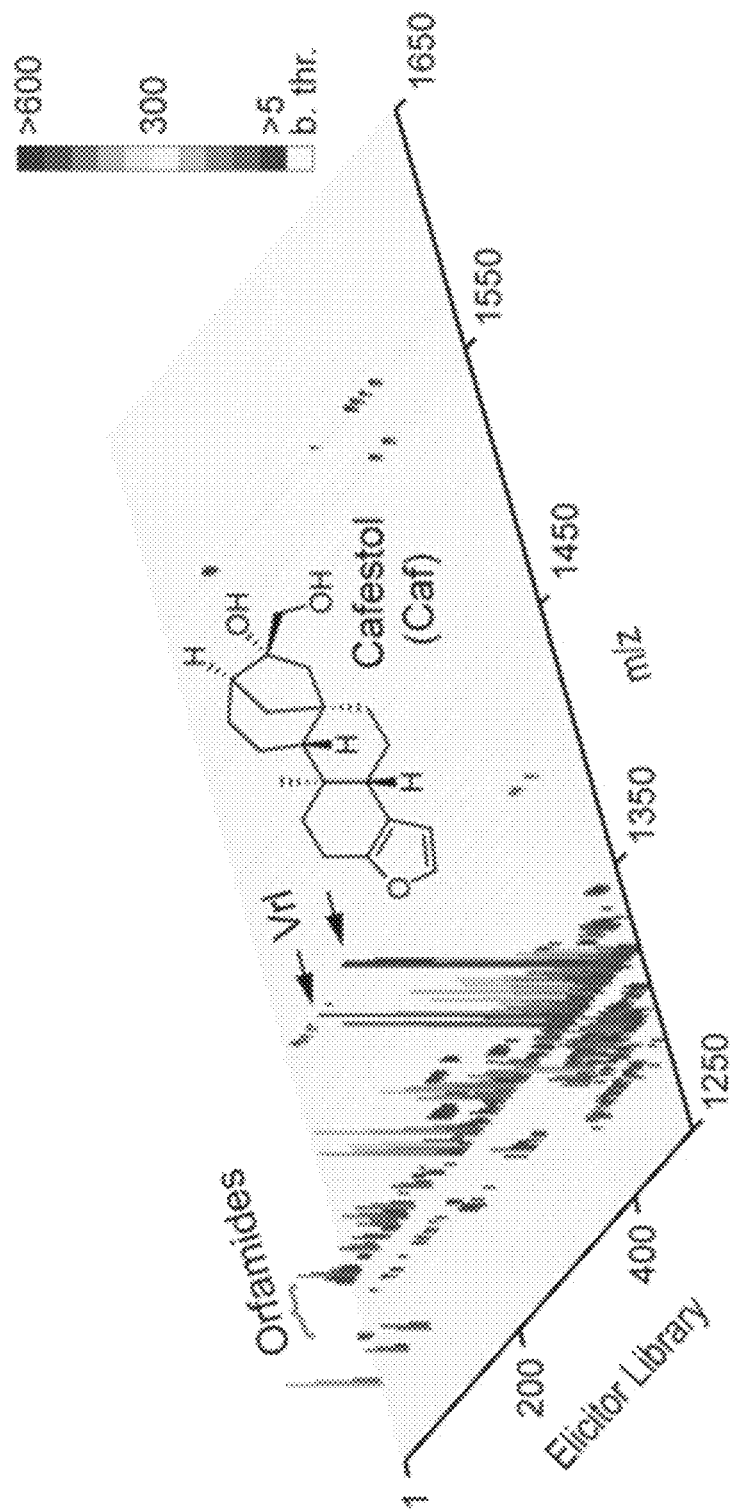
FIG. 2A is a 3D plot relating the *P. protegens* metabolome, in terms of m/z and MS intensity, to each elicitor.
Figure 2B:
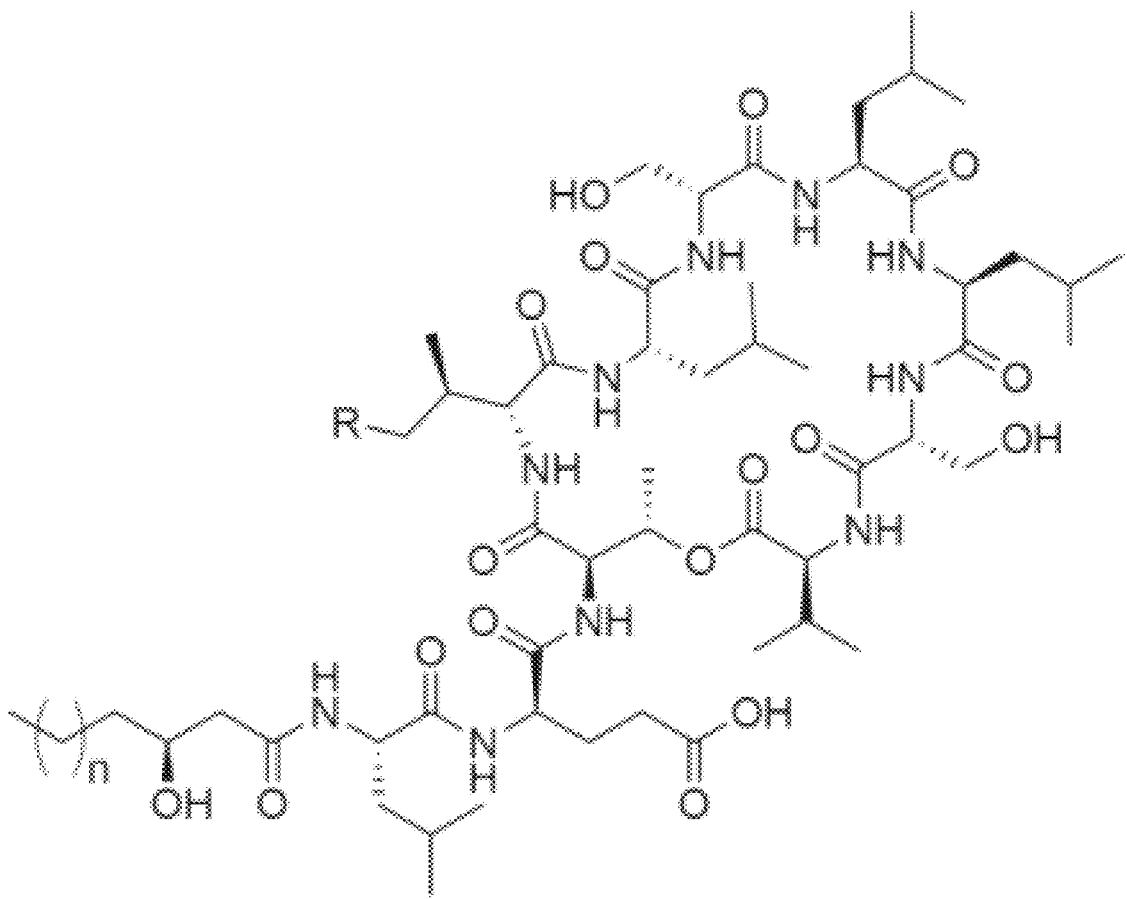
FIG. 2B is an illustration of the structures of orfamide A and B.

As another example, Orfamides are lowly-expressed metabolites isolated from *Pseudomonas protegens* Pf-5 (hereafter *P. protegens*). A genome-isotopic approach was previously used to identify and ultimately solve their structures. Wt *P. protegens* was cultured in 96-well plates and subjected to HiTES using a 502-member natural products library. The resulting metabolomes were analyzed using laser ablation-coupled electrospray ionization MS (LAESI-MS), an emerging method in which a mid-IR laser beam generates an ablation plume of metabolites that are ionized by an electrospray and introduced into the mass spectrometer. Compared to other IMS methods, the advantage of LAESI-MS is that it can be applied to liquid or solid surfaces and live bacterial cultures with minimal sample preparation at ambient pressure. Optimization of numerous parameters facilitated rapid characterization of the metabolome within each of the 502 wells, allowing us to image a 96-well plate liquid culture in less than an hour. The data were rendered in a 3D plot depicting the intensity and m/z for each metabolite induced by a given elicitor (See FIG. 2A). In this example, MS data were collected in the m/z range of 1200-2000 to focus on orfamide production, in response to a 502-member natural products library. No signals were detected below m/z 1250 and above m/z 1650. MS intensity was color-coded, and signals that were below the 5-count threshold were identified, and which were therefore not included in the plot. Orfamides were labeled, as were the best elicitors of orfamide synthesis, cafestol (Caf) and vinorelbine (Vrl). FIG. 2B indicates the structures of orfamide A and B.

Figure 2C:
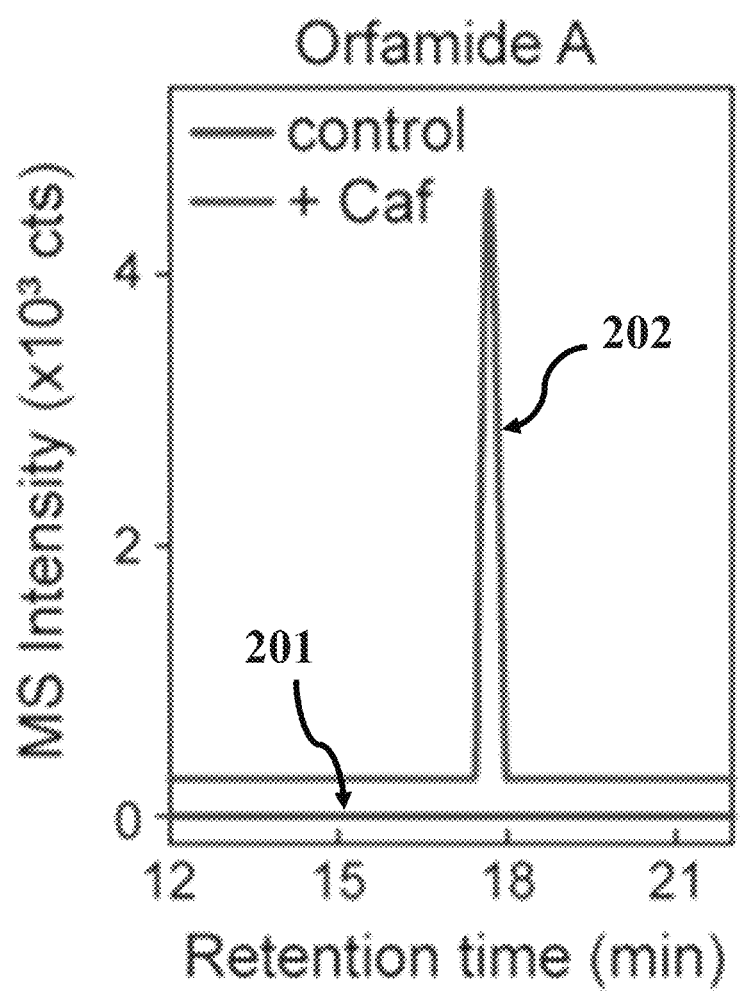
FIG. 2C is a graph of the HR-MS extracted ion chromatogram of orfamide A from untreated and Caf-treated cultures, where the traces are offset for clarity.

By computationally inspecting the amalgamated 502 metabolomes, one of skill in the art can easily see induction of orfamides—specifically analogs A, B, and several unknown derivatives—to varying degrees. Optimal production was triggered by the mild cytotoxin cafestol and the anticancer agent vinorelbine, compounds previously not known to elicit secondary metabolism. Cafestol's stimulatory activity was further confirmed using HPLC-MS, thus validating the use of HiTES-IMS in inducing silent or lowly-expressed BGCs (See FIGS. 2C, 3). FIG. 2C is a graph validating Caf as an inducer of orfamide A in flask cultures. FIG. 2 shows a HR-MS extracted ion chromatogram of orfamide A from untreated (201) and Caf-treated (202) cultures. FIG. 3 is a table showing HR-MS data for orfamide A-B, canucin A-B, keratinimicin A-D, and keratinicyclin A-C.

The simplicity of this approach allow it to be broadly applied.

Figure 4A:
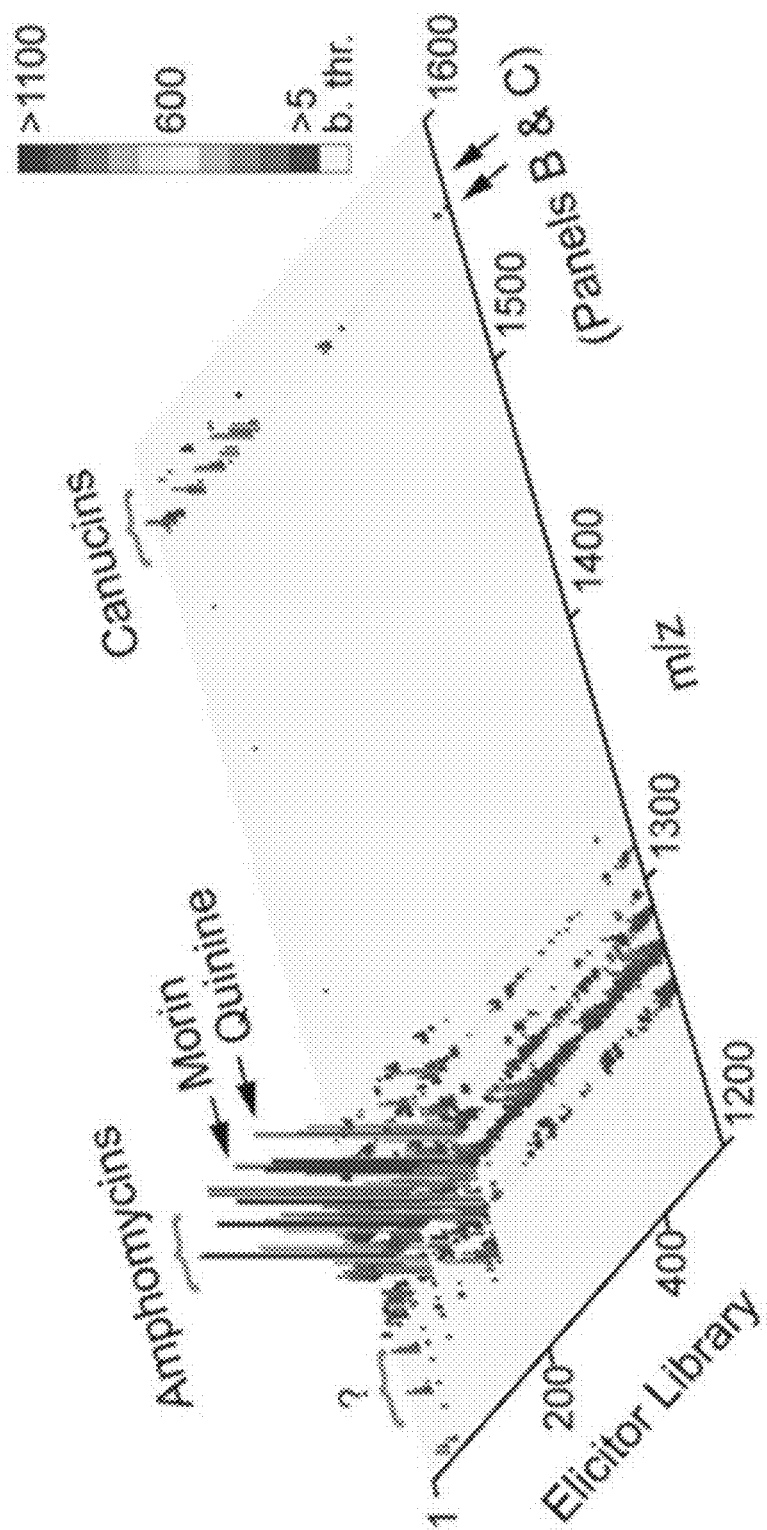
FIG. 4A is a 3D plot relating a secondary metabolome of *S. canus*, in terms of m/z and MS intensity, to 502 elicitors.
Figure 4B:
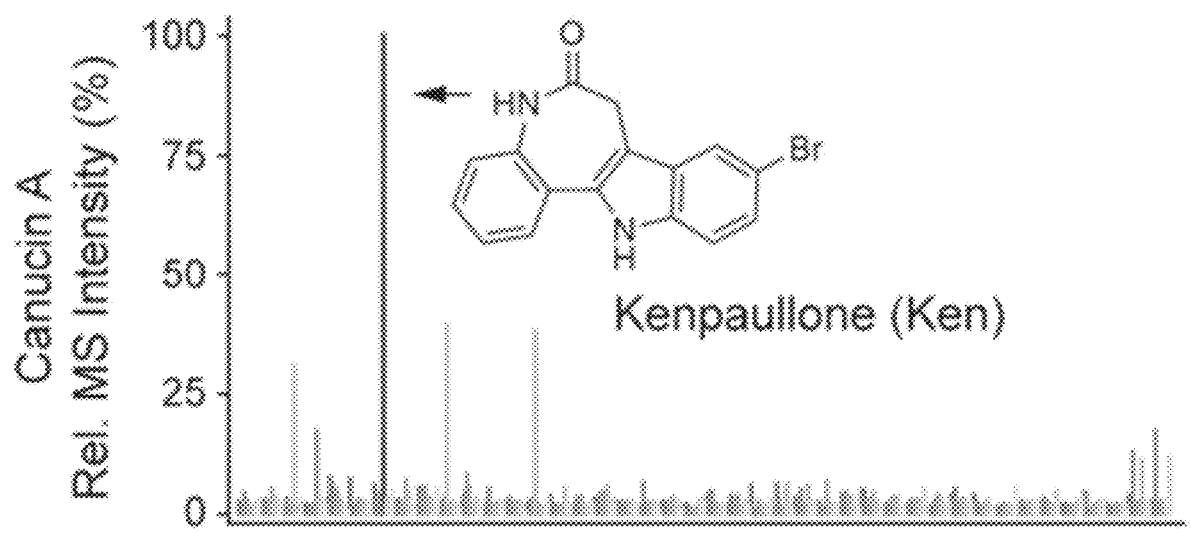
FIG. 4B is a 2D component of the 3D plot focusing on canucin A (m/z 1579) synthesis, highlighting that Kenpaullone was the most effective elicitor.

Application of HiTES-IMS to *Streptomycetes*. The HiTES-IMS method was also applied to *Streptomyces* spp., the most prolific genera of bacterial secondary metabolite producers known. *Streptomyces canus* NRRL B3980 was chosen, which is related to the amphomycin producer and contains over 20 BGCs that have not been linked to a natural product. The results of HiTES-IMS with *S. canus* using again a 502-member natural products library are shown in 3D representation. (See FIG. 4A) An m/z range of 1000-2000 was used to simplify the MS output and at the same time optimize chances for finding new metabolites. Three clusters of peaks, representing three compound families appeared to be elicited: compounds were detected with m/z ranging from 1260-1295, which further analysis identified as the amphomycins. The best elicitors for the amphomycins were the flavonol morin and the antimalarial quinine. A second set of induced compounds was also detected with m/z ranging from 1220-1245. Finally, induction of a third compound family was observed, distinct from the other two, with m/z of 1563 and 1579 elicited by the cyclin-dependent kinase inhibitor kenpaullone (See FIGS. 4A, 4B). FIG. 4B is 2D component of the 3D plot focusing on canucin A (m/z 1579) synthesis. In this example, Kenpaullone was the most effective elicitor. These findings highlight the ability of the disclosed approach to induce multiple cryptic BGCs in a parallel fashion. The current approach provides the ability to monitor all BGCs that can be captured by the detection method in one experiment.

Figure 4C:
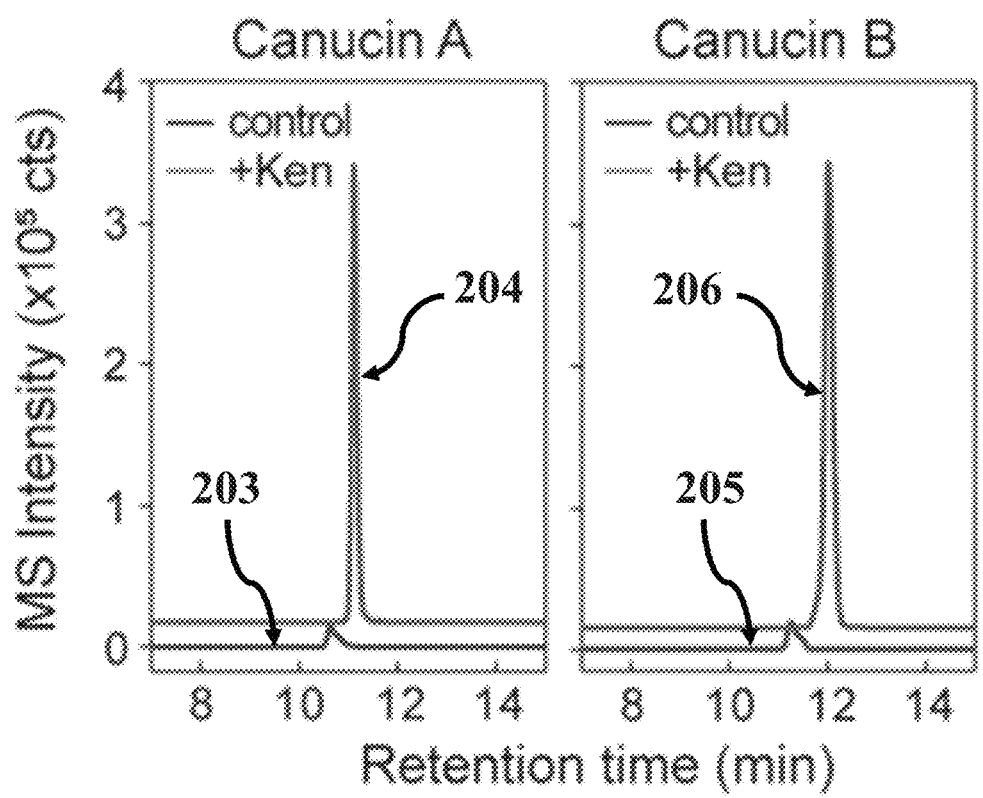
FIG. 4C depicts graphs of the HR-MS extracted ion chromatogram of canucin A (left) and B (right) by Ken in flask cultures, where the traces are offset for clarity.

From the cryptic metabolites elicited in this example, further efforts were focused on the compounds with m/z 1579 and 1563, which were assigned the trivial name canucin A and B, respectively (See FIG. 3). The results were validated by observing 96-well plates and finding strong induction of both compounds by kenpaullone (FIG. 4C). In FIG. 4C, induction of canucin A and B by Ken in flask cultures is shown, highlighting the untreated (203, 205) and Ken-treated (204, 206) cultures The traces are offset in the X- and Y-axes for clarity.

Figures 5B, 5C:
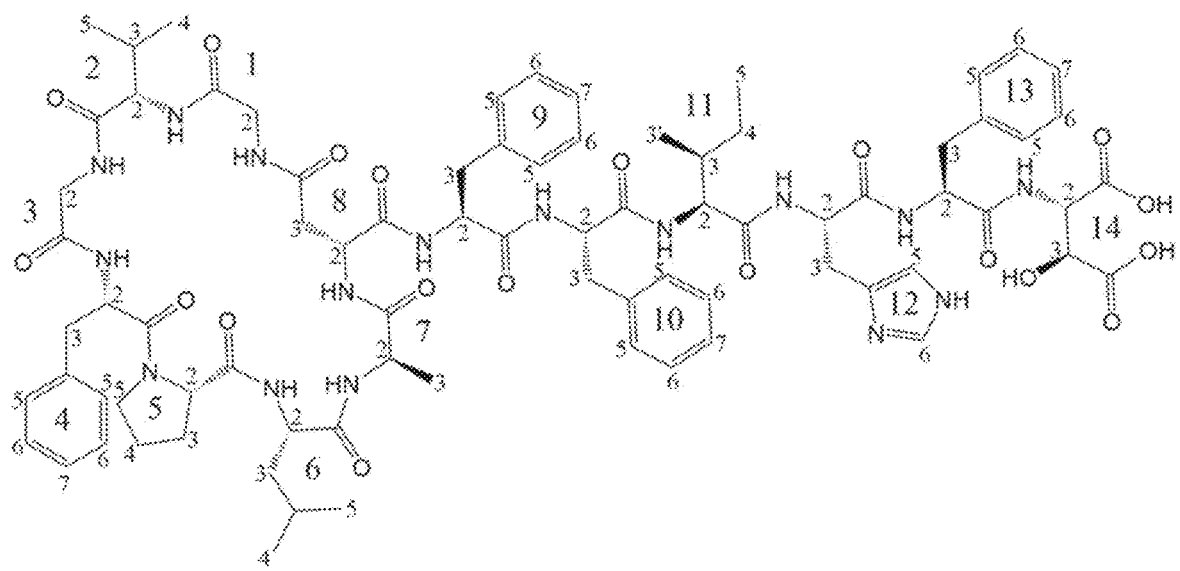
FIG. 5B is an illustration showing the numbering scheme for canucin A.
FIG. 5C is a table summarizing the CYANA-derived parameters from calculations of R and S stereoisomers at the Cβ of Asp14 in canucin A.

Large-scale production cultures with kenpaullone as inducer allowed us to isolate sufficient material to solve the structures of canucins by 1D/2D NMR. Analysis of $^1$H, gCOSY and TOCSY NMR showed that canucin A was a peptide with 14 recognizable α-$^1$Hs. HSQC and HMBC analysis revealed 13 of these as canonical amino acids, while one was the modified β-hydroxy-Asp (See FIGS. 5A-5B). FIG. 5A shows NMR assignments for canucin A in CD$_3$OH. The numbering scheme for canucin A is shown in FIG. 5B.

Figure 6A:
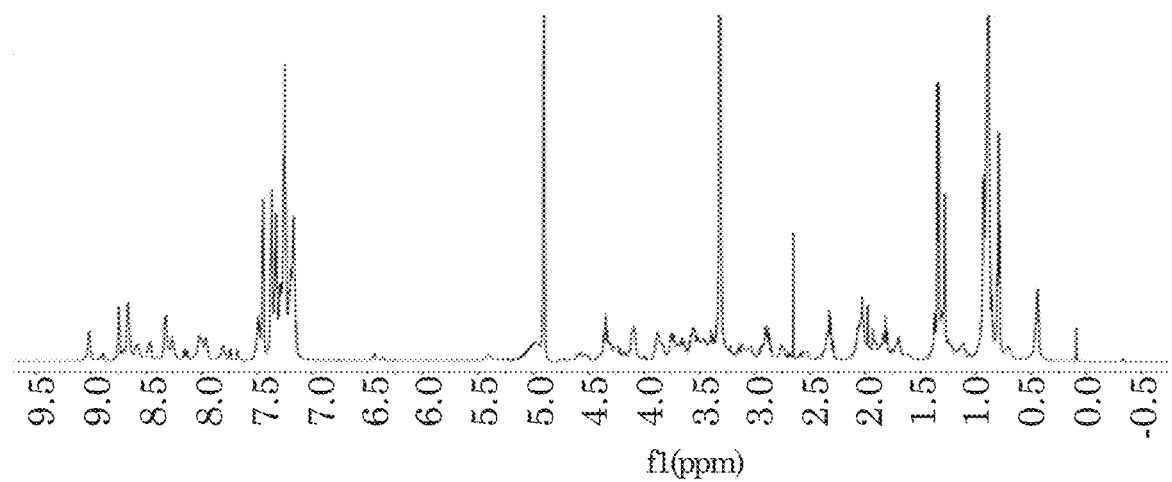
FIGS. 6A-6E are NMR spectra of canucin A in $CD_3OH$, including $^1H$ NMR (FIG. 6A), TOCSY (FIG. 6B), NOESY (FIG. 6C), HSQC (FIG. 6D) and HMBC (FIG. 6E).
Figure 6B:
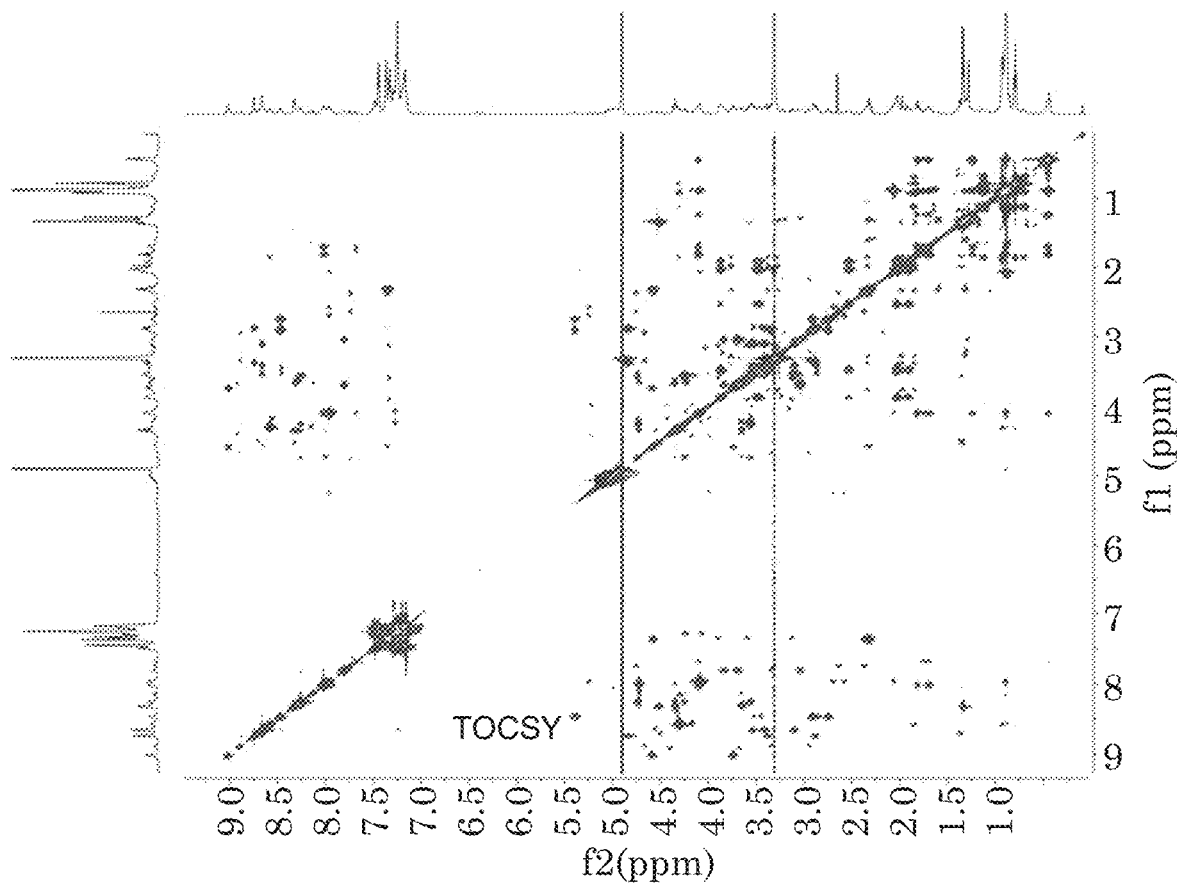
Figure 6C:
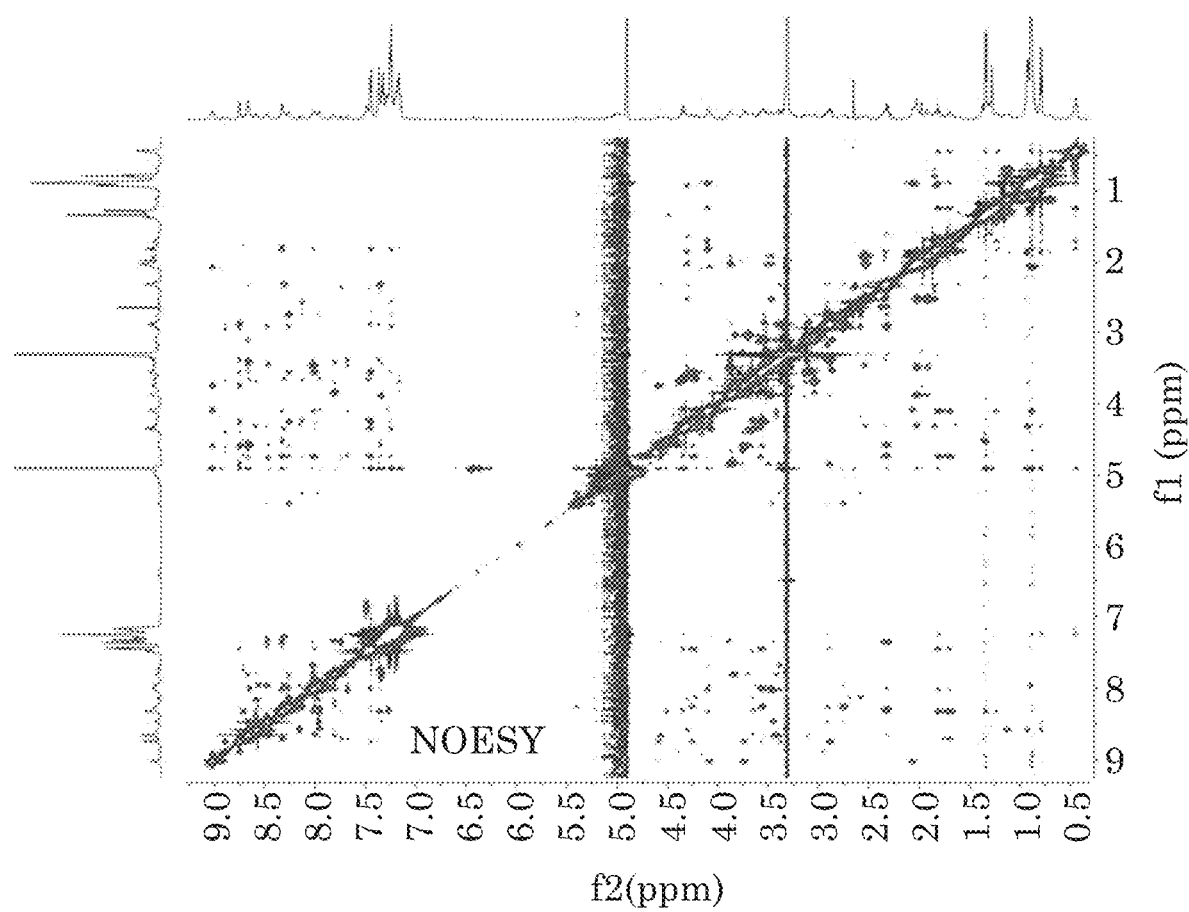
Figure 6D:
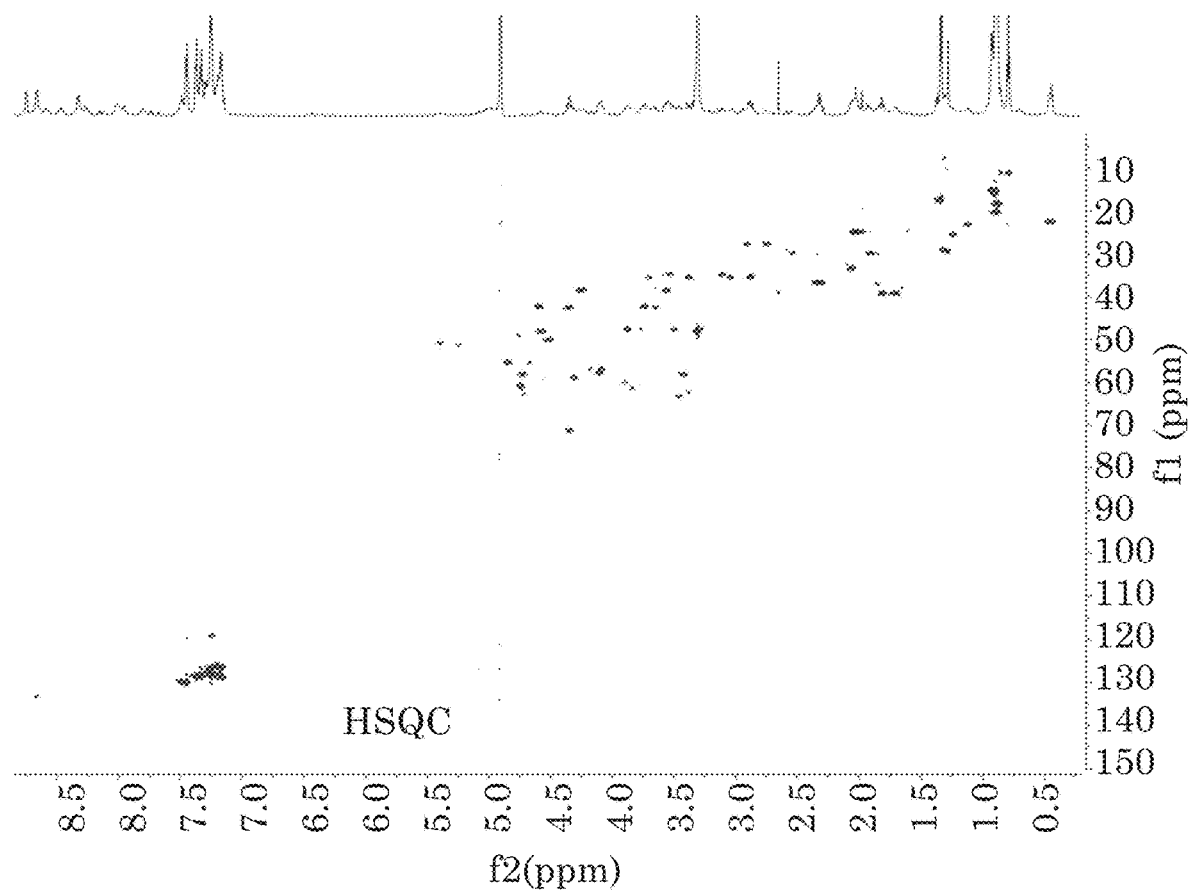
Figure 6E:
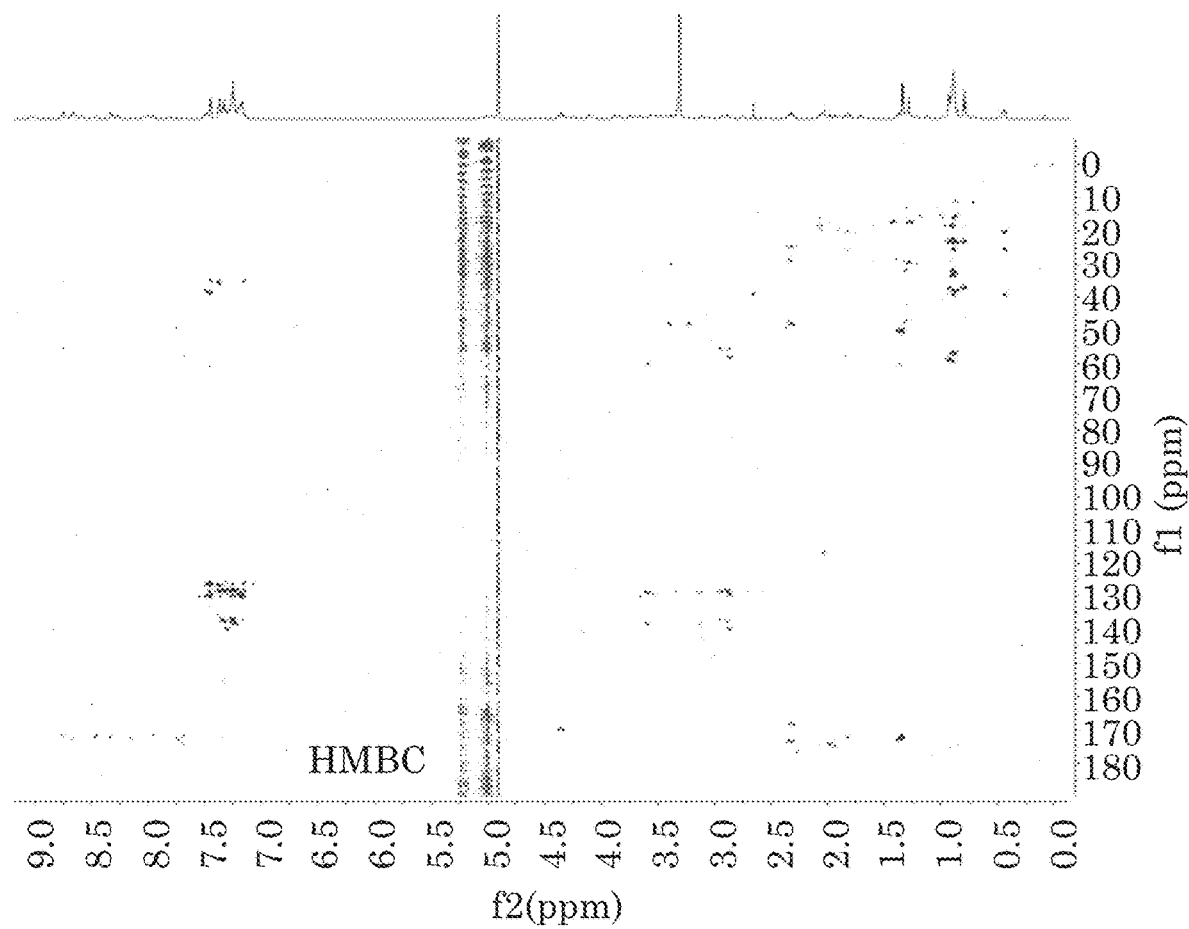

Further analysis by NMR and HR-MS suggests that canucin A harbors an isopeptide bond between residues Gly1 and Asp8, a feature that is typical for lasso peptides. Indeed, NOESY correlations between the C-terminal tail residues and those surrounding the isopeptide bond suggested that canucin A contained a lasso topology (See FIGS. 6A-6E). FIGS. 6A-6E provide NMR spectra of canucin A in CD$_3$OH, including $^1$H NMR (FIG. 6A), TOCSY (FIG. 6B), NOESY (FIG. 6C), HSQC (FIG. 6D) and HMBC (FIG. 6E). To verify, high-resolution NOESY spectra were collected with various mixing times and solved the 3D structure of canucin A using the CYANA algorithm, which utilizes molecular dynamics simulations in a peptide's torsion angle space to compute structures that agree best with the NOESY data. The ten best structures converge on a lasso topology, in which His12 and Phe13 provide steric locks above and below the ring, respectively (FIGS. 4D, 4E). FIG. 4D provides an Illustration of the topology of canucin A, with H12 and F13 providing steric locks. FIG. 4E shows an overlay of the top-10 computed structures for canucin A and B using NMR NOESY constraints and the CYANA algorithm. Both exhibit a lasso topology. At 14 amino acids, canucin A is one of the smallest lasso peptides discovered to date. See FIG. 5B.

Repeated efforts to determine the stereochemistry at the β-carbon of the C-terminal Asp by Mosher analysis failed, possibly due to steric hindrance. Subsequently CYANA was used to calculate which stereoisomer best fits the observed NOESY correlations. The S-stereoisomer gave a lower f-function, indicative of a better match between the calculated structure and the set of constraints, as well as a lower backbone-rmsd (See FIG. 5C). FIG. 5C is a summary of CYANA-derived parameters from calculations of R and S stereoisomers at the Cβ of Asp14 in canucin A.

Figures 7B, 8:
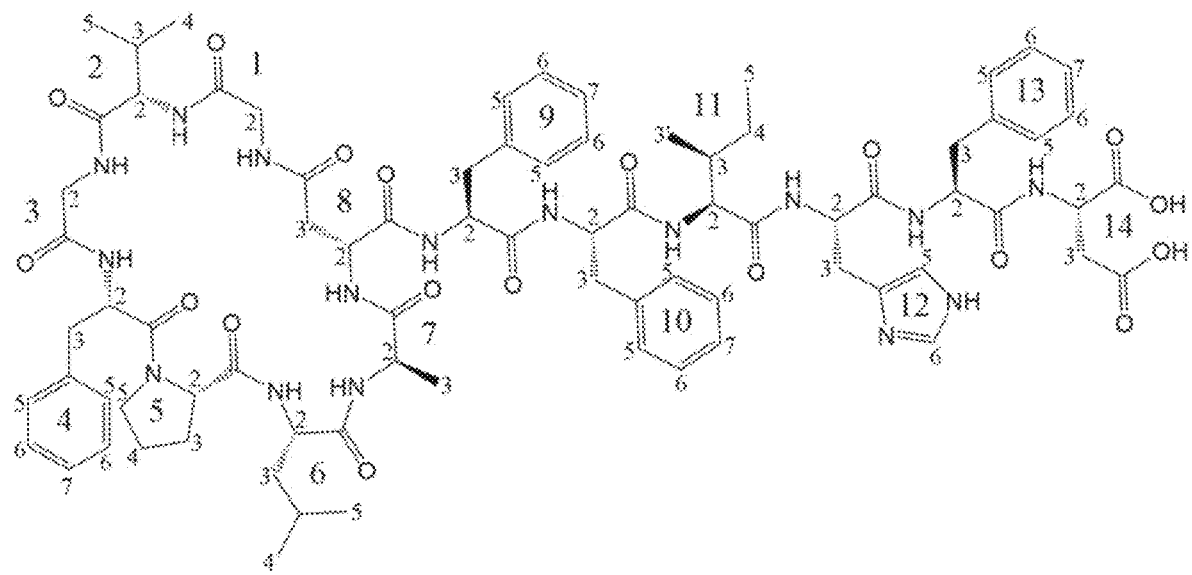
FIG. 7B is an illustration showing the numbering scheme for canucin B.
FIG. 8 is a table annotating the canucin biosynthetic gene cluster (can).

The S-stereo configuration at the β-carbon of Asp is suggested. A second analog, canucin B, is also identified. Structural elucidation by HR-MS and NMR identified it as the des-hydroxy variant of canucin A (See FIGS. 3, 7A, 7B). FIG. 7A provides NMR assignments for canucin B in CD$_3$OH, while FIG. 7B illustrates the numbering scheme for canucin B.

CYANA calculations confirmed that canucin B harbors a lasso topology, again revealing His12 and Phe13 as steric locks in a topology akin to that of canucin A (See FIG. 4F). These results suggest that hydroxylation at the C-terminal Asp in canucin A occurs after the threaded lasso motif has been installed.

Figure 4G:
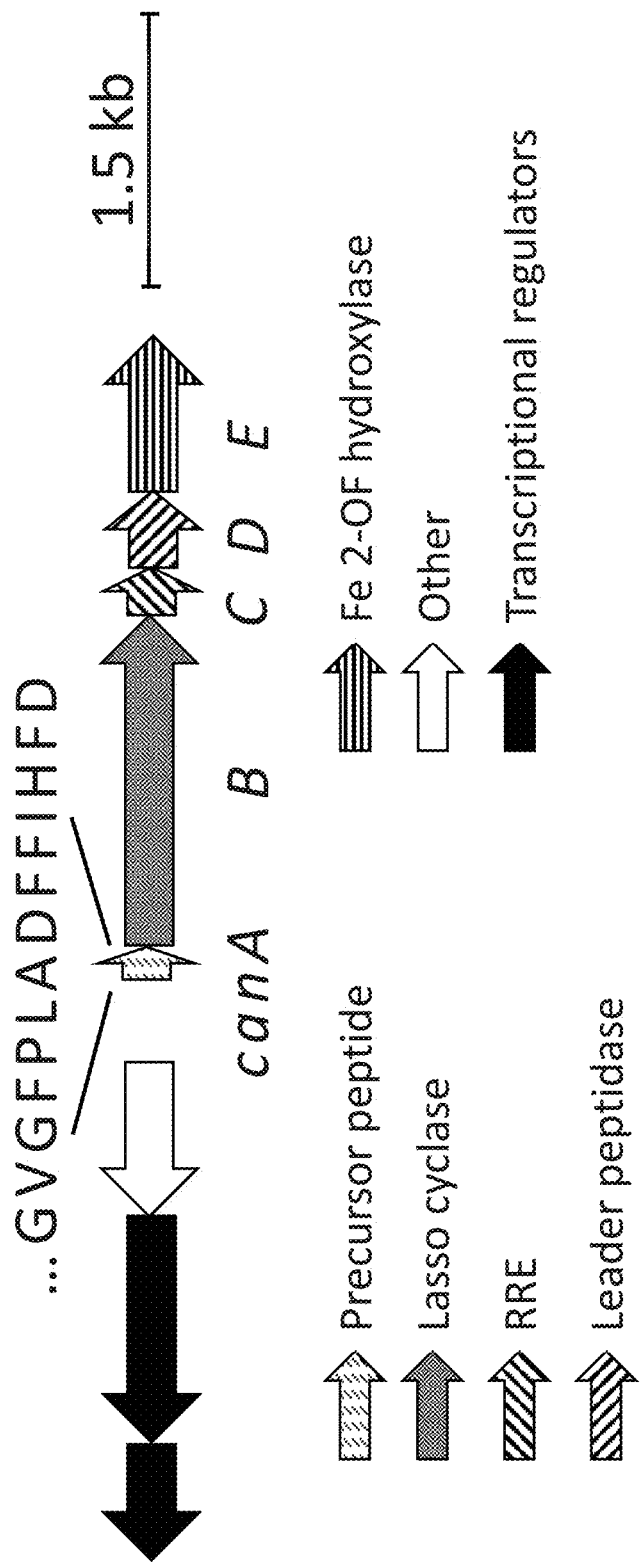
FIG. 4G is a depiction of BGC for canucins (can) as identified by bioinformatic studies. The C-terminal sequence of CanA is shown along with predicted functions of the tailoring enzymes.

Post-translationally modified lasso peptides are rare, and a β-hydroxylated amino acid has never been observed within this compound family. To gain insights into the biosynthesis of canucin A, the genome sequence of *S. canus* were examined. A BGC was identified, which was annotated as can, with a typical lasso peptide synteny and a precursor peptide, whose C-terminal sequence (GVGFPLADFFIHFD (SEQ ID NO. 001)) perfectly matched that of the canucins (FIG. 4G).

Aside from the precursor peptide, the can BGC contains a typical protease and an Asn synthetase, which respectively remove the precursor peptide and form the threaded lasso motif. In addition, canE was annotated, encoding an α-KG-dependent mononuclear Fe enzyme, members of which have been shown to hydroxylate unactivated carbon positions. (See FIG. 8). FIG. 8 provides annotation of the canucin biosynthetic gene cluster (can). CanE is likely involved in the synthesis of β-OH-Asp. The discovery of canucins shows that HiTES-IMS can be applied to streptomycetes to unveil new cryptic metabolites.

Figure 9A:
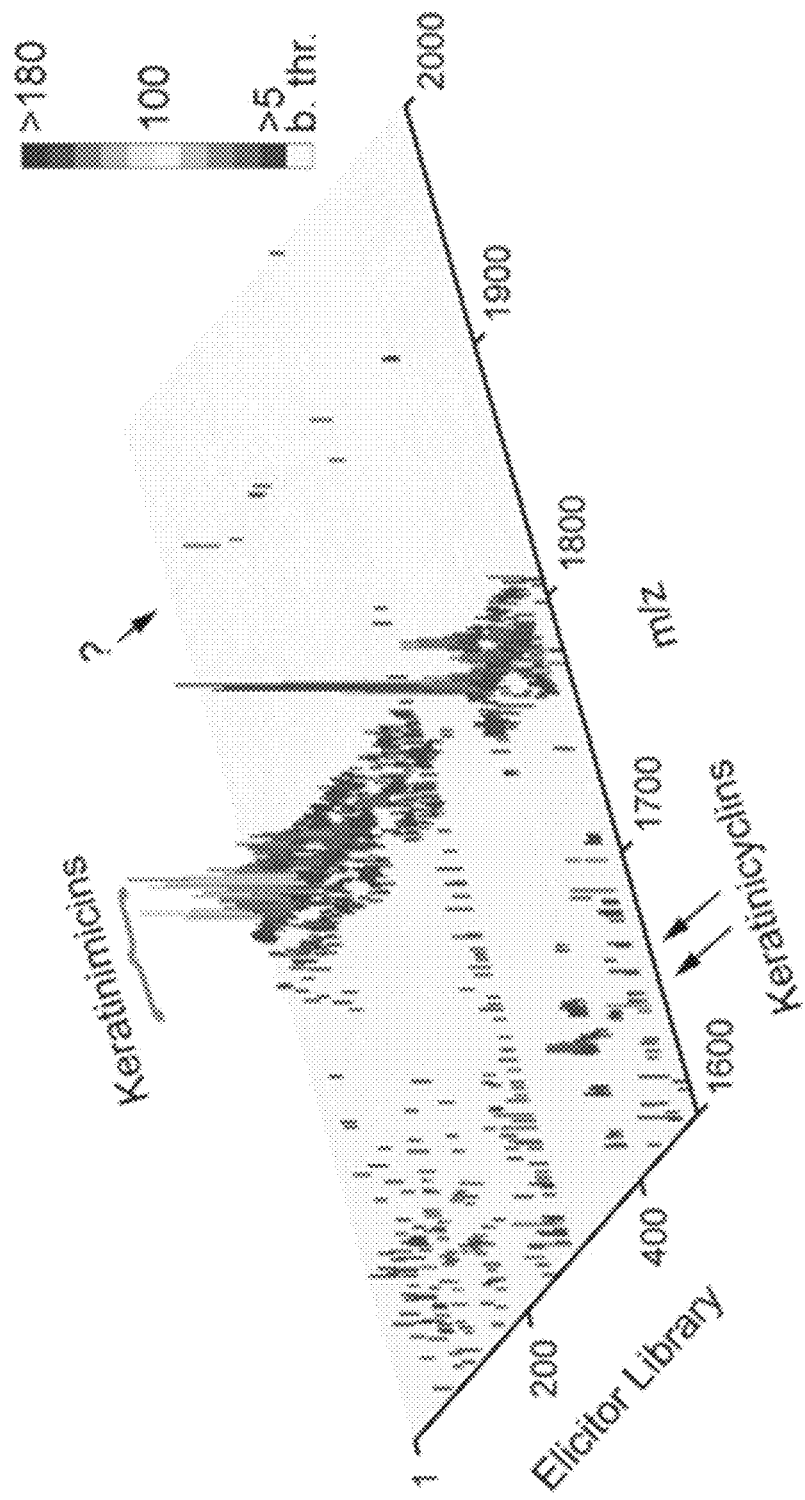
FIG. 9A is a 3D plot relating a secondary metabolome of *A. keratiniphila*, in terms of m/z and MS intensity, to 502 elicitors.
Figure 10A:
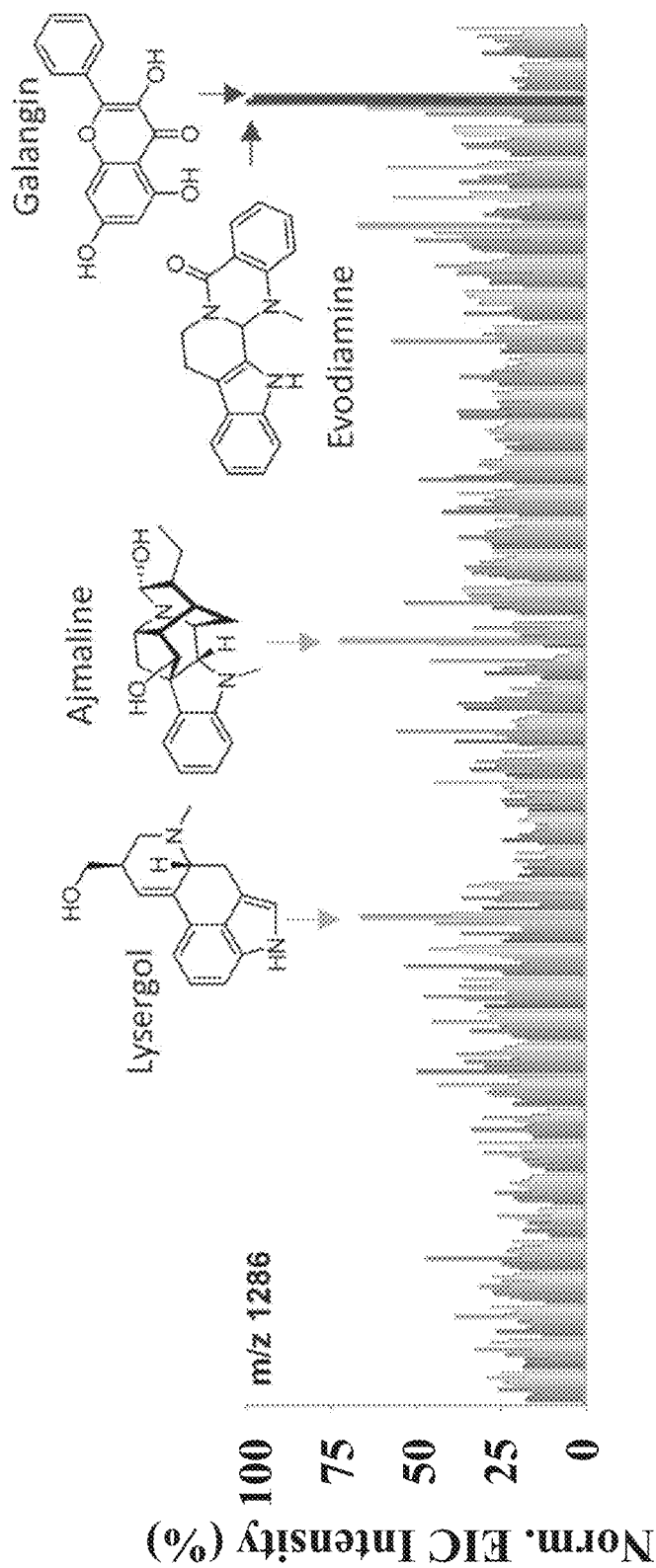
FIG. 10A is a 2D component of a 3D plot focusing on cryptic metabolites from *A. keratiniphila* (m/z 1286), highlighting effective elicitors.
Figure 10B:
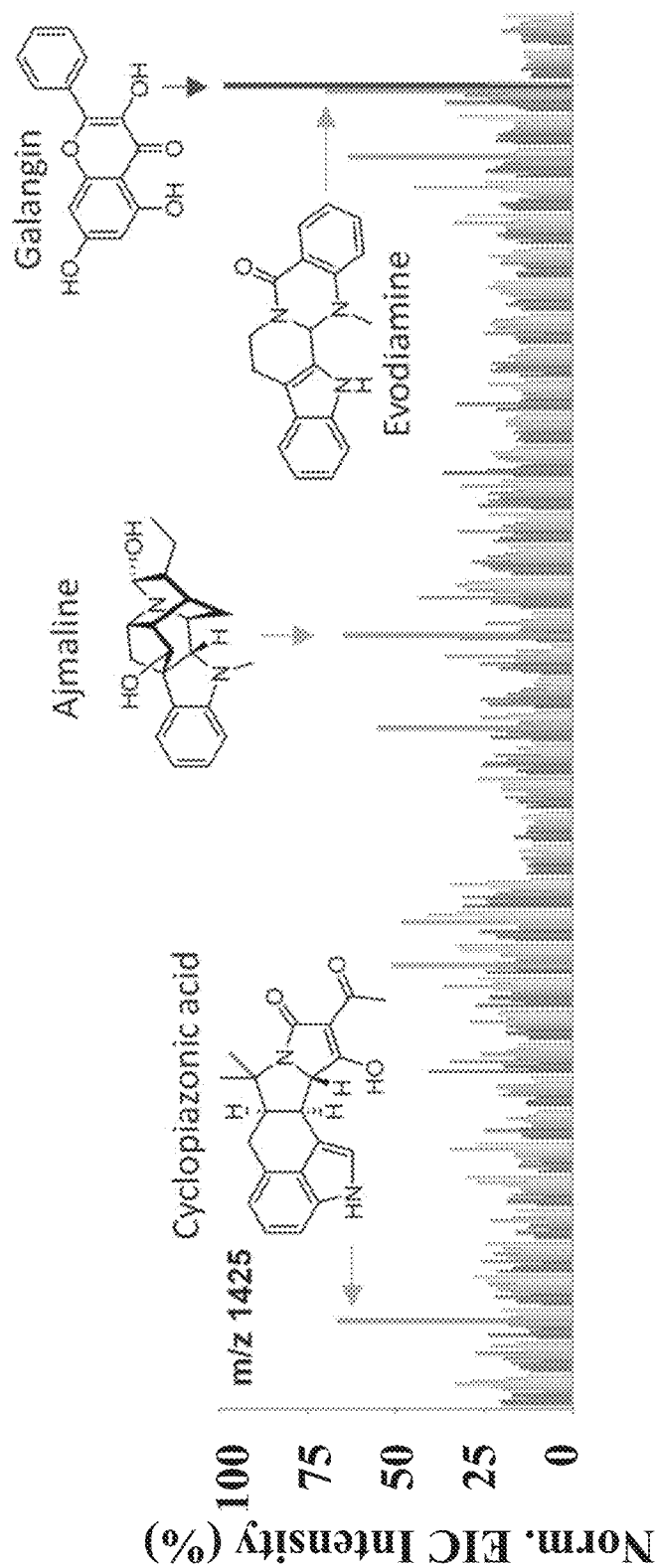
FIG. 10B is a 2D component of a 3D plot focusing on cryptic metabolites from *A. keratiniphila* (m/z 1425), highlighting effective elicitors.

Application of HiTES-IMS to Rare Actinomycetes. The disclosed approach was also applied to rare actinomycetes, a group of bacteria that account for some structurally fascinating and functionally potent metabolites, including the antibiotic of-last-resort vancomycin as well as the anticancer agent calicheamicin. Rare actinomycetes are an ideal test case for HiTES-IMS because in addition to their abundance of silent BGCs, they are difficult to manipulate genetically, thus all but precluding transcriptional reporter assays. *Amycolatopsis keratiniphila* NRRL B24117 were chosen as a test case. Its genome has not been sequenced, but efforts to find further BGCs that encode glycopeptide antibiotics (GPAs) using PCR had shown that it contains a vancomycin-like BGC, though a product has not yet been reported. *A. keratiniphila* was subjected to HiTES-IMS and obtained the metabolome shown, focusing on the mass range of typical GPAs (FIG. 9A). Again, induction of silent BGCs occurred in a high-throughput fashion, as numerous metabolites were observed that were only induced when challenged by compounds from the small molecule library (FIGS. 9A, 10A, 10B): a compound with m/z 1286 was induced by galangin and the indole-containing alkaloids evodiamine and ajmaline (FIG. 10A). Additionally, a compound with m/z 1425 was induced by similar elicitors, including galangin and evodiamine (FIG. 10B). Lastly, compounds with m/z 1654 and 1811 were observed in the induced metabolome, primarily by dihydroergocristine (Dhe) and vincamine (Vin, FIG. 9A, 9B). *A. keratiniphila* appeared to respond to indole-bearing alkaloids of diverse origins by activating numerous, otherwise silent, BGCs leading to the production of cryptic metabolites.

Figure 9C:
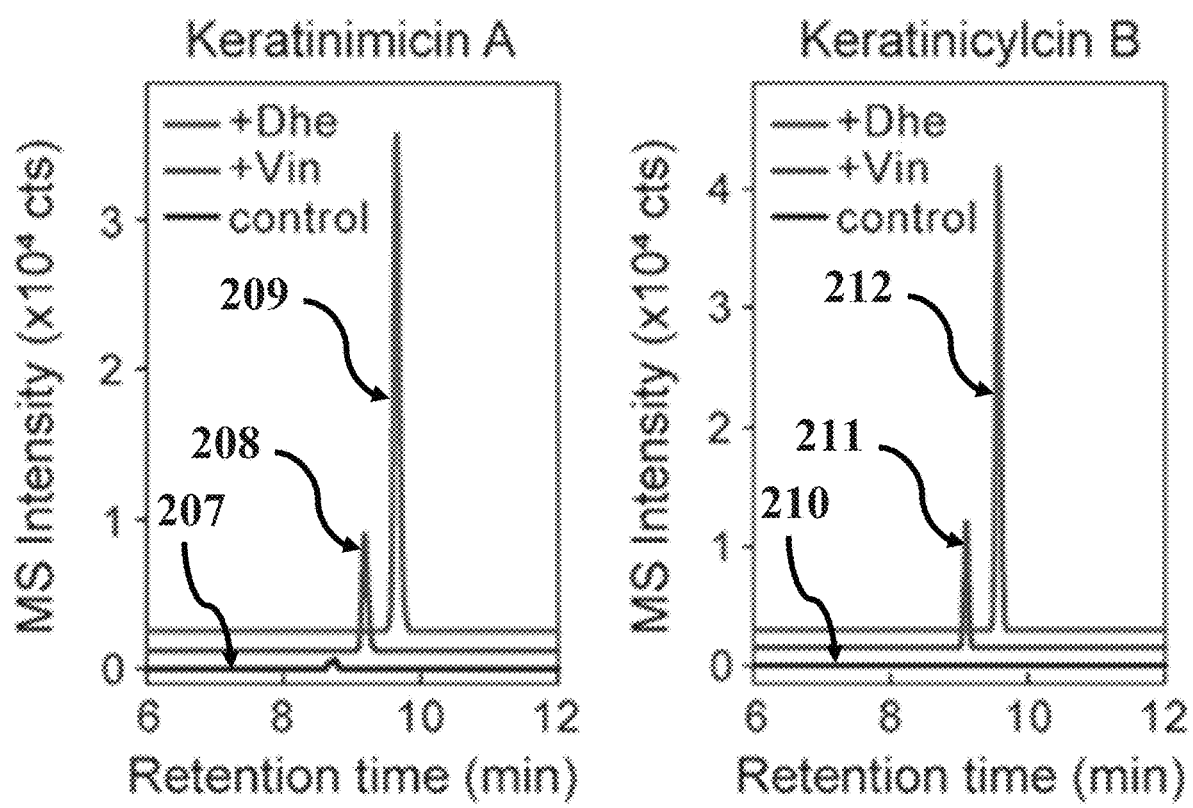
FIG. 9C depicts graphs of the HR-MS extracted ion chromatogram of keratinimicin A (left) and keratinicyclin B (right) by Dhe and Vin in flask cultures, where the traces are offset for clarity.
Figure 11B:
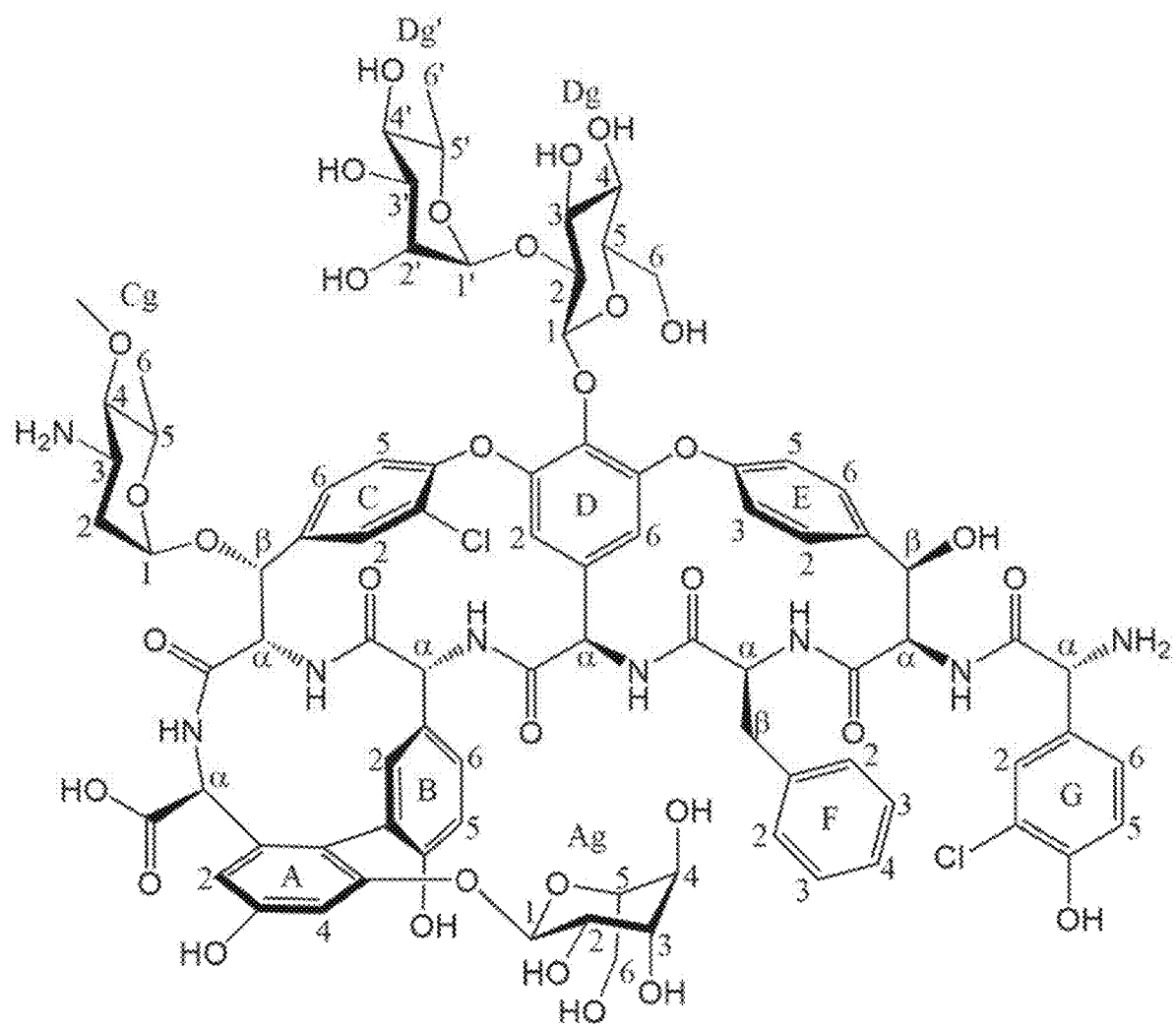
FIG. 11B is an illustration showing the numbering scheme for keratinimicin A.
Figure 12A:
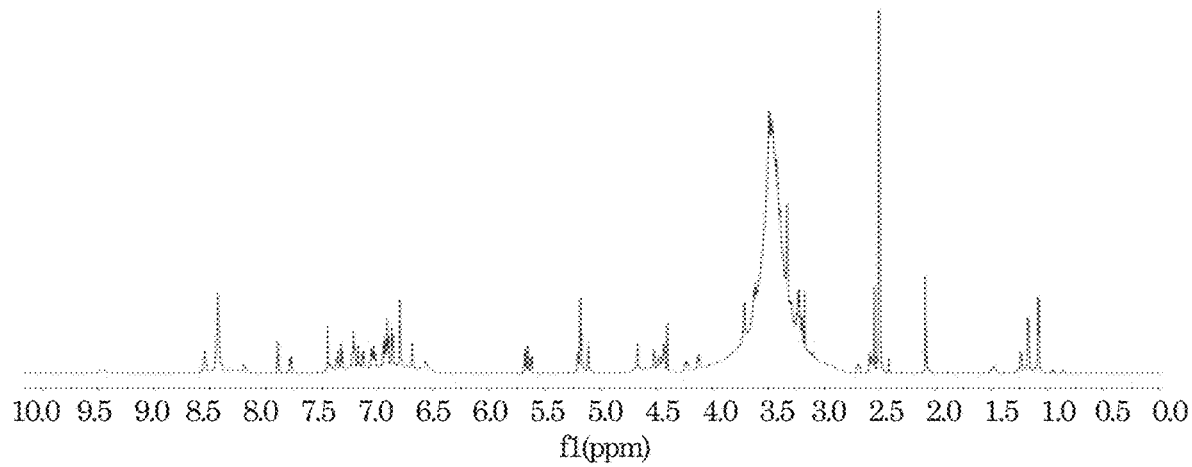
FIGS. 12A-12E are NMR spectra of keratinimicin A in DMSO-d6, including $^1H$ NMR (FIG. 12A), gCOSY (FIG. 12B), ROESY (FIG. 12C), HSQC (FIG. 12D) and HMBC (FIG. 12E).
Figure 12B:
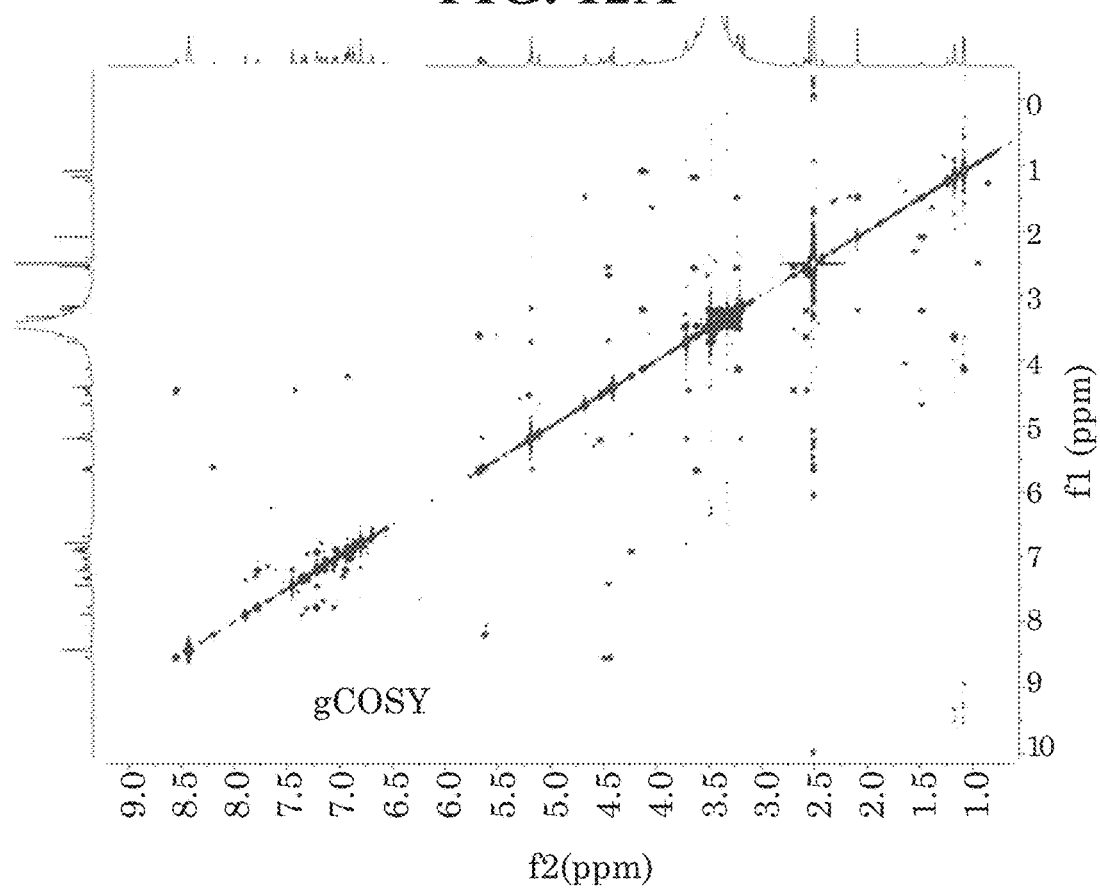
Figure 12C:
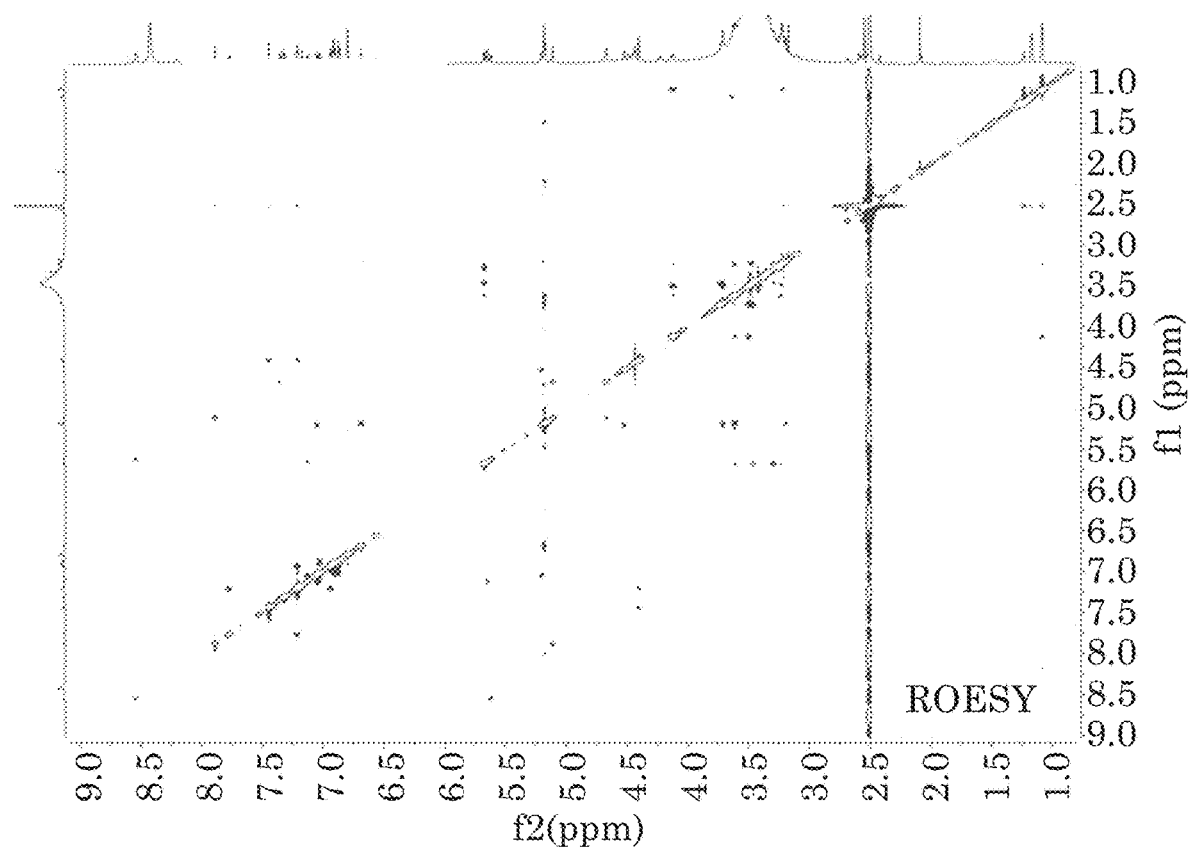
Figure 12D:
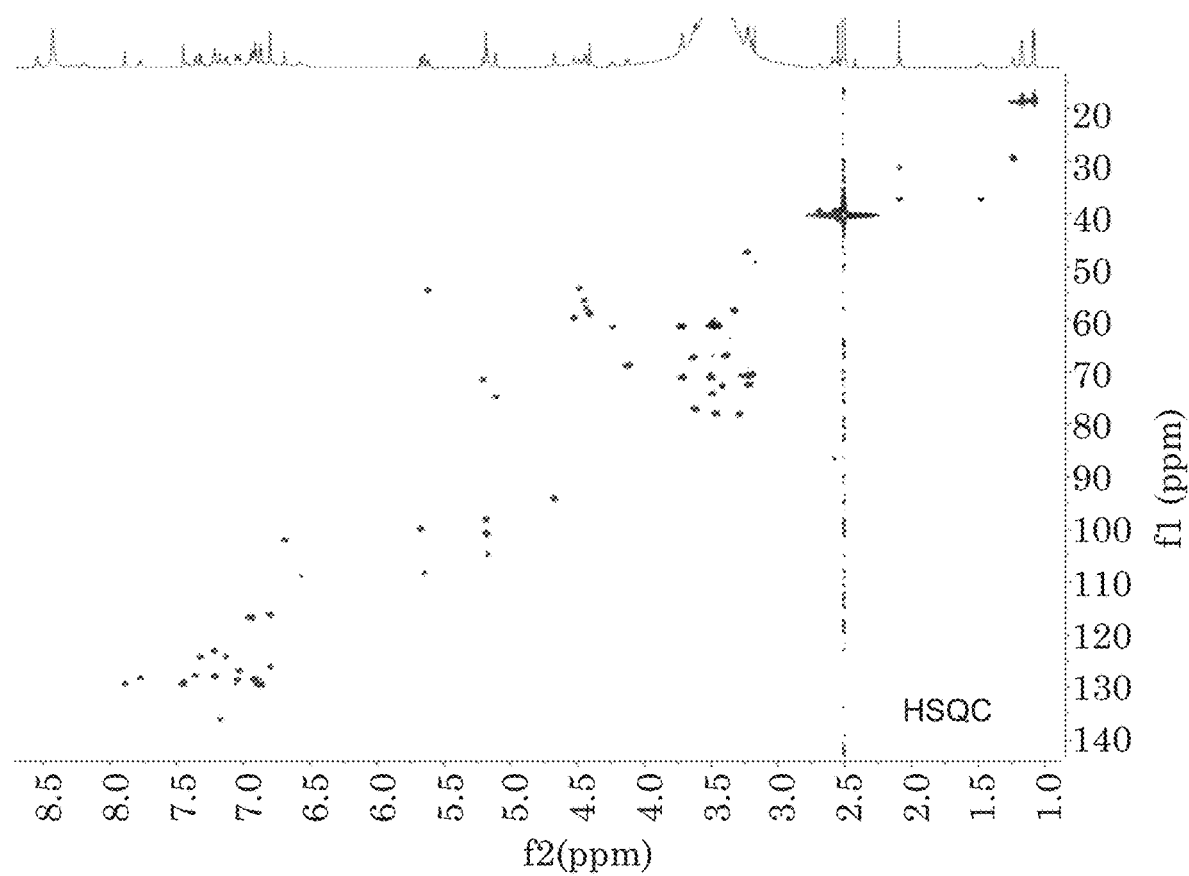
Figure 12E:
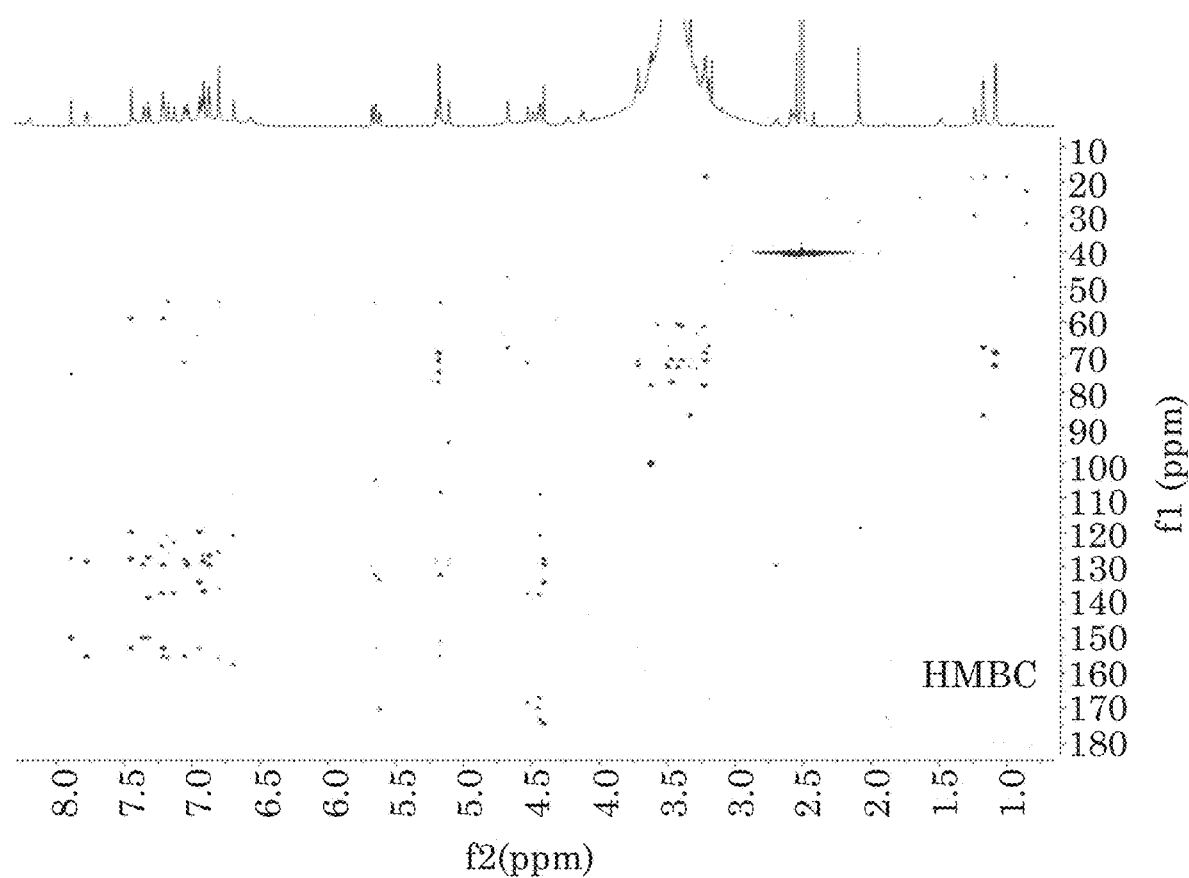

Of the compounds detected, one appeared to contain a Cl atom as judged by the HR-MS isotope distribution pattern, a common modification in GPAs (See FIG. 3). Follow-up experiments validated the strong stimulatory activity by Dhe and Vin, demonstrating a marked elicitation of the compound (FIG. 9C). FIG. 9C shows a graph indicating the elicitation of Keratinimicin A (left) and Keratinicyclin B (right) in uncontrolled (207, 210), Vin-treated (208, 211), and Dhe-treated (209, 212) cultures. As it was suspected that it might be the putative glycopeptide, seven analogs were isolated from large-scale production cultures in the presence of Dhe. HR-MS analysis suggested that these compounds fall into two families, one that is referred to as keratinimicins, and a second, the keratinicyclins. 1D/2D NMR analysis showed that keratinimicin A contains six highly modified amino acids, with recognizable α-$^1$Hs at 4.41, 4.52, 4.45, 5.62, 4.48, 4.23, and 4.42 ppm (FIGS. 9D (left), 11A, 11B). FIG. 9D illustrates relevant NMR correlations used to solve the structures of keratinimicin A (left) and keratinicyclin A (right). FIG. 11A provides NMR assignments for keratinimicin A in DMSO-d6. FIG. 11B provides the numbering scheme for keratinimicin A. TOCSY, HSQC, and HMBC analysis identified these as β-OH-Tyr, Phe, two crosslinked Hpg residues, a glycosylated β-OH-3-Cl-Tyr, and a crosslinked 3,5-dihydroxy-phenylglycine (Dpg) (See FIGS. 12A-12E. FIGS. 12A-12E provide NMR spectra of keratinimicin A in DMSO-d6. Specifically, $^1$H NMR (FIG. 12A), gCOSY (FIG. 12B), ROESY (FIG. 12C), HSQC (FIG. 12D), and HMBC (FIG. 12E).

Figure 9E:
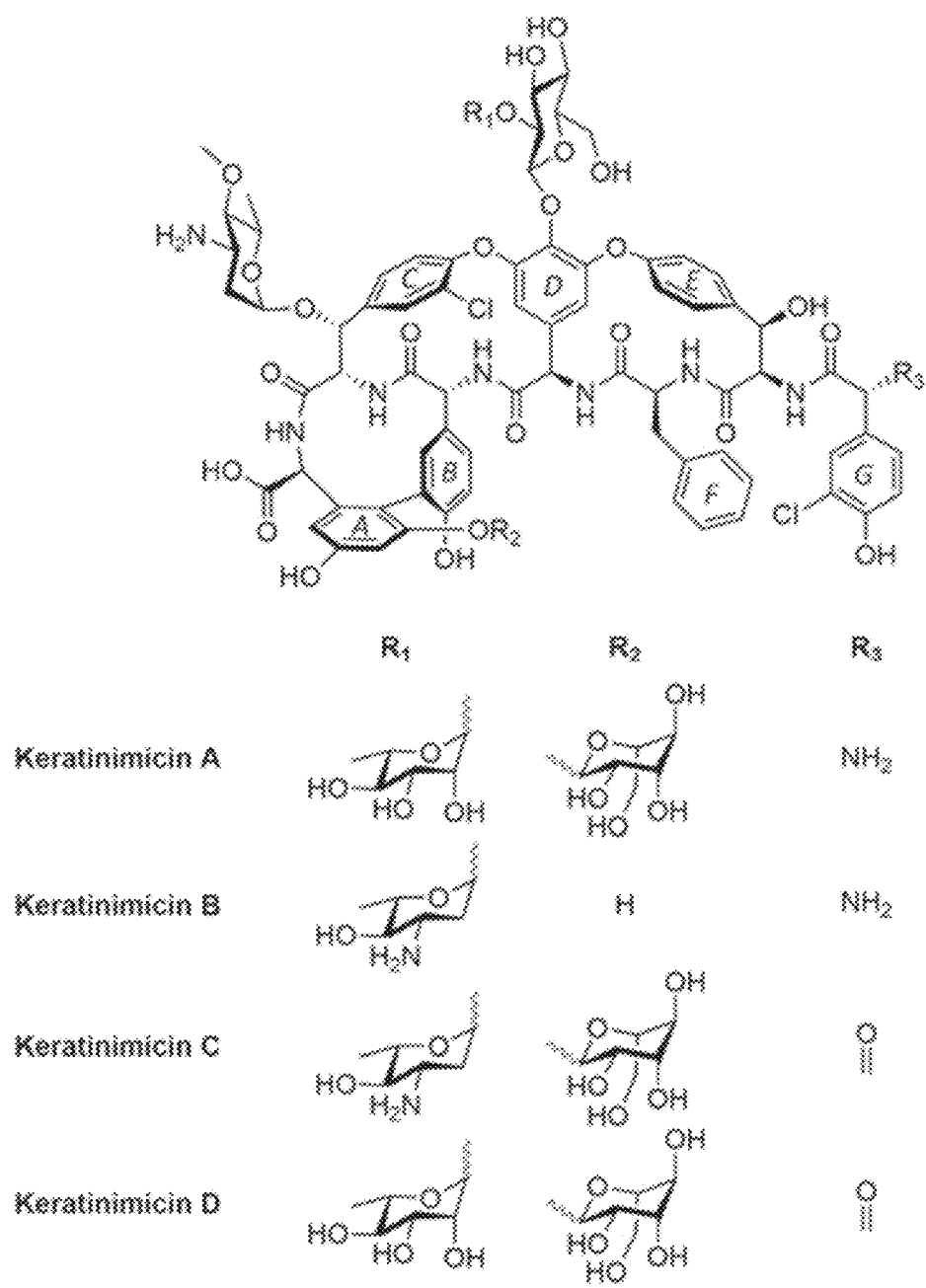
FIG. 9E depicts structures of four keratinimicin derivatives with different substitution patterns as indicated; the nomenclature to identify different rings in glycopeptides is shown.

Characteristically, the crosslinks occurred between rings A-B, via a carbon-carbon bond, and between rings C-D and D-E via aryl ether bonds as elucidated by HMBC and NOESY spectra (FIG. 9E). In FIG. 9E, structures of four keratinimicin derivatives with different substitution patterns are indicated. The nomenclature to identify different rings in glycopeptides is shown.

Figure 9F:
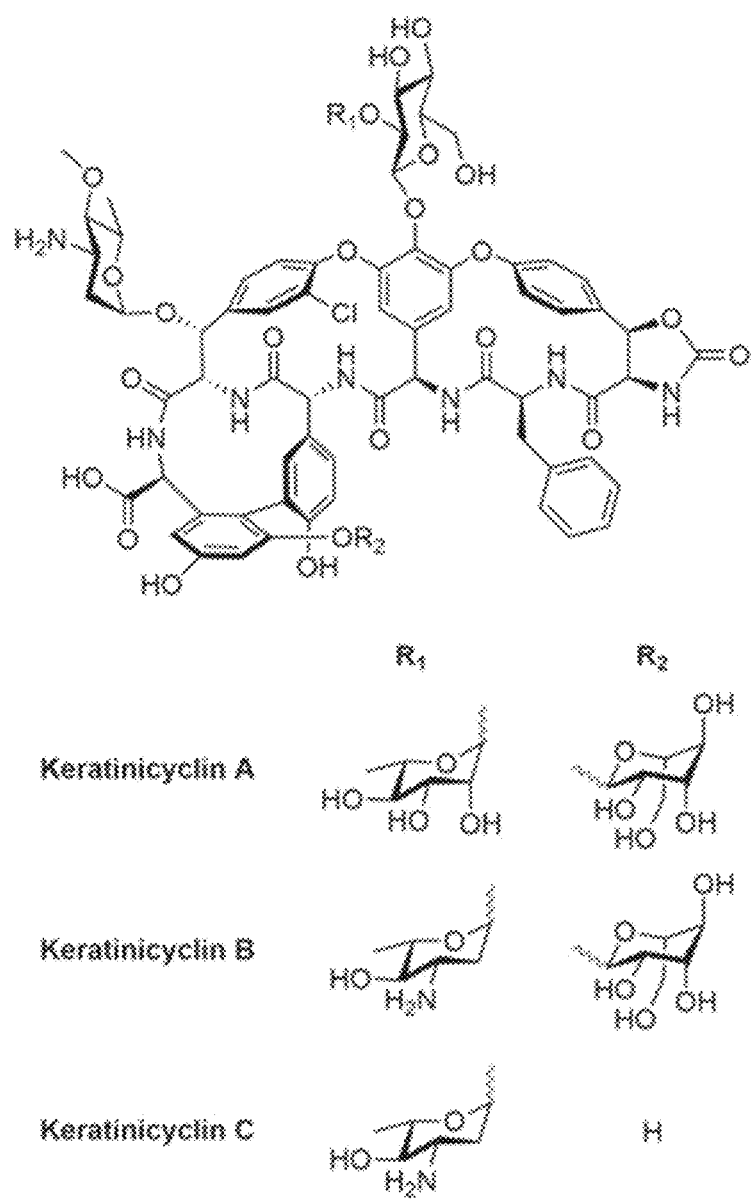
FIG. 9F depicts structures of three keratinicyclin derivatives with different substitution patterns as indicated.
Figure 9G:
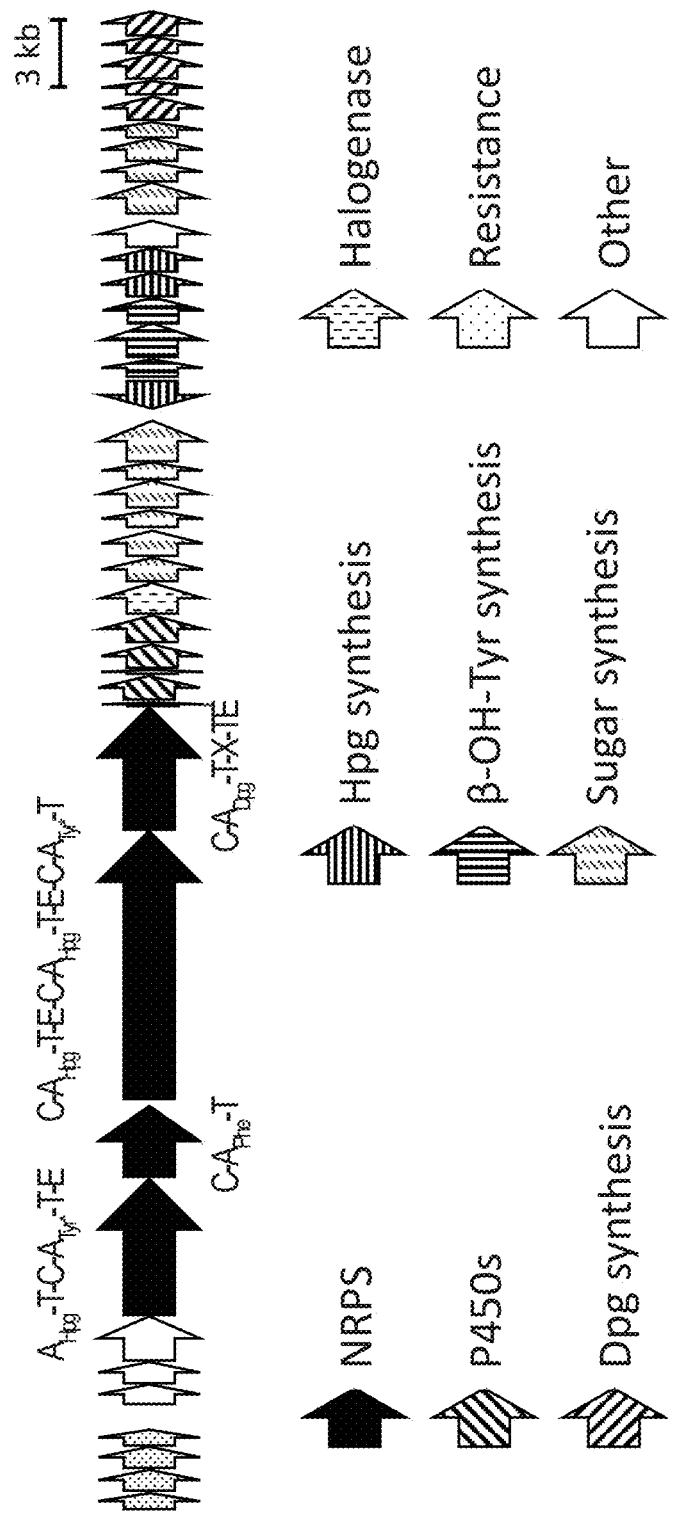
FIG. 9G depicts the ker BGC as identified by bioinformatic analysis after sequencing the genome of *A. keratiniphila*.

Four glycosyl groups were identified by NMR analysis, mannose, actinosamine, and a glucose-rhamnose disaccharide at residues A, C, and D, respectively, thus completing the two-dimensional structure of keratinimicin A. To assign the chiral centers, a combined spectroscopic and bioinformatic approach was chosen. Shot-gun sequencing of the entire genome of *A. keratiniphila* allowed us to pinpoint a GPA cluster, which was annotated as ker, using the canonical synteny previously described. FIG. 9G provides the ker BGC as identified by bioinformatic analysis after sequencing the genome of *A. keratiniphila*. The predicted domain composition for each NRPS is shown as are the predicted functions of the remaining enzymes in the BGC. Tyr* denotes modified Tyr.

It appears that ker is the first BGC reported for a class II GPA. Bioinformatic analysis revealed an identical domain organization as the archetypal class I GPAs. FIG. 9H provides annotation of the keratinimicin biosynthetic gene cluster (ker). A pattern of D- and L-amino acids as shown was proposed (from C- to N-terminus: L-L-D-D-L-D-D, FIG. 9E). Finally, the stereo-configuration of the β-OH groups were assigned as R by NMR NOESY correlations, thus completing the proposed three-dimensional structure. Keratinimicin A is similar to actinoidin A, except that it contains a chloride at ring G, and carries a different sugar at residue D.

Figure 13B:
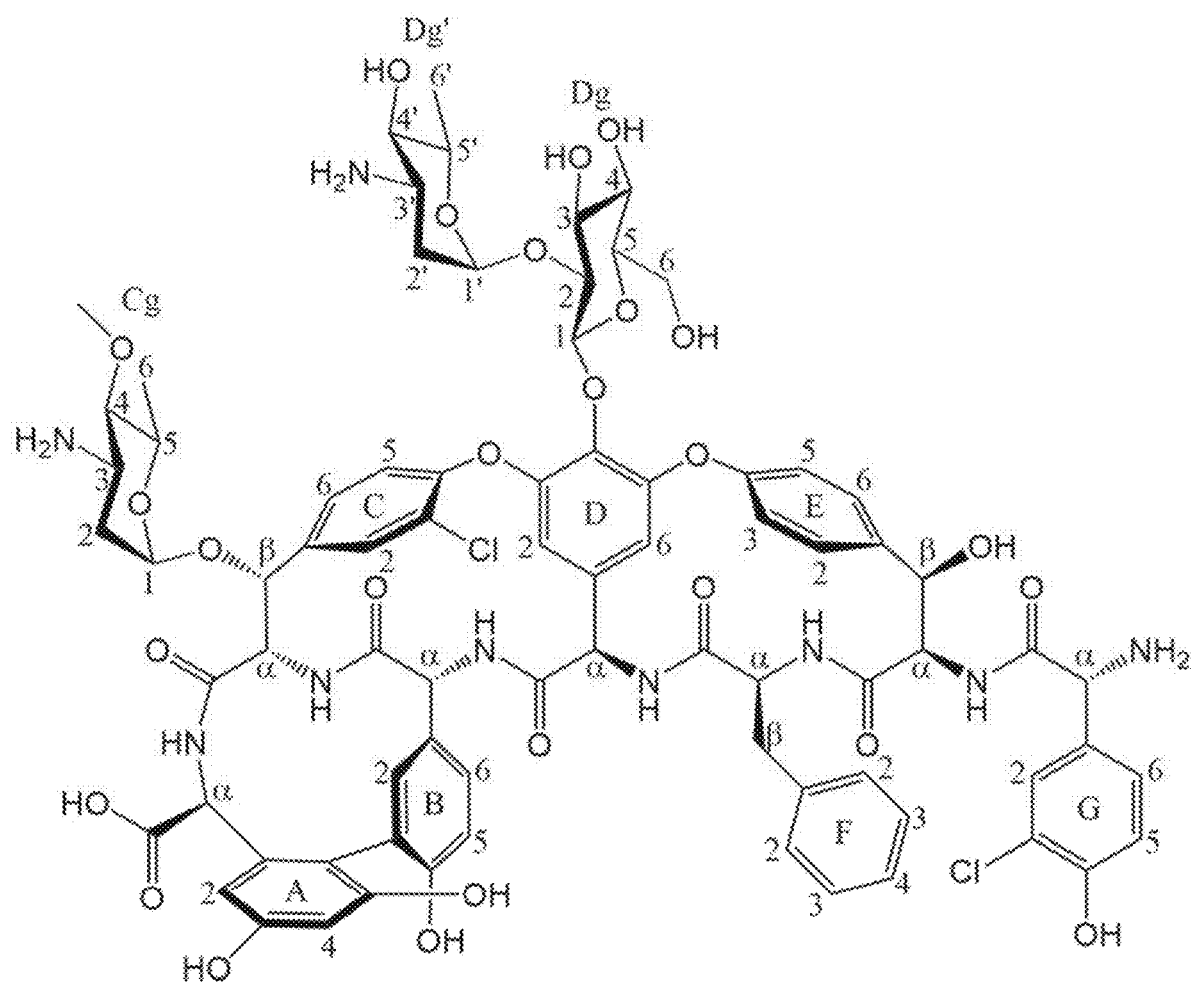
FIG. 13B is an illustration showing the numbering scheme for keratinimicin B.
Figure 14B:
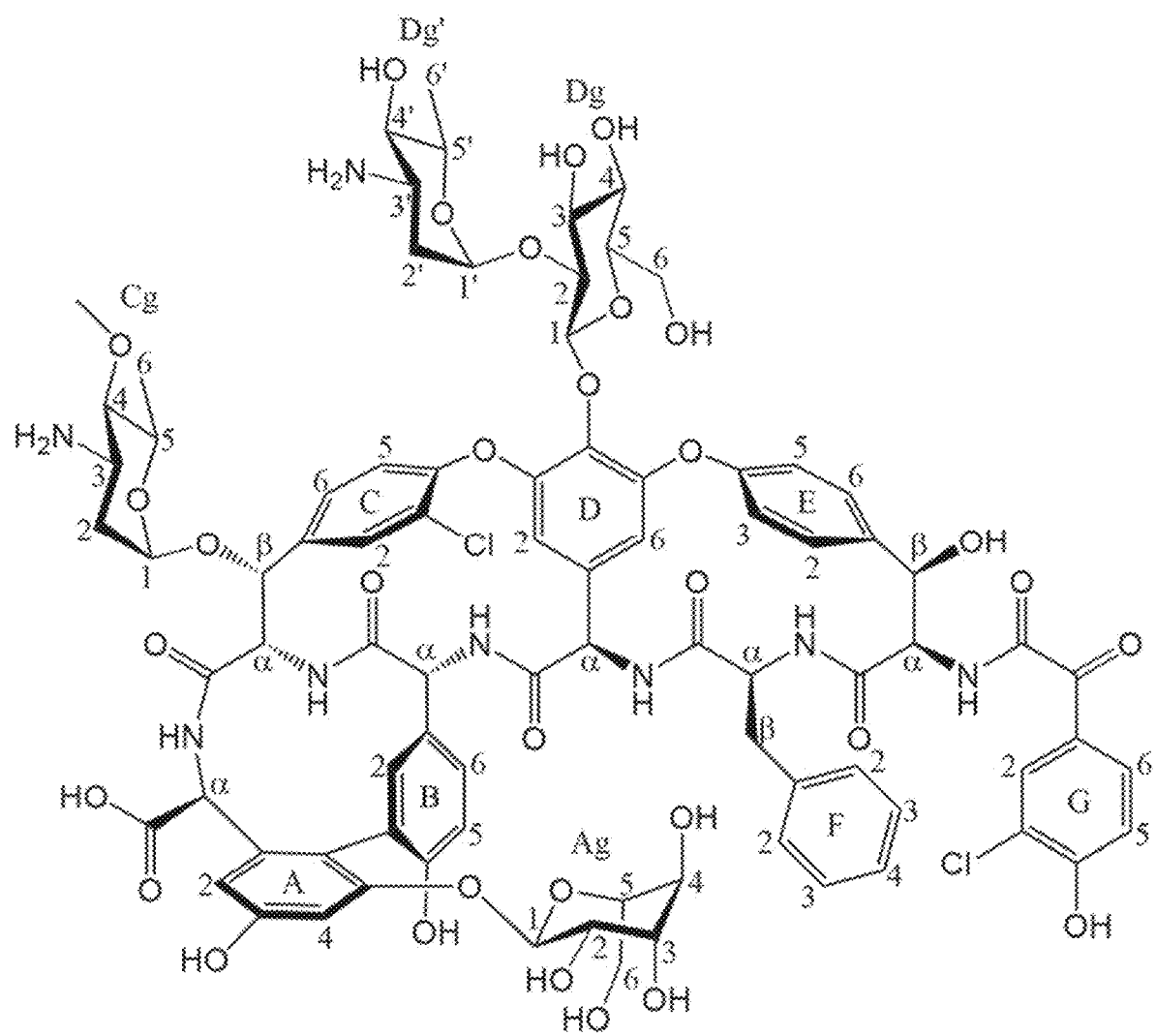
FIG. 14B is an illustration showing the numbering scheme for keratinimicin C.
Figure 15B:
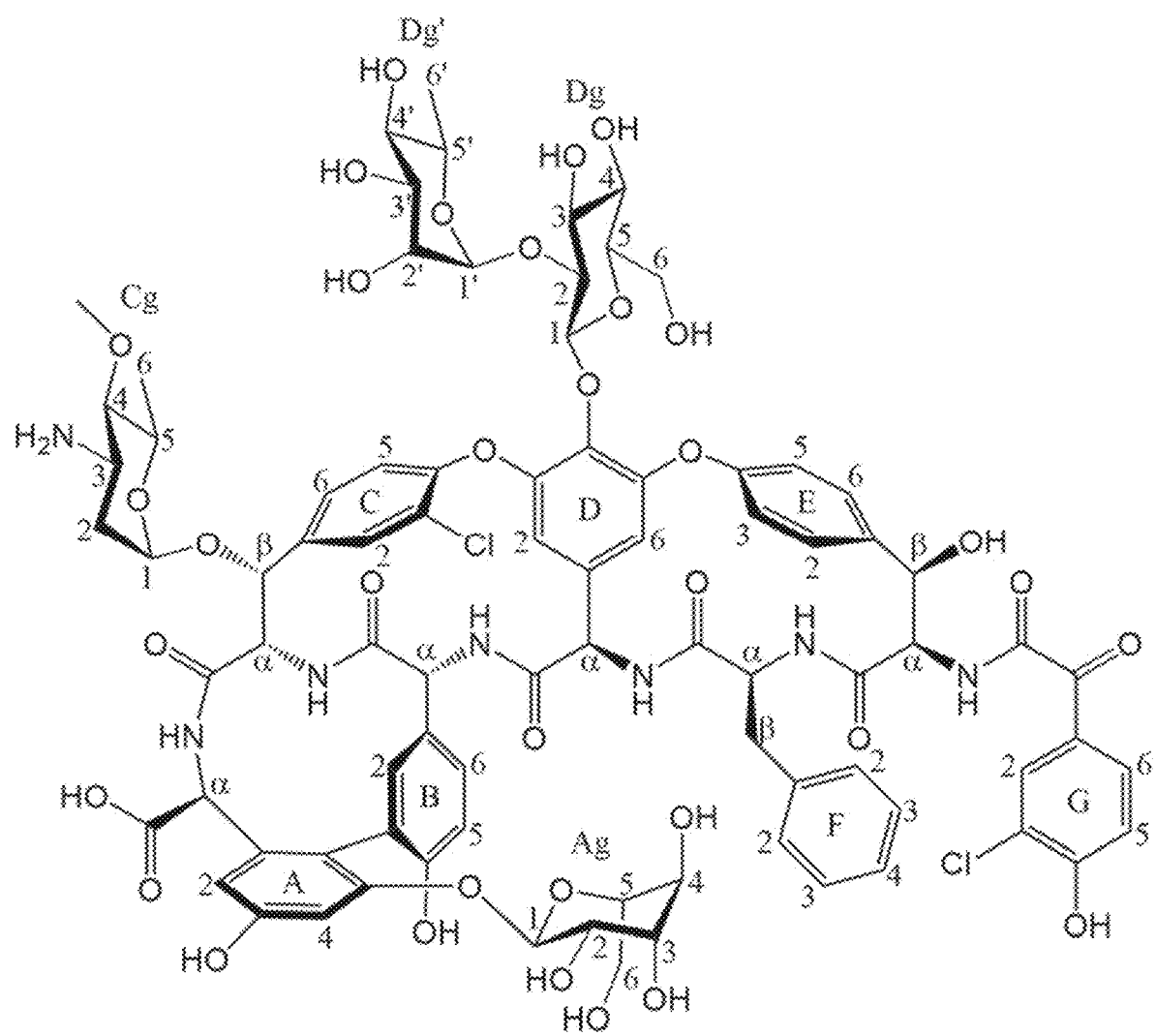
FIG. 15B is an illustration showing the numbering scheme for keratinimicin D.

Three additional keratinimicin analogs were identified and structurally elucidated as well. Relative to variant A, keratinimicin B only contains three glycosyl moieties: actinosamine and a glucose-acosamine disaccharide at residue C and D, respectively, while mannose at residue A is missing (See FIGS. 13A and 13B). FIG. 13A provides NMR assignments for keratinimicin B in DMSO-d6. FIG. 13B provides the numbering scheme for keratinimicin B. Keratinimicin C is N-terminally capped by an unusual 2-keto-m-chloro-o-hydroxyphenylacetic acid moiety, with again a different bouquet of sugar substituents (See FIGS. 14A and 14B). FIG. 14A provides NMR assignments for keratinimicin C in DMSO-d6. FIG. 14B provides the numbering scheme for keratinimicin C. Keratinimicin D also contains the 2-keto-m-chloro-o-hydroxyphenyl-acetic acid residue, with yet a different combination of sugars at residue D, relative to keratinimicin C (See FIGS. 15A and 15B). FIG. 15A provides NMR assignments for keratinimicin D in DMSO-d6. FIG. 15B provides the numbering scheme for keratinimicin D.

Figure 16B:
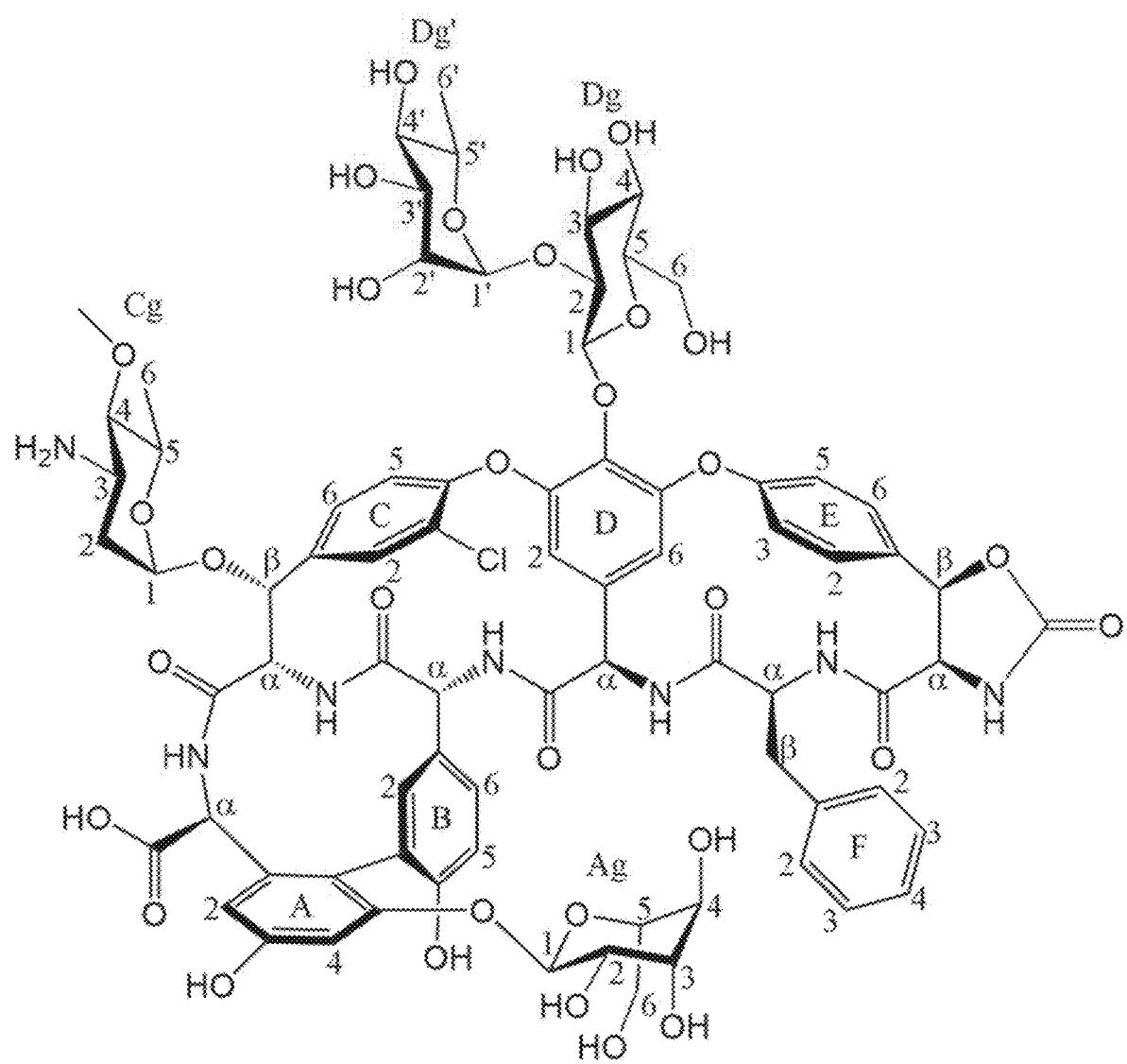
FIG. 16B is an illustration showing the numbering scheme for keratinicyclin A.

The structure of keratinicyclin A was characterized by extensive analysis of spectroscopic data leading to the structure shown (FIG. 9D (right), 9F). FIG. 9F provides structures of three keratinicyclin derivatives with different substitution patterns; the nomenclature to identify different rings in glycopeptides is shown in FIG. 9E. It consists of a 6mer peptidic backbone, containing the same sequence as the keratinimicins sans the N-terminal 3-Cl-Hpg residue. It bears the same aromatic crosslinks as the keratinimicins, with an A-B biaryl bond as well as the C-O-D and D-O-E aryl ether crosslinks. The glycosyl groups were also identified by NMR analysis as described above (See FIG. 16A, 16B, 9E, 9F). FIG. 16A provides NMR assignments for keratinicyclin A in DMSO-d6, while FIG. 16B provides the numbering scheme for keratinicyclin A.

Most notably, the keratinicyclins contain an N-terminal 2-oxazolidinone, a functional group present in the clinically used antibiotics linezolid and tedizolid. Thus, the keratinicyclins combine the characteristic features of the GPAs with those of the oxazolidinone antibiotics, the first such combination reported thus far. Within the GPAs, the keratinicyclins represent a new chemotype.

Figure 17B:
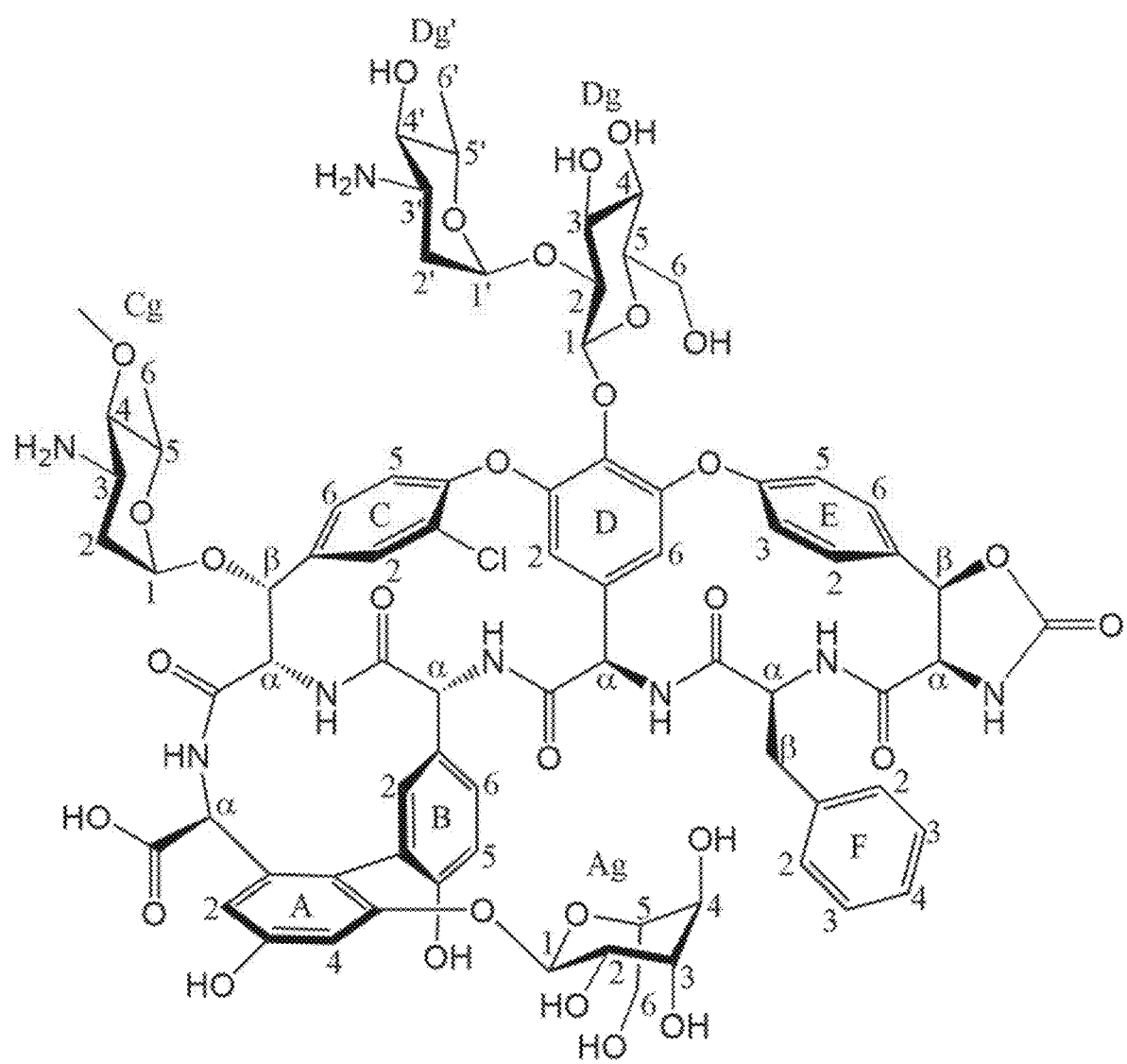
FIG. 17B is an illustration showing the numbering scheme for keratinicyclin B.
Figure 18B:
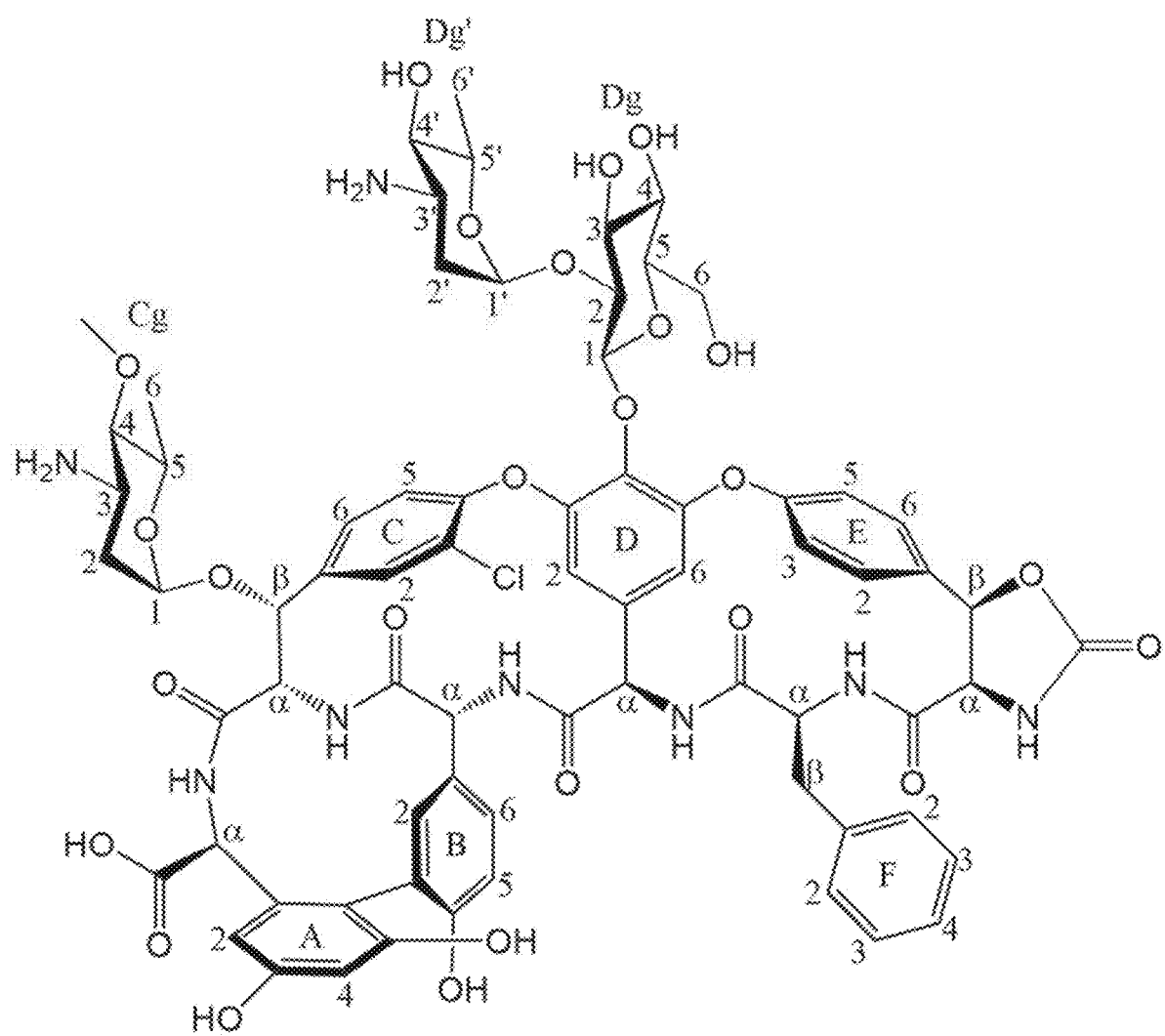
FIG. 18B is an illustration showing the numbering scheme for keratinicyclin C.

The structures of 2 additional keratinicyclins were solved. Relative to derivative A, keratinicyclin B contains a glucose-acosamine disaccharide at residue D, rather than glucose-rhamnose (See FIGS. 17A and 17B). FIG. 17A provides NMR assignments for keratinicyclin B in DMSO-d6. FIG. 17B provides the numbering scheme for keratinicyclin B. Keratinicyclin C also contains a glucose-acosamine disaccharide at residue D but lacks mannose at residue A (See FIGS. 18A and 18B). FIG. 18A provides NMR assignments for keratinicyclin C in DMSO-d6. FIG. 18B provides the numbering scheme for keratinicyclin C.

Initial in-house assays revealed strong antimicrobial activity for the keratinimicins, but not for the keratinicyclins. Keratinimicins A and C were submitted for broad bioactivity tests against bacterial pathogens. Because some GPAs have been documented to harbor antiviral properties, keratinicyclins B and C were assessed against a panel of pathogenic human viruses. Keratinimicins showed potent antibacterial activity against numerous Gram-positive pathogens, with MICs (minimal inhibitory concentrations) akin to those of vancomycin against *Streptococci, Clostridium difficile*, and *Enterococcus faecalis* (See FIG. 19). FIG. 19 shows MIC and $IC_{50}$ values (in μM) for keratinimicins and keratinicyclins against select pathogenic bacteria and viruses. Significant bioactivities (MIC or $IC_{50}$<10 μM) are shown in bold. They were ineffective against vancomycin-resistant *Enterococci*, suggesting a similar mode of action as vancomycin. Keratinicyclins did not exhibit significant antibacterial activity but were potent inhibitors against the respiratory syncytial virus (RSV). Indeed, the half-maximal inhibitory concentration ($IC_{50}$) determined against RSV is ~10-fold more potent than that of the currently-used drug, Ribavirin. Thus, keratinimicins and keratinicyclins may be useful for various treatment options, contacting a microorganism or treating a viral infection with keratinimicin or keratinicyclin—or its pharmaceutically acceptable salt. In some embodiments, the microorganism may be a gram-positive bacterium, including but not limited to *Staphylococcus aureus, Streptococcus agalactiae, Streptococcus pyogenes, Streptococcus pneumoniae, Clostridium difficile, Enterococcus faecalis*, and *Bacillus subtilis*.

The discoveries of these cryptic antibacterial and antiviral agents highlight the utility of HiTES-IMS in unearthing novel metabolites with potentially therapeutic bioactivities.

In one example, to validate the elicitors and induction of cryptic metabolites identified in the high-throughput screen, flask cultures of each condition were grown and subsequently analyzed by HPLC-MS. In another example, to validate orfamide production, 5 mL overnight cultures of *P. protegens* were prepared as described above. The culture was then diluted into 2×125 mL Erlenmeyer flasks, each containing 20 mL of LB to give an initial $OD_{600\,nm}$ of 0.01. One flask was supplemented with cafestol at a final concentration of 22 μM; the other was supplemented with the same volume of DMSO (no-cafestol control). Both cultures were incubated at 25° C./150 rpm. After 44 h, cells were removed by centrifugation, and 10 mL of each supernatant was desalted on a C8 PrepSep solid-phase extraction column (Fisher). After loading, the columns were washed with water, and bound material eluted with a 2-step gradient of 50% MeCN (in $H_2O$) and 100% MeCN. The fractions were dried in vacuo, redissolved in 100 μL MeOH, and analyzed by HPLC-Qtof-MS.

In another example, to validate canucin production, seed cultures of *S. canus* were prepared as described above. The culture was diluted into 2×250 mL Erlenmeyer flasks, each containing 50 mL of R4 medium to a final mycelial concentration of 0.05% (w/v). Kenpaullone was added to one flask (final concentration of 17 μM), while the other served as control and received the same volume of DMSO. The cultures were then grown at 30° C./200 rpm for 5 days. The resulting supernatants were extracted twice with 30 mL of ethyl acetate. The organic phases were combined, dried in vacuo, re-dissolved in 200 μL MeOH, and the two samples analyzed by HPLC-Qtof-MS.

In another example, to validate keratinimicin and keratinicyclin production, seed cultures of *A. keratiniphila* were prepared as described above. The culture was diluted into 3×1 mL wells in a deep-well 96 well plate containing 0.9 mL of R4 medium at a final mycelia concentration of 0.05% (w/v). The 96-well plate was supplemented with a final concentration of 7.8 μM vincamine (well 1), 2 μM Dhe (well 2), and the same volume of DMSO as control (well 3). The plate was then grown at 30° C./200 rpm for 5 days. Cells and mycelial mass was removed by centrifugation, and the wells were worked up as described above for 96-well screens and analyzed by HPLC-Qtof-MS.

Alternatively, the seed culture was diluted into 3×250 mL Erlenmeyer flasks containing 50 mL of R4 medium at a mycelial concentration of 0.05% (w/v). The flasks were supplemented with 7.8 μM vincamine (flask 1), 2 μM Dhe (flask 2), and the same volume of DMSO as control (flask 3), and subsequently grown at 30° C./200 rpm for 5 days. Cells and mycelia were removed by centrifugation, and 10 mL of each supernatant was loaded on a C18 SPE column (Phenomenex, 100 mg), washed with water, and eluted with 50% and 100% MeCN. The fractions were dried in vacuo, re-dissolved in 100 μL MeOH, and analyzed by HPLC-Qtof-MS. The deep-well plate method resulted in better induction of keratinimicin and keratinicyclin.

In other embodiments, Large-scale fermentation of *S. canus* and *A. keratiniphila* was carried out following a similar procedure as for small-scale fermentations described above. 3-day seed cultures were prepared as above. They were then used to inoculate several 2 L Erlenmeyer flasks containing 200 mL of R4 medium with isolated mycelia to a final concentration of 0.01% (w/v). The culture was then supplemented with an optimal concentration of the elicitor. Typically 8-12 L of total culture was used for compound isolation. The flasks were incubated at 30° C./250 rpm for 7 days, at which point the desired products were purified.

In some examples, HPLC-MS analysis was performed on an Agilent 1260 Infinity Series HPLC system equipped with an automated liquid sampler, a diode array detector, and a 6120 Series ESI mass spectrometer using a reversed phase Luna C18 column (Phenomenex, 5 μm, 150×4.6 mm). The mobile phases consisted of water and MeCN (both containing 0.1% formic acid). Upon injection, elution was carried out isocratically with 5% MeCN in water for 3 min followed by gradients of 5% MeCN to 70% MeCN in water over 20 min, and then 70% to 100% over 5 min, at a flow rate of 0.6 mL/min. High-resolution (HR) HPLC-MS and HR-tandem HPLC-MS were carried out on an Agilent 6540 Accurate Mass Qtof LC-MS, consisting a 1260 Infinity Series HPLC system, an automated liquid sampler, a diode array detector, a JetStream ESI source, and the 6540 Series Qtof. Samples were resolved on a Luna C18 column (Phenomenex, 5 µm, 100×4.6 mm). The mobile phase consisted of water and MeCN (+0.1% formic acid). Elution for orfamides was carried out isocratically with 10% MeCN in water (3 min) followed by a gradient of 10%-95% MeCN over 8 min, followed by an isocratic elution at 95% MeCN over 25 min at a flow rate of 0.4 mL/min. Elution of canucins, keratinimicins and kertinicyclins was carried out isocratically with 5% MeCN in water (3 min) followed by a gradient of 5%-95% MeCN in water over 15 min, at a flow rate of 0.4 mL/min.

In some examples, HPLC purifications were carried out on an Agilent preparative HPLC system equipped with a 1260 Infinity series binary pump, a diode array detector, and an automated fraction collector. Semi-preparative or analytical-scale purifications were performed on an Agilent HPLC system containing a1260 Infinity Series binary pump or a 1290 Infinity quaternary pump. Each system was equipped with an automatic liquid sampler, a temperature-controlled column compartment, a diode array detector, and an automated fraction collector. The mobile phases used consisted of water and MeCN, with or without 0.1% formic acid depending on samples.

In some examples, Canucins were purified from 12 L fermentation of $S.\ canus$ in the presence of kenpaullone (at a final concentration of 17 µM). After 7-day fermentation, the resultant supernatant was extracted twice with an equal volume of ethyl acetate. The combined organic phase was dried over $Na_2SO_4$, subsequently dried in vacuo, resuspended in 45 mL MeOH, and purified on an Agilent Preparative HPLC. The sample was resolved with repeated injections onto a preparative Luna C18 column (Phenomenex, 5 µm, 21.2×250 mm) operating at a flow rate of 12 mL/min with mobile phases consisting of water and MeCN (+0.1% formic acid). Upon injection, elution was carried out isocratically with 20% MeCN for 2 min, followed by a gradient of 20%-100% MeCN over 25 min. Peaks containing canucin A and B, as judged by HPLC-MS, were pooled, dried in vacuo, resuspended in MeOH and further purified on a semi-preparative/analytical Agilent HPLC system. The peptides were purified on a semi-preparative XDB-C8 column (Agilent, 5 µm, 10×250 mm) operating at a flow rate of 2.5 mL/min with a gradient of 30%-50% MeCN (in water) over 30 min followed by a gradient of 50%-100% MeCN over 5 min. Peaks containing pure canucin B were combined and lyophilized to dryness. Peaks containing canucin A were pooled, dried in vacuo, resuspended in MeOH, and further purified on a semi-preparative Luna C18 column (Phenomenex, 5 µm, 10×250 mm) with a gradient of 33%-55% MeCN (in water) over 30 min followed by a gradient of 55%-100% MeCN over 5 min. Peaks containing pure canucin A were combined, and lyophilized to dryness. This procedure gave 3.6 mg of canucin A and 1.7 mg canucin B.

In some examples, Keratinimicins and keratinicyclins were purified from 8 L fermentations of $A.\ keratiniphila$ in the presence of 2 µM Dhe. After 7-day fermentation, the resulting supernatant was loaded on a pre-packed C18 column (Phenomenex, 50 µm, 65 Å, 10 g) and eluted with 20%, 50% and 100% MeCN in water step-wise. The 20% fraction containing keratinimicins and keratinicyclins was dried in vacuo, resuspended in 50 mL MeOH, and further purified on an Agilent 1260 Infinity Series Preparative HPLC using a Luna C18 column (Phenomenex, 5 µm, 21.2×250 mm) operating at a flow rate of 12 mL/min with mobile phases consisting of water and MeCN (+0.1% formic acid). Upon injection, elution was carried out isocratically with 5% MeCN in water for 2 min, followed by a gradient of 5%-40% MeCN in water over 20 min, followed by a gradient of 40%-100% MeCN over 5 min. Fractions were collected in 1 min intervals over the time range of 5-25 min. Peaks containing keratinimicin A-D, as judged by HPLC-MS analysis, were pooled, dried in vacuo, resuspended in MeOH and further purified on a semi-preparative/analytical Agilent HPLC system. The sample was applied to a an RP Amide-C16 column (Supelco, 5 µm, 10×250 mm) operating at a flow rate of 2.5 mL/min with the same mobile phases as above and a gradient of 8%-16% MeCN in water over 30 min followed by a gradient of 16%-100% MeCN over 5 min. Peaks containing pure keratinimicin C and D were combined and lyophilized to dryness. Peaks containing keratinimicin A and B were pooled, dried in vacuo, resuspended in MeOH and further purified on a semi-preparative XDB-C8 column (Agilent, 5 µm, 10×250 mm) with a gradient of 5%-15% MeCN in water over 30 min followed by a gradient of 15%-100% MeCN over 5 min. Peaks containing pure keratinimicin A and B were combined and lyophilized to dryness. This procedure gave 8.5 mg of keratinimicin A, 1.6 mg keratinimicin B, 5.1 mg keratinimicin C, and 0.8 mg keratinimicin D.

Peaks containing keratinicyclin A-C from the preparative Luna C18 column were pooled, dried in vacuo, resuspended in MeOH and further purified on a semi-preparative/analytical Agilent HPLC system. The sample was applied to a RP Amide-C16 column (Supelco, 5 µm, 10×250 mm) operating at a flow rate of 2.5 mL/min with the same mobile phase as above and a gradient of 10%-20% MeCN in water over 30 min followed by a gradient of 20%-100% MeCN over 5 min. Peaks containing pure keratinicyclin A and C were combined, and lyophilized to dryness. Peaks containing keratinicyclin B were pooled, dried in vacuo, resuspended in MeOH and further purified on a semi-preparative XDB-C8 column (Agilent, 5 µm, 10×250 mm) with a gradient of 5%-15% MeCN in water over 30 min followed by a gradient of 15%-100% MeCN over 5 min. This procedure gave 2.7 mg of keratinicyclin A, 5.3 mg keratinicyclin B, and 1.2 mg keratinicyclin C.

In some examples, for structural elucidation, 1D/2D NMR spectra were acquired on an A8 Avance III HD 800 MHz NMR spectrometer (Bruker) with a triple resonance cryo-probe. The NMR samples of keratinimicin A-D and keratinicyclin A-C were prepared in DMSO-d6, and those of canucin A and B were prepared in $CD_3OH$.

In some examples, a NOESY spectrum of canucin A acquired in $CD_3OH$ at 295 K with a mixing time of 500 ms exhibited the greatest number of correlations, while avoiding spin diffusion, and was therefore used for structure calculations. Cross-peak positions and volumes in this spectrum were measured in MestReNova and assigned manually. These were given as initial input data for the calculations, which were performed in CYANA 2.1 on a Linux cluster. The isopeptide bond was incorporated via explicit distance constraints for the N—C bond between the N of Gly1 and the $C_\gamma$ of Asp8. Specifically, both of the upper and lower limits for the N—$C_\gamma$ bond length were set to 1.4 Å, with weighting factors of 1.00. These distances were based on the average bond length of an amide bond. The unnatural amino acid □-OH-Asp in canucin A was encoded into the CYANA residue library using CYLIB software[2]. Seven cycles of combined NOESY assignment and structure calculation were performed, followed by a final structure calculation. Calibration parameters for extraction of distance constraints from cross-peak volumes were determined automatically.

For each cycle and for the final calculation, 100 initial conformers were generated, and a simulated annealing schedule, composed of 10000 torsion angle dynamic steps, was applied to each conformer. Statistics were generated for the 10 conformers with the lowest final target functions (see Table S3). The calculated conformers were visualized in PyMoL.

To determine antibacterial and antiviral performance, assays were performed. In one example, antibacterial assays were carried out by Micromyx, LLC in accordance with methods from the Clinical and Laboratory Standards Institute. Minimal inhibitory concentrations were determined with the following strains: *S. aureus* ATCC 29213, *S. aureus* MMX 2011, *S. pneumoniae* ATCC 49619, *S. pyogenes* MMX 6253, *S. agalactiae* MMX 6189, *E. faecalis* ATCC 29212, *E. faecalis* MMX 486, *B. subtilis* ATCC 6633, *E. coli* ATCC 25922, *K. pneumoniae* MMX 214, *P. aeruginosa* ATCC 27853, *A. baumannii* ATCC 19606, *V. cholerae* BAA-2163, *C. difficile* ATCC 700057, and *B. fragilis* ATCC 25285.

In this example, antiviral assays were performed by Virapur in accordance with methods from the Clinical and Laboratory Standards Institute. Minimal inhibitory concentrations were determined with the following viruses and host cells (listed in Table 1): Influenza A/Perth/16/2009 in MDCK cells, Influenza B/Wisconsin/1/2010 in MDCK cells, Herpes Simplex 1 Strain MacIntyre in Vero cells, Herpex Simplex 2 Strain G in Vero cells, Vaccinia virus WR in Vero cells, Rhinovirus 8 in HeLa cells and Respiratory Syncytial Virus in Hep2 cells.

In another example, Keratinimicins and keratinicyclins were purified from large-scale production cultures of *Amycolatopsis* sp. B24117. A total of 6 L were cultured in 6×4 L Erlenmeyer flasks, each containing 1 L of R4 medium. The flasks were inoculated with *Amycolatopsis* sp. B24117 overnight cultures, supplemented with 30 µM of dihydroergocristine, and cultured for 6 days. After 6 days, the cells were removed by centrifugation (30 min, 8000 g) and the supernatant loaded into a PHENOMENEX® prepacked Sep-Pak column (5 g). Keratinimicins and keratinicyclins were washed with water, then eluted with a step gradient of 10%, 25%, 50%, and 100% MeCN (in $H_2O$), The glycopeptides eluted in the 25% fraction as determined by HPLC-MS. They were further purified by HPLC using an Agilent 1200 Series analytical HPLC system equipped with a photo diode array detector and an automated fraction collector on a PHENOMENEX® LUNA® C18 semi-preparative column operating at 2.5 mL/min. The column was equilibrated in 10% MeCN in water, both MeCN and water contained 0.1% formic acid. Upon injection of the crude material, elution was then carried out with a gradient of 10-60% MeCN (in water) over 35 min. Fractions contained glycopeptides, as judged by HPLC-MS, were collected, dried in vacuo, resuspended in a small volume of MeOH, and hten reapplied to the same column. Elution was carried out isocratically at 13% MeCN in water over 1 hour. Pure keratinimicins and keratinicyclins were characterized by high resolution HPLC-ESI-MS (HR-MS) on an Agilent 6540 UHD Accurate Mass Q-tof LCMS system, which consisted of a 1260 Infinity Series HPLC system, an automated liquid sampler, a diode array detector, a JetStream ESI source, and the 6540 Series Q-tof. HR-MS detection was calibrated to within 0.5 ppm. Samples were resolved on a C18 Eclipse column (Agilent, 2.7 µm, 2×50 mm) operating at 0.4 mL/min with a gradient of 10% MeCN in $H_2O$ (and 0.1% Formic Acid) to 95% MeCN in $H_2O$ (and 0.1% Formic Acid) over 13 min. The compounds were also characterized by NMR: $^1H$, $^{13}C$, and 2D NMR spectra were recorded on a Bruker Avance III 800 MHz spectrometer equipped with a cryoprobe. Spectra were routinely obtained in DMSO-d6, and the chemical shifts were referenced to the residual solvent peak.

Figure 21A:
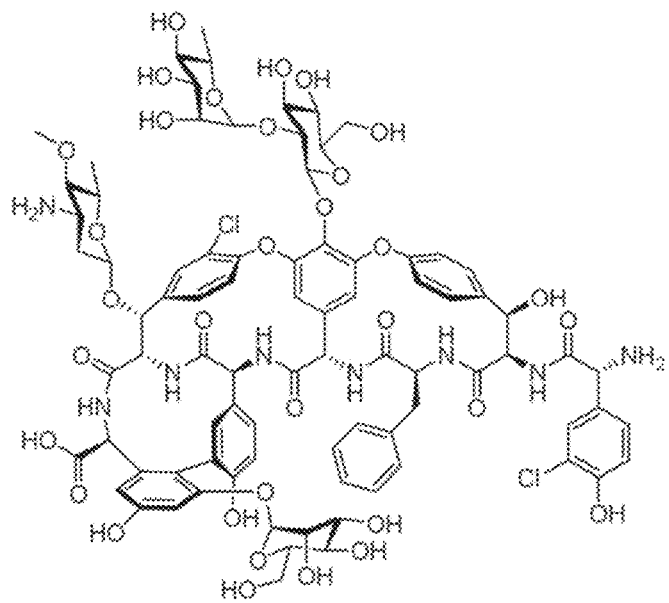
FIGS. 21A-21F are molecular structures of disclosed cryptic metabolites.
Figure 21B:
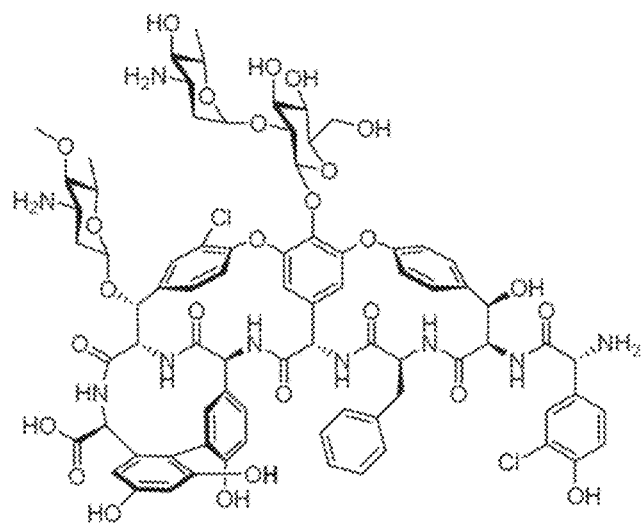
Figure 21C:
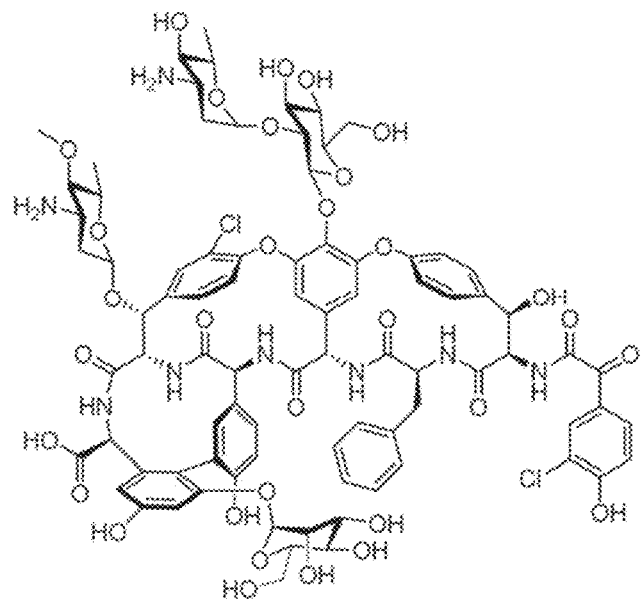
Figure 21D:
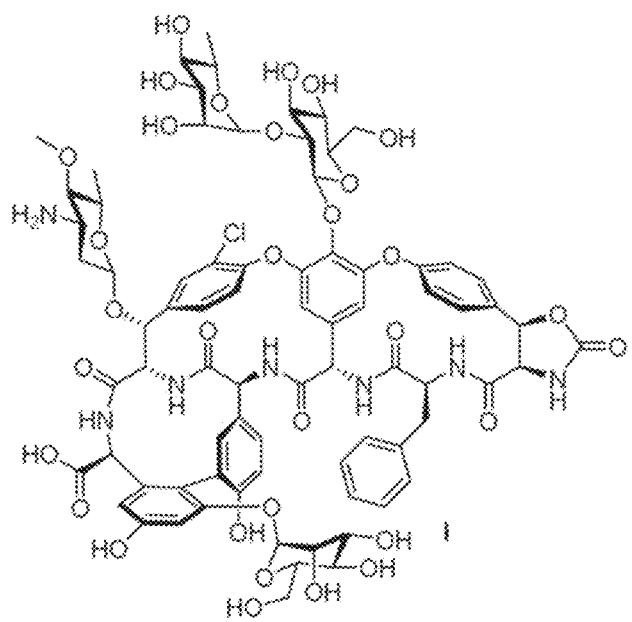
Figure 21E:
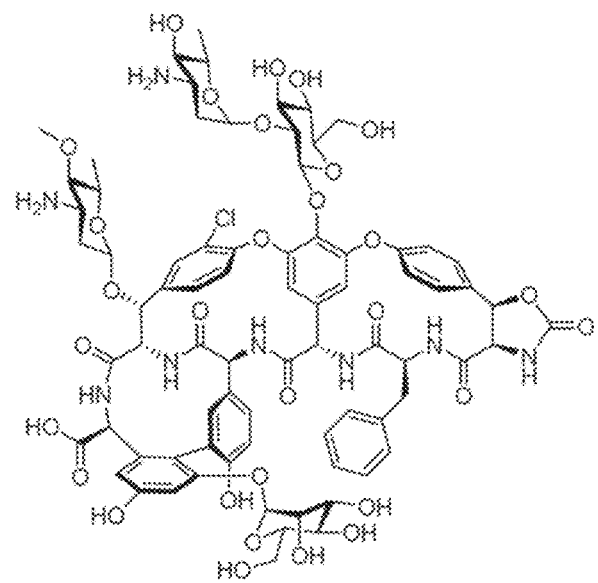
Figure 21F:
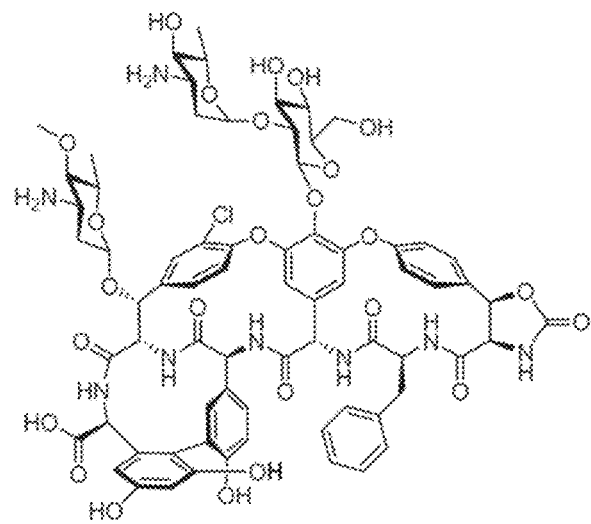

Analysis of these data allowed structural elucidation of the various compounds, seen in FIGS. 21A-21F. The compounds include: Keratinimicin A (FIG. 21A), Keratinimicin B (FIG. 21B), Keratinimicin C (FIG. 21C), Keratinicyclin A (FIG. 21D), Keratinicyclin B (FIG. 21E), and Keratinicyclin C (FIG. 21F).

These compounds are bioactive. In some instances, the compounds show activity against gram-positive bacteria. For example, although they may also show activity against gram-negative targets, the bioactivity of Keratinimicin B and C (FIGS. 21B and 21C) were tested against various gram-positive targets. The results are shown below in Table 1.

TABLE 1

| Bioactivity of Keratinimicin B and C. | | |
|---|---|---|
| Target | Keratinimicin B | Keratinimicin C |
| *S. aureus* MSSA | 8 µg/mL | 8 µg/mL |
| *S. aureus* MRSA | 4 | 8 |
| *S. pneumoniae* | 0.25 | 1 |
| *S. pyogenes* | 0.5 | 2 |
| *S. agalactiae* | 1 | 4 |
| *E. faecalis* VSE | 4 | 8 |
| *E. faecalis* VRE | >64 | >64 |
| *C. difficile* | 0.5 | 0.5 |

What is claimed is:

1. A method of inhibiting growth of bacteria or viruses, comprising contacting a microorganism with at least one compound having a molecular structure selected from:

(V)

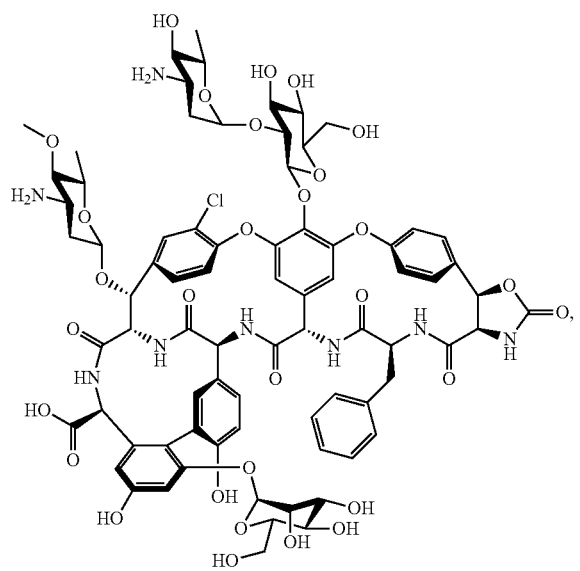

(VII)

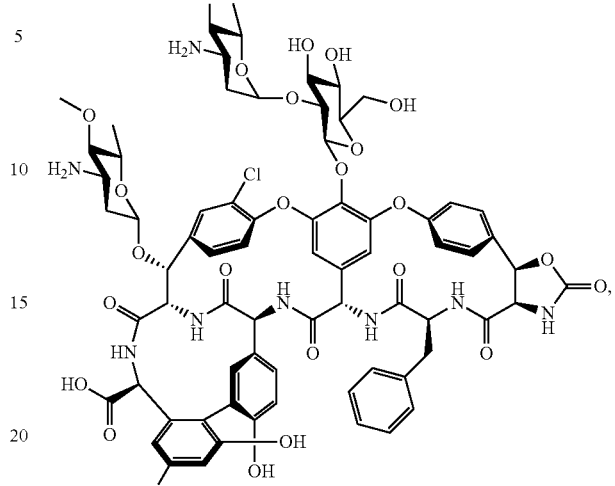

(VI)

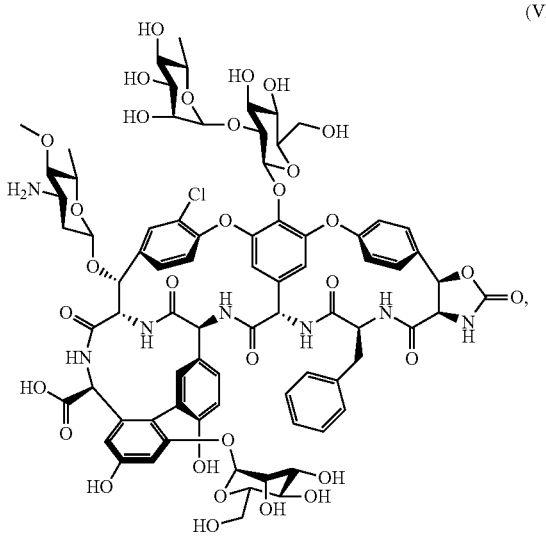

a pharmaceutically acceptable salt of (V)-(VII), or a combination thereof.

2. The method according to claim 1, wherein the microorganism is a gram-positive bacterium.

3. The method according to claim 2, wherein the gram-positive bacterium is a species selected from the group consisting of: *Staphylococcus aureus, Streptococcus agalactiae, Streptococcus pyogenes, Streptococcus pneumoniae, Clostridium difficile, Enterococcus faecalis,* and *Bacillus subtilis*.

4. The method according to claim 1, wherein the microorganism is a virus.

5. The method according to claim 4, wherein the virus is respiratory syncytial virus (RSV).

\* \* \* \* \*